United States Patent
Butler et al.

(10) Patent No.: US 12,023,357 B2
(45) Date of Patent: Jul. 2, 2024

(54) REJUVENATED AGED HEMATOPOIETIC STEM CELLS AND METHODS OF USE

(71) Applicant: Hackensack University Medical Center, Hackensack, NJ (US)

(72) Inventors: Jason Mathew Butler, New York, NY (US); Michael Gustave Poulos, Nutley, NJ (US)

(73) Assignee: Hackensack University Medical Center, Hackensack, NJ (US)

( * ) Notice: Subject to any disclaimer, the term of this patent is extended or adjusted under 35 U.S.C. 154(b) by 409 days.

(21) Appl. No.: 16/159,375

(22) Filed: Oct. 12, 2018

(65) Prior Publication Data

US 2019/0231823 A1    Aug. 1, 2019

Related U.S. Application Data

(60) Provisional application No. 62/572,130, filed on Oct. 13, 2017.

(51) Int. Cl.
| | | |
|---|---|---|
| *A61K 35/28* | (2015.01) | |
| *A61P 35/02* | (2006.01) | |
| *A61P 37/00* | (2006.01) | |
| *C12N 5/077* | (2010.01) | |
| *C12N 5/0775* | (2010.01) | |
| *C12N 5/0789* | (2010.01) | |

(52) U.S. Cl.
CPC .............. *A61K 35/28* (2013.01); *A61P 35/02* (2018.01); *A61P 37/00* (2018.01); *C12N 5/0647* (2013.01); *C12N 5/0663* (2013.01); *C12N 5/0669* (2013.01); *C12N 2502/1358* (2013.01)

(58) Field of Classification Search
None
See application file for complete search history.

(56) References Cited

U.S. PATENT DOCUMENTS

| | | | |
|---|---|---|---|
| 2007/0116691 A1 | 5/2007 | Cambier et al. | |
| 2010/0047217 A1 | 2/2010 | Refaeli et al. | |

FOREIGN PATENT DOCUMENTS

| | | | |
|---|---|---|---|
| WO | 2008/073748 A1 | 6/2008 | |

OTHER PUBLICATIONS

Poulos MG, Crowley MJP, Gutkin MC, Ramalingam P, Schachterle W, Thomas JL, Elemento O, Butler JM. Vascular Platform to Define Hematopoietic Stem Cell Factors and Enhance Regenerative Hematopoiesis. Stem Cell Reports. Nov. 10, 2015;5(5):881-894. Supplemental material (Year: 2015).*
Abbuehl JP, Tatarova Z, Held W, Huelsken J. Long-Term Engraftment of Primary Bone Marrow Stromal Cells Repairs Niche Damage and Improves Hematopoietic Stem Cell Transplantation. Cell Stem Cell. Aug. 3, 2017;21(2):241-255.e6. (Year: 2017).*
Wolff, S. Second hematopoietic stem cell transplantation for the treatment of graft failure, graft rejection or relapse after allogeneic transplantation. Bone Marrow Transplant 29, 545-552 (2002). (Year: 2002).*
Michael Gustave Poulos, PhD , Michael Gutkin, M.S. , Christopher Y. Park, MD, PhD , Jason M. Butler, PhD Rejuvenation of Aged Vascular Niches to Enhance Hematopoietic Function. Blood (2015) 126(23):781 (Year: 2015).*
Flurkey K, Currer JM, Harrison DE. 2007. The Mouse in Aging Research. In The Mouse in Biomedical Research 2nd Edition. Fox JG, et al, editors. American College Laboratory Animal Medicine (Elsevier), Burlington, Ma. pp. 637-672 (Year: 2007).*
Printout for hematopoietic system definition Google search p. 1, printed Apr. 27, 2023 (Year: 2023).*
Printout for aged definition Google search p. 1 printed Apr. 27, 2023 (Year: 2023).*
Akunuru S, and Geiger H. Aging, Clonality, and Rejuvenation of Hematopoietic Stem Cells. Trends Mol Med. 2016;22(8):701-12.
Arai F, et al., Tie2/Angiopoietin-1 Signaling Regulates Hematopoietic Stem Cell Quiescence in the Bone Marrow Niche. Cell. Jul. 23, 2004; 118(2):149-61.
Balderman Sr, et al., Targeting of the bone marrow microenvironment improves outcome in a murine model of myelodysplastic syndrome. Blood. Feb. 4, 2016; 127(5):616-25.
Balducci L. Myelosuppression and its consequences in elderly patients with cancer. Oncology (Williston Park). 2003;17(11 Suppl 11):27-32.
Beerman I, et al., Functionally distinct hematopoietic stem cells modulate hematopoietic lineage potential during aging by a mechanism of clonal expansion. Proc Natl Acad Sci U S A. Mar. 23, 2010; 107(12):5465-70.
Beerman I, et al., Proliferation-Dependent Alterations of the DNA Methylation Landscape Underlie Hematopoietic Stem Cell Aging. Cell Stem Cell. Apr. 4, 2013; 12(4):413-25.
Berger NA, et al. Cancer in the elderly. Trans Am Clin Climatol Assoc. 2006; 117(147-155; discussion 155-156.).
Brandes RP, et al. Endothelial aging. Cardiovasc Res. 2005;66(2):286-94.
Brown K, et al. SIRT3 Reverses Aging-Associated Degeneration. Cell Rep. Feb. 21, 2013; 3(2):319-27.
Busch K, et al., Fundamental properties of unperturbed haematopoiesis from stem cells in vivo. Nature. Feb. 26, 2015; 518(7540):542-6.
Butler JM, et al. Endothelial cells are essential for the self-renewal and repopulation of Notch-dependent hematopoietic stem cells. Cell stem cell. 2010;6(3):251-64.
Calvi LM, et al., Osteoblastic cells regulate the haematopoietic stem cell niche. Nature. Oct. 23, 2003; 42 (6960):841-6.
Chambers SM, et al., Aging Hematopoietic Stem Cells Decline in Function and Exhibit Epigenetic Dysregulation. PLoS Biol. Aug. 2007; 5(8):e201.

(Continued)

*Primary Examiner* — Marcia S Noble
(74) *Attorney, Agent, or Firm* — McCarter & English, LLP; Beverly W. Lubit

(57) ABSTRACT

The invention relates to rejuvenated hematopoietic stem cells and methods of use.

13 Claims, 23 Drawing Sheets
(10 of 23 Drawing Sheet(s) Filed in Color)

Specification includes a Sequence Listing.

(56) References Cited

OTHER PUBLICATIONS

Chang J, et al. Clearance of senescent cells by ABT263 rejuvenates aged hematopoietic stem cells in mice. Nat Med. Jan. 2016;22(1):78-83.
Chen C, et al. mTOR Regulation and Therapeutic Rejuvenation of Aging Hematopoietic Stem Cells. Sci Signal. 2009;2(98):ra75.
Cheng C-W, et al. Prolonged Fasting Reduces IGF-1/PKA to Promote Hematopoietic-Stem-Cell-Based Regeneration and Reverse Immunosuppression. Cell Stem Cell. Jun. 5, 2014;14(6):810-23.
Cho RH, et al.. A new mechanism for the aging of hematopoietic stem cells: aging changes the clonal composition of the stem cell compartment but not individual stem cells. Blood. 2008; 111(12):5553-61.
Christensen JL and Weissman IL. Flk-2 is a marker in hematopoietic stem cell differentiation: A simple method to isolate long-term stem cells. Proc Natl Acad Sci U S A. Dec. 4, 2001; 98(25):14541-6.
Churchman SM, et al., Transcriptional profile of native CD271+ multipotential stromal cells: Evidence for multiple fates, with prominent osteogenic and Wnt pathway signaling activity. Arthritis Rheum. Aug. 2012; 6 (8):2632-43.
Chute JP, et al. Transplantation of vascular endothelial cells mediates the hematopoietic recovery and survival of lethally irradiated mice. Blood. 2007;109(6):2365-72.
Claesson-Welsh L. Vascular permeability—the essentials. Ups J Med Sci. 2015;120(3):135-43.
Crane, G.M., et al., Adult haematopoietic stem cell niches. Nat. Rev. Immunol. 2017, 17, 573-590.
Csiszar A, et al. Inflammation and endothelial dysfunction during aging: role of NF-kappaB. J Appl Physiol (1985). 2008;105(4):1333-41.
De Haan G, et al., Mouse Strain-Dependent Changes in Frequency and Proliferation of Hematopoietic Stem Cells During Aging: Correlation Between Lifespan and Cycling Activity. Blood. Mar. 1, 1997; 89(5):1543-50.
Ding L, et al. Endothelial and perivascular cells maintain haematopoietic stem cells. Nature. 2012;48 (7382):457-62.
Ding L. and Morrison SJ. Haematopoietic stem cells and early lymphoid progenitors occupy distinct bone marrow niches. Nature. 2013;495(7440):231-5.
Donnini A, et al. Intrinsic and microenvironmental defects are involved in the age-related changes of Lin − c-kit+ hematopoietic progenitor cells. Rejuvenation Res. 2007;10(4):459-72.
Dorshkind K, and Swain S. Age-associated declines in immune system development and function: causes, consequences, and reversal. Curr Opin Immunol. 2009;21(4):404-7.
Dorshkind K, et al., The ageing immune system: is it ever too old to become young again?. Nat Rev Immunol. Jan. 2009; 9(1):57-62.
Dykstra B, and De Haan G. Hematopoietic stem cell aging and self-renewal. Cell Tissue Res. 2008;331(1):91-101.
Dykstra B, et al., Clonal analysis reveals multiple functional defects of aged murine hematopoietic stem cells. J Exp Med. Dec. 19, 2011; 208(13):2691-2703.
Eisenstaedt R, et al. Anemia in the elderly: current understanding and emerging concepts. Blood Rev. 2006;20(4):213-26.
El Assar M, et al. Oxidative stress and vascular inflammation in aging. Free Radic Biol Med. 2013;65(380-401.).
Elias HK, et al. Molecular mechanisms underlying lineage bias in aging hematopoiesis. Semin Hematol. 2017;54(1):4-11.
Ergen AV, et al., Rantes/Ccl5 influences hematopoietic stem cell subtypes and causes myeloid skewing. Blood. Mar. 15, 2012; 119(11):2500-9.
Fazeli PK, et al. Marrow Fat and Bone—New Perspectives. J Clin Endocrinol Metab. Mar. 2013, 98(3):935-45.
Federal Interagency Forum On Aging Related Statistics. Older Americans 2016: Key Indicators of Well-Being. https://agingstats.gov/. 204 pages.
Fels, J., et al., Nanomechanics of vascular endothelium. 2014 Cell Tissue Res. 355, 727-737.

Florian MC and Geiger H. Concise Review: Polarity in Stem Cells, Disease, and Aging. Stem Cells. Sep. 2010; 28(9):1623-1629.
Florian MC, et al., Cdc42 Activity Regulates Hematopoietic Stem Cell Aging and Rejuvenation. Cell Stem Cell. May 4, 2012; 10(5):520-30.
Geiger H and Rudolph KL., Aging in the lympho-hematopoietic stem cell compartment. Trends Immunol. Jul. 2009; 30(7):360-5.
Geiger H, et al. The ageing haematopoietic stem cell compartment. Nat Rev Immunol. 2013;13(5):376-89.
Geiger H, et al., Age- and stage-specific regulation patterns in the hematopoietic stem cell hierarchy. Blood. Nov. 15, 2001; 98(10):2966-72.
Geiger H, et al., Stem Cells, Aging, Niche, Adhesion and Cdc42. A Model for Changes in Cell-Cell Interactions and Hematopoietic Stem Cell Aging. Cell Cycle. Apr. 15, 2007; 6(8):884-887.
Gekas C and Graf T., CD41 expression marks myeloid-biased adult hematopoietic stem cells and increases with age. Blood. May 30, 2013; 121(22):4463-72.
Gomez-Lopez, S., et al., Asymmetric cell division of stem and progenitor cells during homeostasis and cancer. Cell. Mol. Life Sci. 2014, 71, 575-597.
Greenbaum A., et al. CXCL12 in early mesenchymal progenitors is required for haematopoietic stem-cell maintenance. Nature. 2013;495(7440):227-30.
Grinenko T, et al., Clonal expansion capacity defines two consecutive developmental stages of long-term hematopoietic stem cells. J Exp Med. Feb. 10, 2014; 211(2):209-15.
Grover A, et al., Single-cell RNA sequencing reveals molecular and functional platelet bias of aged haematopoietic stem cells. Nat Commun. Mar. 24, 2016; 7:11075.
Guarente L. and Kenyon C., Genetic pathways that regulate ageing in model organisms. Nature. Nov. 9, 2000; 408(6809):255-62.
Guidi N, et al. Osteopontin attenuates aging-associated phenotypes of hematopoietic stem cells. EMBO J. 840-853. 2017.
Harichandan A, et al. Prospective Isolation and Characterization of Human Bone Marrow-Derived MSCs. Adv Biochem Eng Biotechnol. 2013; 129:1-17.
Hartshorn et al., Cell Technology for Cell Products, Ex Vivo Expansion of Hematopoietic Stem Cells Using Defined Culture Media. pp. 221-224, R. Smith, Editor; Springer Netherlands, 2007.
Heazlewood SY, et al., Megakaryocytes co-localise with hemopoietic stem cells and release cytokines that up-regulate stem cell proliferation. Stem Cell Res. Sep. 2013; 11(2):782-92.
Himburg HA, et al. Pleiotrophin regulates the expansion and regeneration of hematopoietic stem cells. Nat Med. 2010;16(4):475-82.
Hooper AT, et al. Engraftment and reconstitution of hematopoiesis is dependent on VEGFR2-mediated regeneration of sinusoidal endothelial cells. Cell stem cell. 2009;4(3):263-74.
Hisu, Y-C., et al., Emerging interactions between skin stem cells and their niches. Nat. Med. 20, 847-856 (Aug. 2014).
Hu Y, and Smyth GK. ELDA: extreme limiting dilution analysis for comparing depleted and enriched populations in stem cell and other assays. J Immunol Methods. 2009;347(1-2):70-8.
Jaiswal S, et al., Age-Related Clonal Hematopoiesis Associated with Adverse OutcomesN Engl J Med. Dec. 25, 2014; 371(26):2488-98.
Janzen V, et al., Stem-cell ageing modified by the cyclin-dependent kinase inhibitor p16INK4a. Nature. Sep. 28, 2006; 443(7110):421-6.
Jung Y, et al., Regulation of SDF-1 (CXCL 12) production by osteoblasts; a possible mechanism for stem cell homing. Bone. Apr. 2006; 38(4):497-508.
Kamminga LM, et al., Impaired Hematopoietic Stem Cell Functioning After Serial Transplantation and During Normal Aging. Stem Cells. 2005; 23(1):82-92.
Katayama Y, et al., Signals from the Sympathetic Nervous System Regulate Hematopoietic Stem Cell Egress from Bone Marrow. Cell. Jan. 27, 2006; 124(2):407-21.
Keyes, BE., et al., Nfatc1 orchestrates aging in hair follicle stem cells. PNAS 110, E4950-E4959 (Dec. 17, 2013).
Kfoury Y and Scadden DT. Mesenchymal Cell Contributions to the Stem Cell Niche. Cell Stem Cell. Mar. 5, 2015; 16(3):239-53.

(56) References Cited

OTHER PUBLICATIONS

Kiel MJ, et al., SLAM Family Receptors Distinguish Resource Hematopoietic Stem and Progenitor Cells and Reveal Endothelial Niches for Stem Cells. Cell. Jul. 1, 2005; 121(7):1109-21.
Kobayashi H, et al. Angiocrine factors from Akt-activated endothelial cells balance self-renewal and differentiation of haematopoietic stem cells. Nature cell biology. 2010;12(11):1046-56.
Kollman C, et al., Donor characteristics as risk factors in recipients after transplantation of bone marrow from unrelated donors: the effect of donor age. Blood. Oct. 1, 2001; 98(7):2043-51.
Koubova J and Guarente L, How does calorie restriction work?. Genes Dev. Feb. 1, 2003; 17(3):313-21.
Kusumbe AP, et al. Age-dependent modulation of vascular niches for haematopoietic stem cells. Nature. 2016. 532(7599):380-4.
Lampugnani, M. G. Cell Migration into a Wounded Area In Vitro. (1999). Methods in Mol Biol 96: 177-182.
Latchney SE, and Calvi LM. The aging hematopoietic stem cell niche: Phenotypic and functional changes and mechanisms that contribute to hematopoietic aging. Semin Hematol. 2017;54(1):25-32.
Li B, et al. Endothelial cells mediate the regeneration of hematopoietic stem cells. Stem Cell Res. 2010;4(1):17-24.
Li, XM, et al.. Bone marrow sinusoidal endothelial cells undergo nonapoptotic cell death and are replaced by proliferating sinusoidal cells in situ to maintain the vascular niche following lethal irradiation. Experimental hematology. 2008;36(9):1143-56.
Liang Y, et al., Effects of aging on the homing and engraftment of murine hematopoietic stem and progenitor cells. Blood. Aug. 15, 2005; 106(4):1479-87.
Lichtman MA and Rowe JM, The relationship of patient age to the pathobiology of the clonal myeloid diseases. Semin Oncol. Apr. 2004; 31(2):185-97.
Liu, L.,et al., Chromatin Modifications as Determinants of Muscle Stem Cell Quiescence and Chronological Aging. Cell Rep. 4, 189-204 (Jul. 11, 2013).
Liu, Y et al., Ex vivo expansion of hematopoietic stem cells derived from umbilical cord blood in rotating wall vessel. Journal of Biotechnology 124:592-601, 2006.
Miller JP and Allman D, Linking age-related defects in B lymphopoiesis to the aging of hematopoietic stem cells. Semin Immunol. Oct. 2005; 17(5):321-9.
Mittal M, et al. Reactive oxygen species in inflammation and tissue injury. Antioxid Redox Signal. 2014;2(7):1126-67.
Mizoguchi T,et al., Osterix Marks Distinct Waves of Primitive and Definitive Stromal Progenitors during Bone Marrow Development. Dev Cell. May 12, 2014; 29(3):340-9.
Mohrin M, et al. Stem Cell Aging. A mitochondrial UPR-mediated metabolic checkpoint regulates hematopoietic stem cell aging. Science. Mar. 20, 2015;347(6228):1374-7.
Montfort MJ, et al. Adult blood vessels restore host hematopoiesis following lethal irradiation. Experimental hematology. 2002;30(8):950-6.
Morikawa S, et al., Prospective identification, isolation, and systemic transplantation of multipotent mesenchymal stem cells in murine bone marrow. J Exp Med. Oct. 26, 2009; 206(11):2483-96.
Morrison SJ and Weissman IL. The long-term repopulating subset of hematopoietic stem cells is deterministic and isolatable by phenotype. Immunity. Nov. 1994; 1(8):661-73.
Morrison SJ, et al. Identification of a lineage of multipotent hematopoietic progenitors. Development. May 1997; 124(10):1929-39.
Morrison SJ, et al. The aging of hematopoietic stem cells. Nat Med. Sep. 1996; 2(9):1011-6.
Morrison, S.J., et al., The bone marrow niche for haematopoietic stem cells. Nature 2014, 505, 327-334.
Méndez-Ferrer S, et al., Mesenchymal and haematopoietic stem cells form a unique bone marrow niche. Nature. Aug. 12, 2010; 466(7308):829-34.

Nakamura Y, et al., Isolation and characterization of endosteal niche cell populations that regulate hematopoietic stem cells. Blood. Sep. 2, 2010; 116(9):1422-32.
Nibley WE and Spangrude GJ, Primitive stem cells alone mediate rapid marrow recovery and multilineage engraftment after transplantation. Bone Marrow Transplant. Feb. 1998; 21(4):345-54.
North BJ, and Sinclair DA. The intersection between aging and cardiovascular disease. Circ Res. 2012;110(8):1097-108.
Notta F, et al., Isolation of Single Human Hematopoietic Stem Cells Capable of Long-Term Multilineage Engraftment. Science. Jul. 8, 2011; 333(6039):218-21.
Notta, F. et al., Distinct routes of lineage development reshape the human blood hierarchy across ontogeny. Science 2016, 351.
Oguro H, et al. SLAM Family Markers Resolve Functionally Distinct Subpopulations of Hematopoietic Stem Cells and Multipotent Progenitors. Cell Stem Cell. Jul. 3, 2013; 13(1):102-16.
Omatsu Y, et al.,The Essential Functions of Adipo-osteogenic Progenitors as the Hematopoietic Stem and Progenitor Cell Niche. Immunity. Sep. 24, 2010; 33(3):387-99.
Osawa M, et al., Long-Term Lymphohematopoietic Reconstitution by a Single CD34-Low/Negative Hematopoietic Stem Cell . Science. Jul. 12, 1996; 273(5272):242-5.
Paneni F, et al. The Aging Cardiovascular System: Understanding It at the Cellular and Clinical Levels. J Am Coll Cardiol. 2017;69(15):1952-67.
Pang WW, et al. Age-associated changes in human hematopoietic stem cells. Semin Hematol. 2017;54(1):39-42.
Pang WW, et al., Human bone marrow hematopoietic stem cells are increased in frequency and myeloid-biased with age. Proc Natl Acad Sci U S A. Dec. 13, 2011; 108(50):20012-7.
Passegué, E, et al. Global analysis of proliferation and cell cycle gene expression in the regulation of hematopoietic stem and progenitor cell fates. J Exp Med. Dec. 5, 2005; 202(11):1599-611.
Pietras, EM et al., Functionally Distinct Subsets of Lineage-Biased Multipotent Progenitors Control Blood Production in Normal and Regenerative Conditions. Cell Stem Cell 2015, 17, 35-46.
Pober JS, and Sessa WC. Evolving functions of endothelial cells in inflammation. Nat Rev Immunol. 2007;7(10):803-15.
Poulos MG, et al. Endothelial Jagged-1 is necessary for homeostatic and regenerative hematopoiesis. Cell Reports. 2013;4(5):1022-34.
Poulos MG, et al. Endothelial-specific inhibition of NF-kappaB enhances functional haematopoiesis. Nat Commun. 2016;7(13829.).
Poulos MG, et al. Vascular Platform to Define Hematopoietic Stem Cell Factors and Enhance Regenerative Hematopoiesis. Stem Cell Reports. 2015;5(5):881-94.
Qian H, et al., Critical Role of Thrombopoietin in Maintaining Adult Quiescent Hematopoietic Stem Cells. Cell Stem Cell. Dec. 13, 2007; 1(6):671-84.
Renault, VM., et al., FoxO3 Regulates Neural Stem Cell Homeostasis. Cell Stem Cell. 5, 527-539 (Nov. 6, 2009).
Rodgers, JT, et al., mTORC1 controls the adaptive transition of quiescent stem cells from G0 to GAlert. Nature 510, 393-396 (Jun. 19, 2014).
Rossi DJ, et al., Cell intrinsic alterations underlie hematopoietic stem cell aging. Proc Natl Acad Sci U S A. Jun. 28, 2005; 102(26):9194-9.
Salter AB, et al. Endothelial progenitor cell infusion induces hematopoietic stem cell reconstitution in vivo. Blood. 2009;113(9):2104-7.
Sanjuan-Pla, A.et al., Platelet-biased stem cells reside at the apex of the haematopoietic stem-cell hierarchy. Nature 2013, 502, 232-236.
Satoh Y, et al. The Satb1 Protein Directs Hematopoietic Stem Cell Differentiation toward Lymphoid Lineages. Immunity. Jun. 27, 2013;38(6):1105-15.
Schlitzkus LL, et al. Perioperative management of elderly patients. Surg Clin North Am. 2015;95(2):391-415.
Schofield, R., The relationship between the spleen colony-forming cell and the haemopoietic stem cell. Blood Cells 1978, 4, 7-25.
Shin JY, et al. High c-Kit expression identifies hematopoietic stem cells with impaired self-renewal and megakaryocytic bias. J Exp Med. Feb. 10, 2014; 211(2):217-31.

(56) References Cited

OTHER PUBLICATIONS

Smith BD, et al., Future of Cancer Incidence in the United States: Burdens Upon an Aging, Changing Nation. J Clin Oncol. Jun. 10, 2009; 27(17):2758-65.
Spandidos A, et al. A comprehensive collection of experimentally validated primers for Polymerase Chain Reaction quantitation of murine transcript abundance. BMC genomics. 2008;9:633.
Spandidos A, et al. PrimerBank: a resource of human and mouse PCR primer pairs for gene expression detection and quantification. Nucleic Acids Research. 2010;38(Database issue):D792-799.
Spangrude GJ, et al., Purification and characterization of mouse hematopoietic stem cells. Science. Jul. 1, 1988; 241(4861):58-62.
Sudo K, et al., Age-associated Characteristics of Murine Hematopoietic Stem Cells. J Exp Med. Nov. 6, 2000; 192(9):1273-80.
Sun J, et al., Clonal dynamics of native haematopoiesis. Nature. Oct. 16, 2014; 514(7522):322-7.
Taichman RS and Emerson SG. Human osteoblasts support hematopoiesis through the production of granulocyte colony stimulating factor. J Exp Med. May 1, 1994; 179(5):1677-82.
Takahashi K, et al, Induction of Pluripotent Stem Cells from Mouse Embryonic and Adult Fibroblast Cultures by Defined Factors. Cell. Aug. 25, 2006; 126(4):663-76.
Tang, AH. and Rando, TA., Induction of autophagy supports the bioenergetic demands of quiescent muscle stem cell activation. EMBO J. 33, 2782-2797 (Dec. 1, 2014).
Tian XL, and Li Y. Endothelial cell senescence and age-related vascular diseases. J Genet Genomics. 2014;41(9):485-95.
Till JE, and McCulloch, EA. A direct measurement of the radiation sensitivity of normal mouse bone marrow cells. Radiat Res. 1961;14(213-22.
Tuljapurkar SR, et al., Changes in human bone marrow fat content associated with changes in hematopoietic stem cell numbers and cytokine levels with aging. J Anat. Nov. 2011; 219(5):574-81.
Van Zant G, and Liang Y. The role of stem cells in aging. Experimental hematology. 2003;31(8):659-72.
Vas V, et al. Aging of the microenvironment influences clonality in hematopoiesis. PLoS One. 2012;7(8):e42080.
Vas V, et al., Contribution of an Aged Microenvironment to Aging-Associated Myeloproliferative Disease. PLoS One. 2012; 7(2):e31523.
Verfaillie, CM., Optimizing hematopoietic stem cell engraftment: a novel role for thrombopoietin. J. Clin Invest. 2002; 110(3): 303-304.
Verovskaya E, et al., Heterogeneity of young and aged murine hematopoietic stem cells revealed by quantitative clonal analysis using cellular barcoding. Blood. Jul. 25, 2013; 122(4):523-32.
Visnjic D, et al., Hematopoiesis is severely altered in mice with an induced osteoblast deficiency. Blood. May 1, 2004; 103(9):3258-64.
Wahlestedt M, et al., An epigenetic component of hematopoietic stem cell aging amenable to reprogramming into a young state. Blood. May 23, 2013; 121(21):4257-64.
Wang X, and Seed B. A PCR primer bank for quantitative gene expression analysis. Nucleic acids research. 2003. 31(24):e154.
Wang, J., et al. Per2 induction limits lymphoid-biased haematopoietic stem cells and lymphopoiesis in the context of DNA damage and ageing. Nature Cell Biology vol. 18, pp. 480-490 (2016).
Webb, AE., et al., FOXO3 Shares Common Targets with ASCL1 Genome-wide and Inhibits ASCL1-Dependent Neurogenesis. Cell Rep. 4, 477-491 (Aug. 15, 2013).
Wong AK, et al. A Parallel-Plate Flow Chamber for Mechanical Characterization of Endothelial Cells Exposed to Laminar Shear Stress. Cell Mol Bioeng. 2016;9(1):127-38.
Woolthuis CM and Park CY, Hematopoietic stem/progenitor cell commitment to the megakaryocyte lineage. Blood. Mar. 10, 2016; 127(10):1242-8.
Xing Z, et al., Increased hematopoietic stem cell mobilization in aged mice. Blood. Oct. 1, 2006; 108(7):2190-7.
Yancik R. Population Aging and Cancer: A Cross-National Concern. Cancer J. Nov.-Dec. 2005; 11(6):437-41.
Zhang C. The role of inflammatory cytokines in endothelial dysfunction. Basic Res Cardiol. 2008;103(5):398-406.
Zhang J, et al., Identification of the haematopoietic stem cell niche and control of the niche size. Nature. Oct. 23, 2003; 425(6960):836-41.
Zhao M, et al., Megakaryocytes maintain homeostatic quiescence and promote post-injury regeneration of hematopoietic stem cells. Nat Med. Nov. 2014; 20(11):1321-6.
Zhu J, et al., Osteoblasts support B-lymphocyte commitment and differentiation from hematopoietic stem cells. Blood. May 1, 2007; 109(9):3706-12.

* cited by examiner

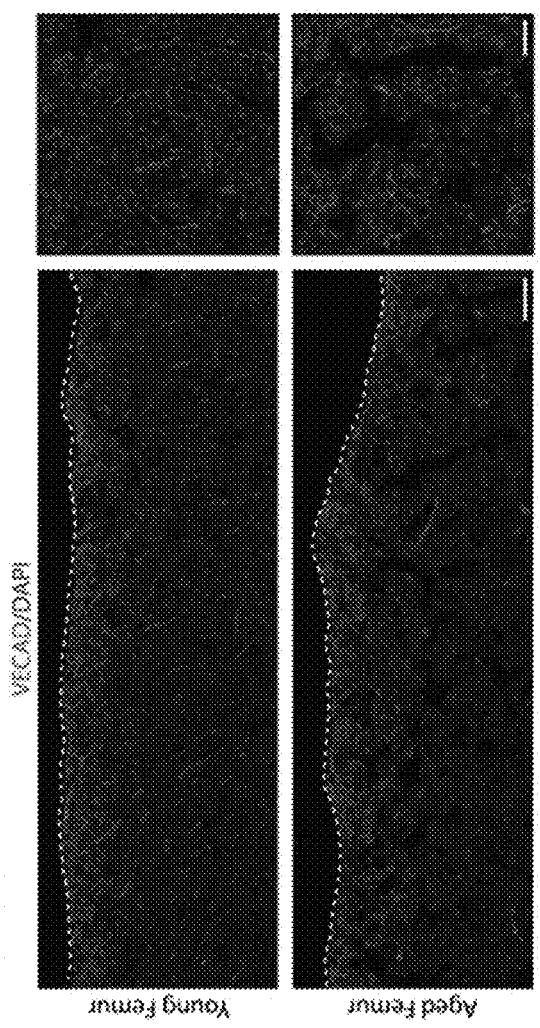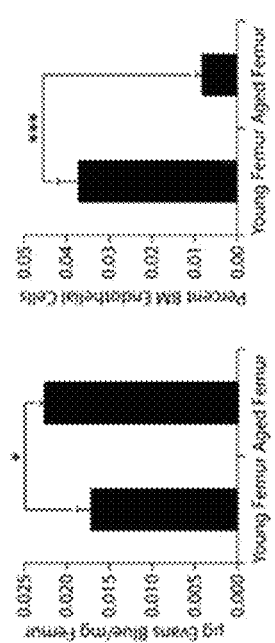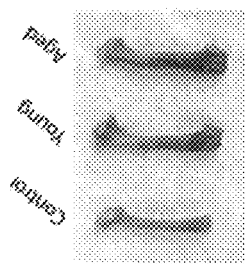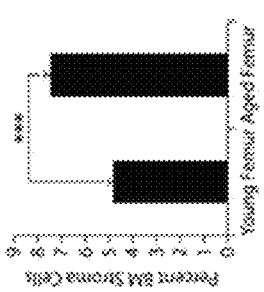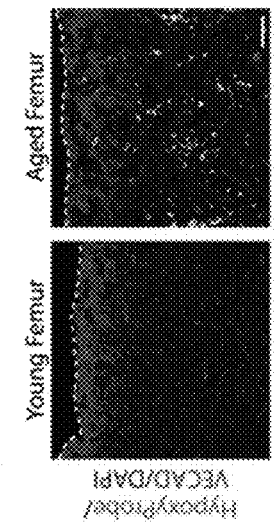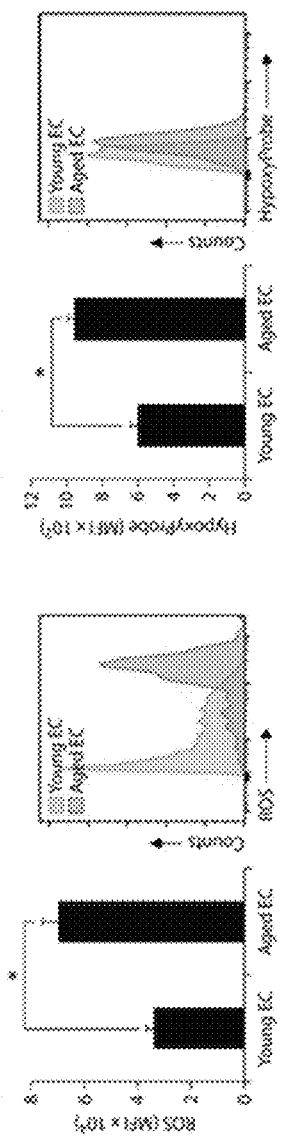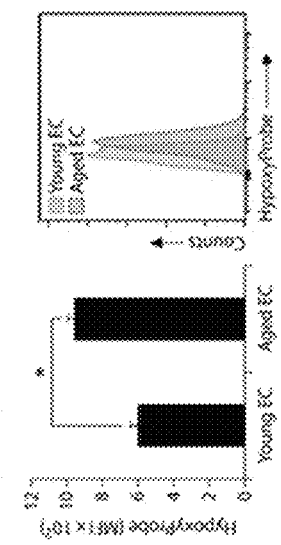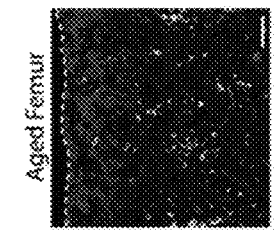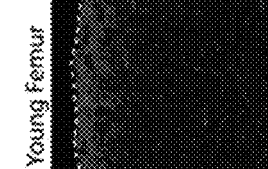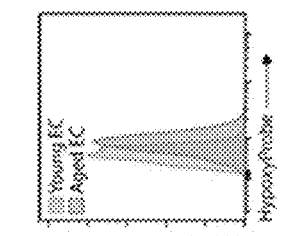

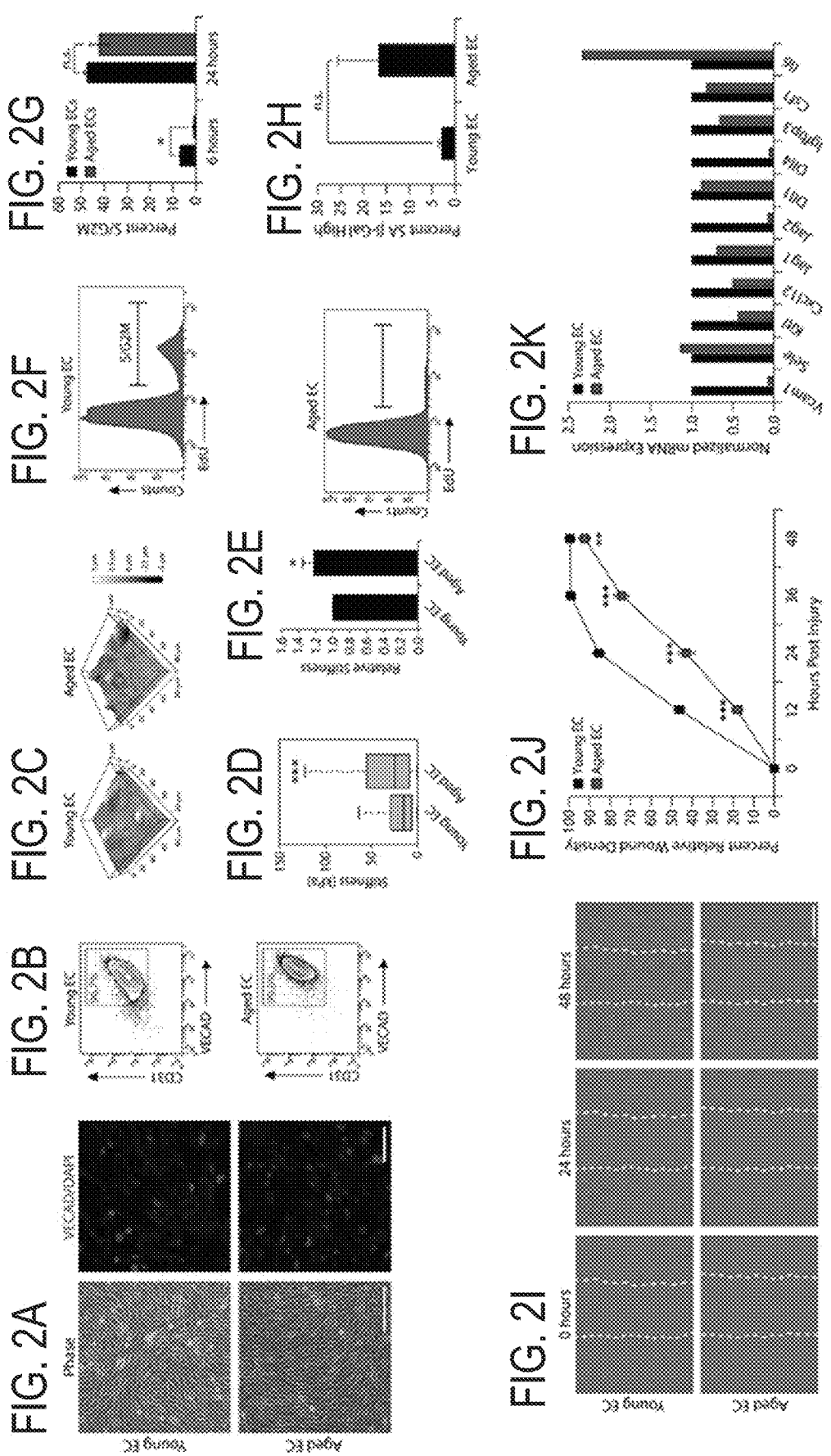

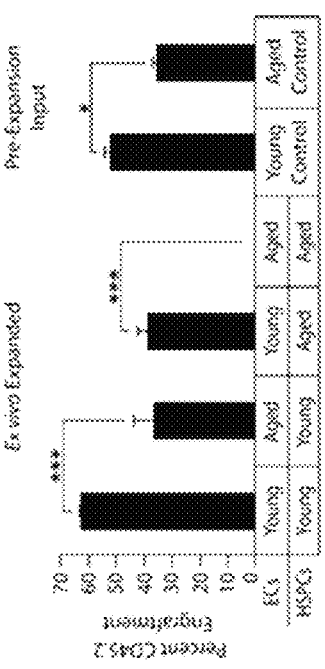
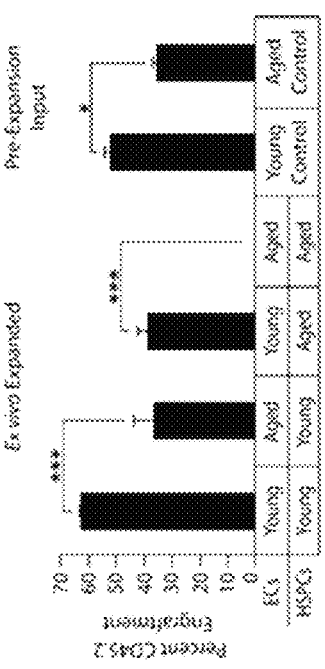
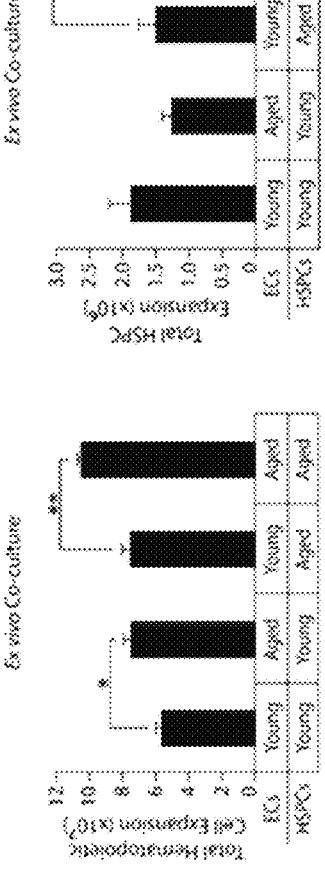
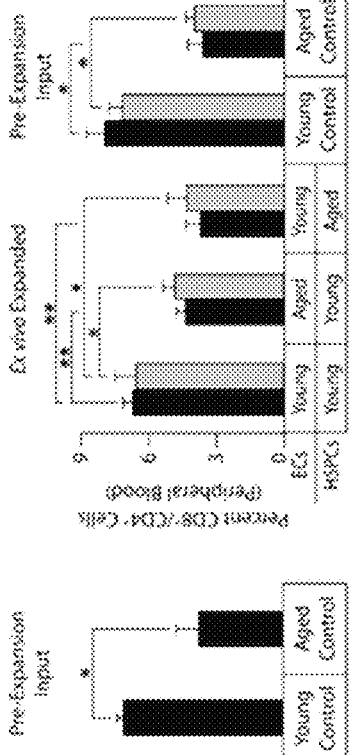
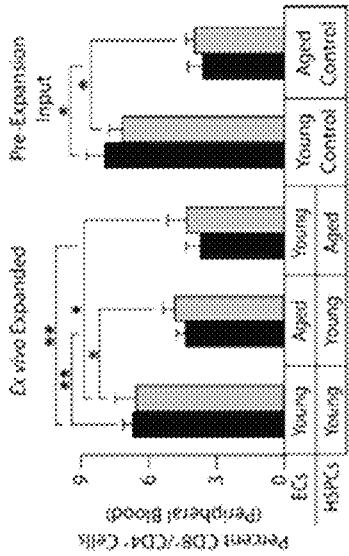
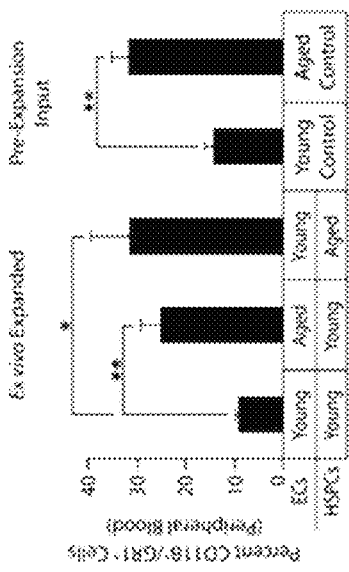

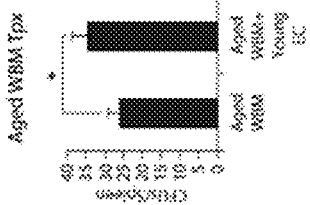
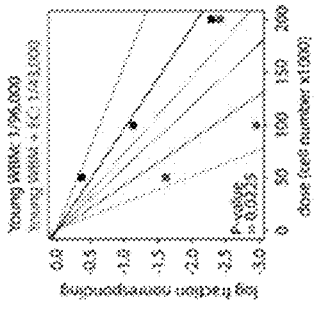
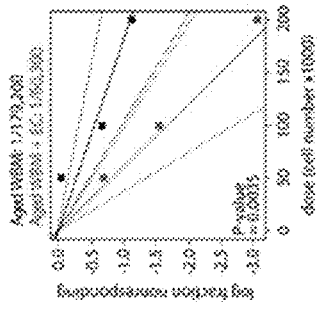
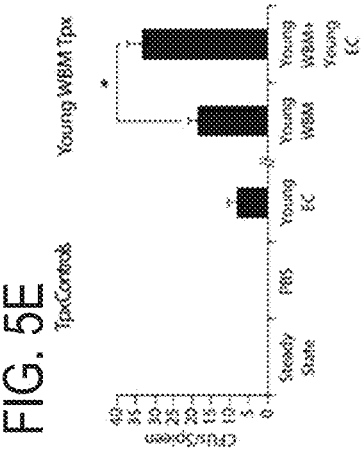
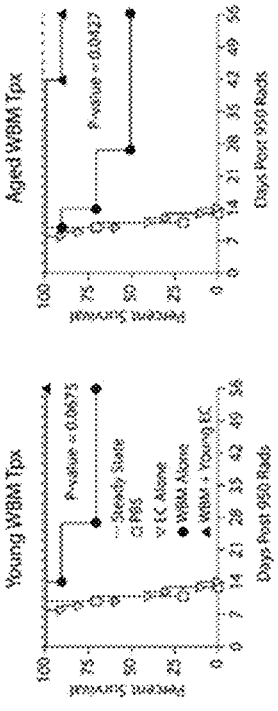
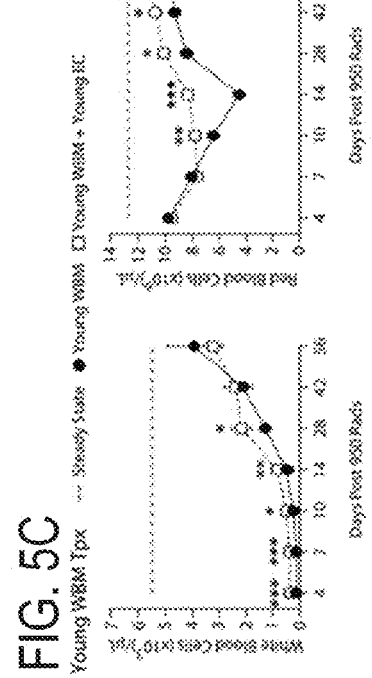
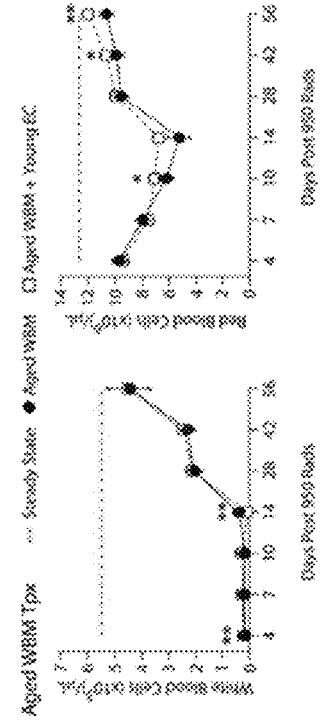

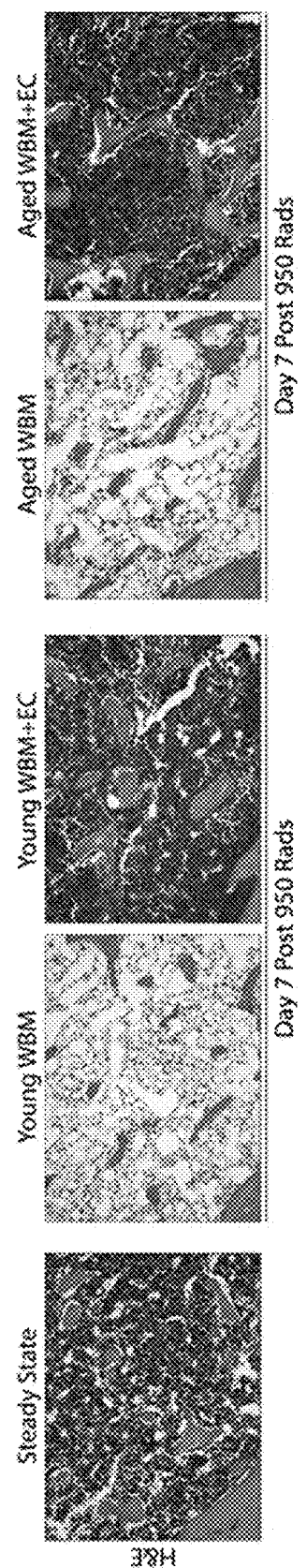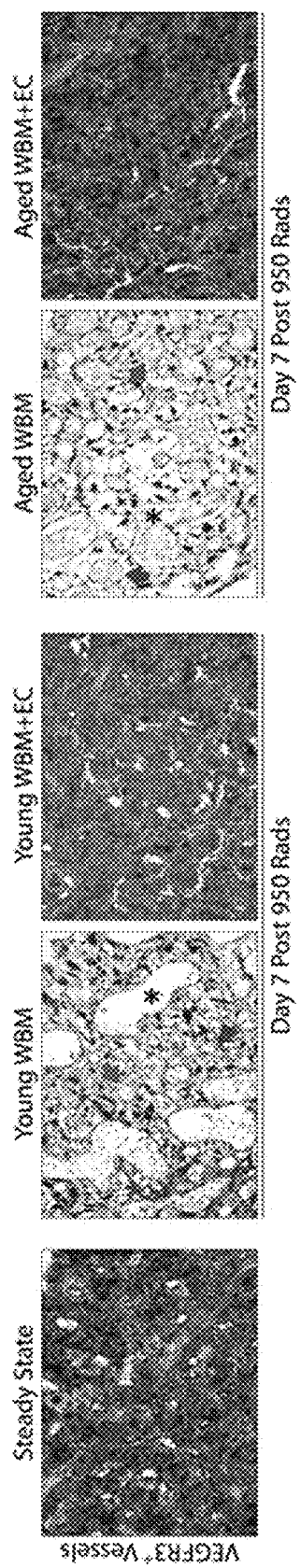

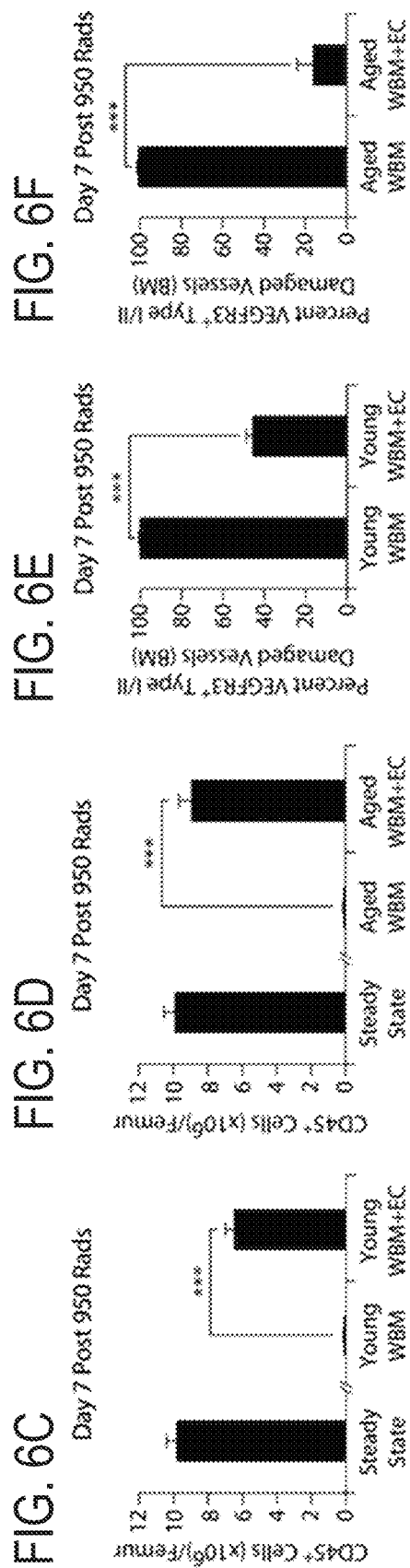

FIG. 7C
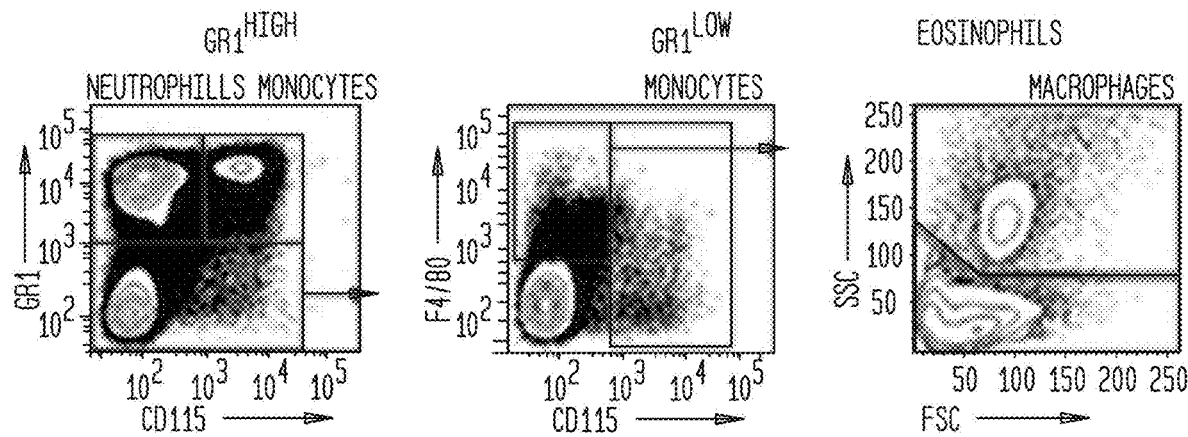
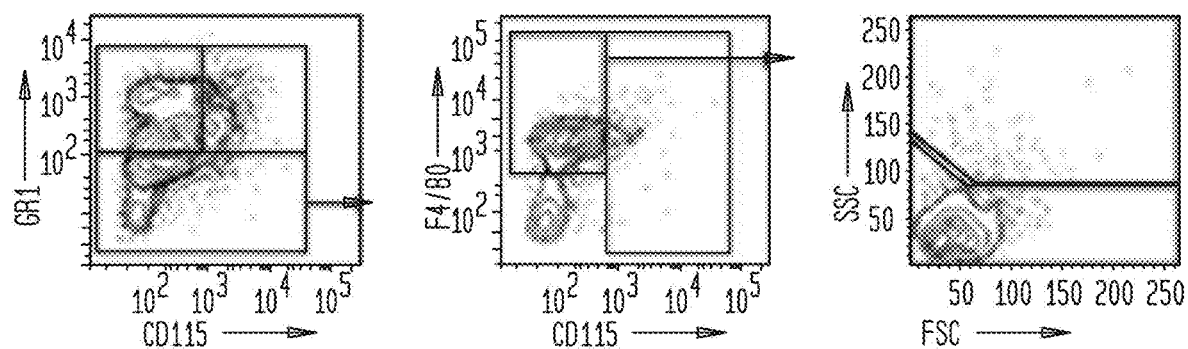
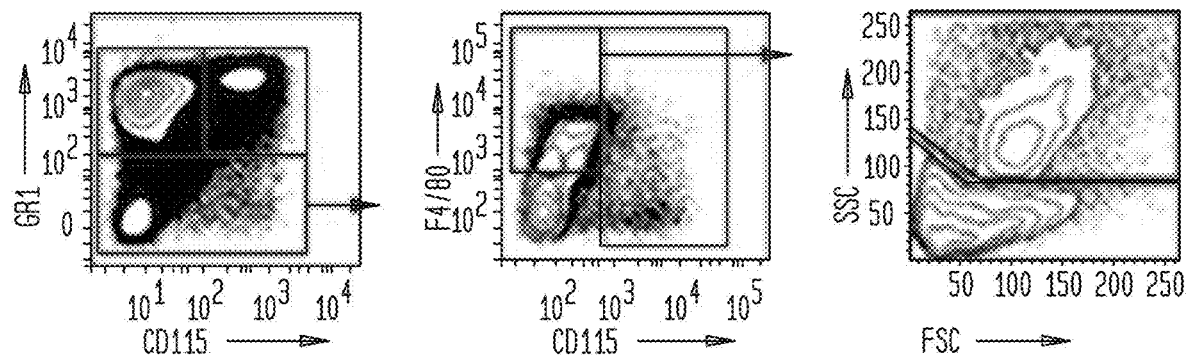

FIG. 7D
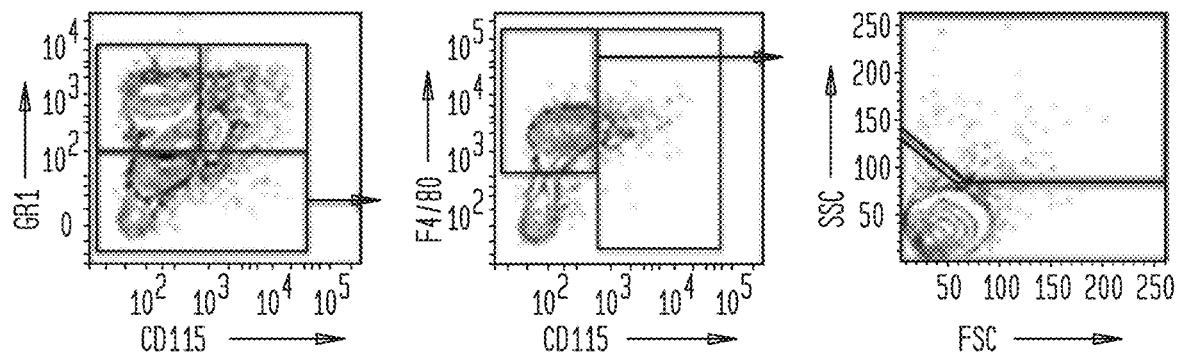
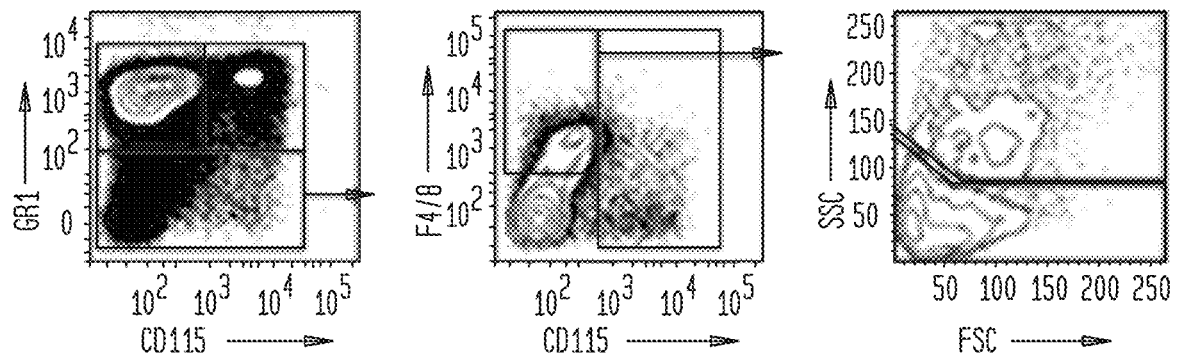

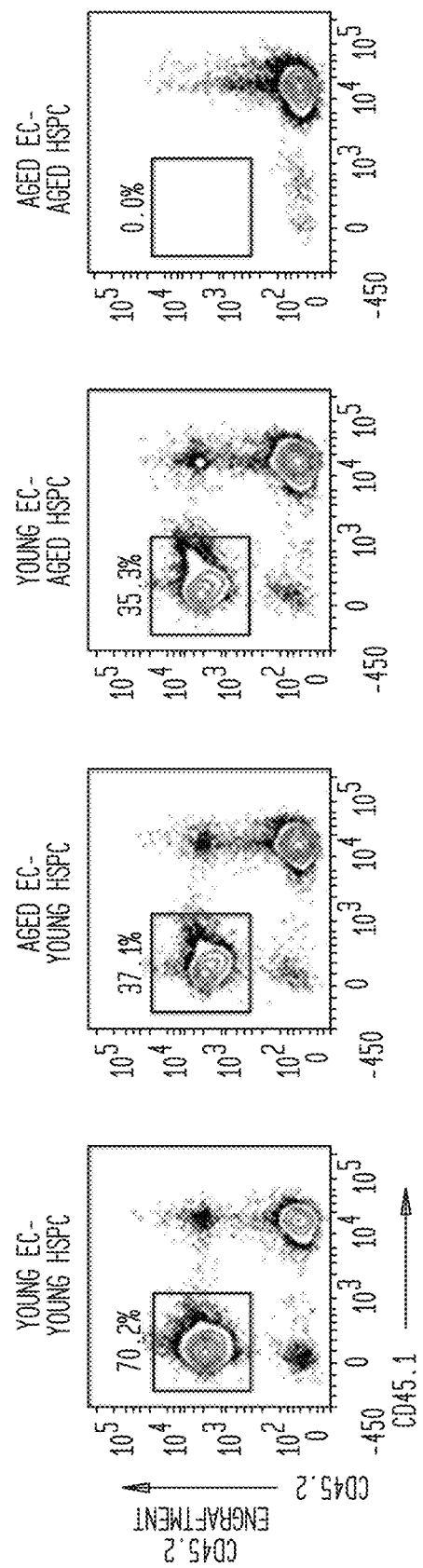

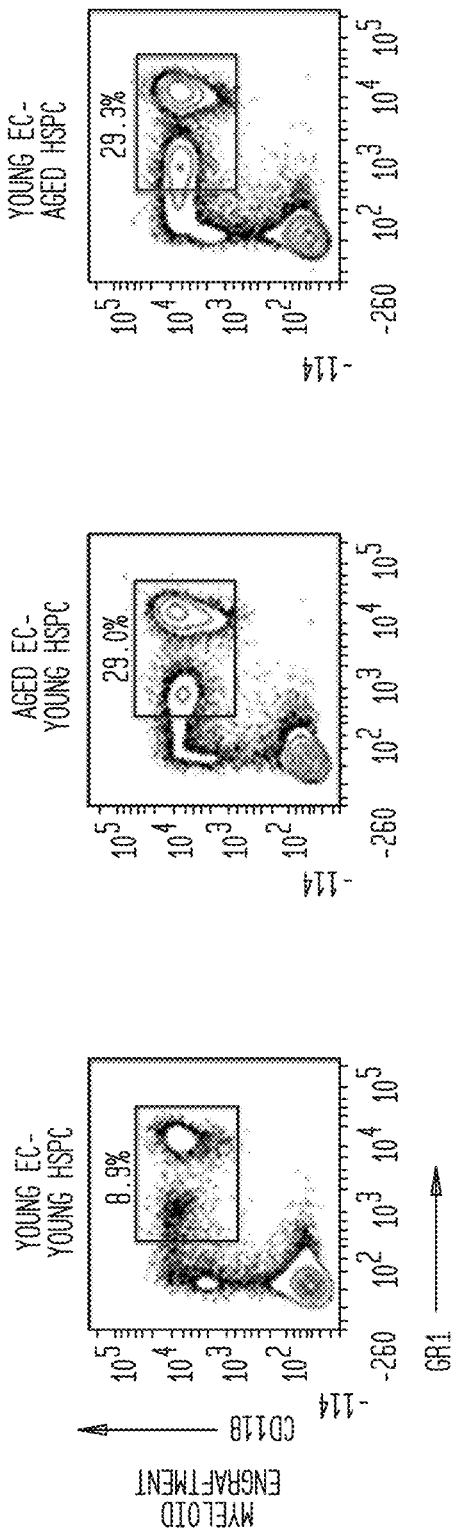

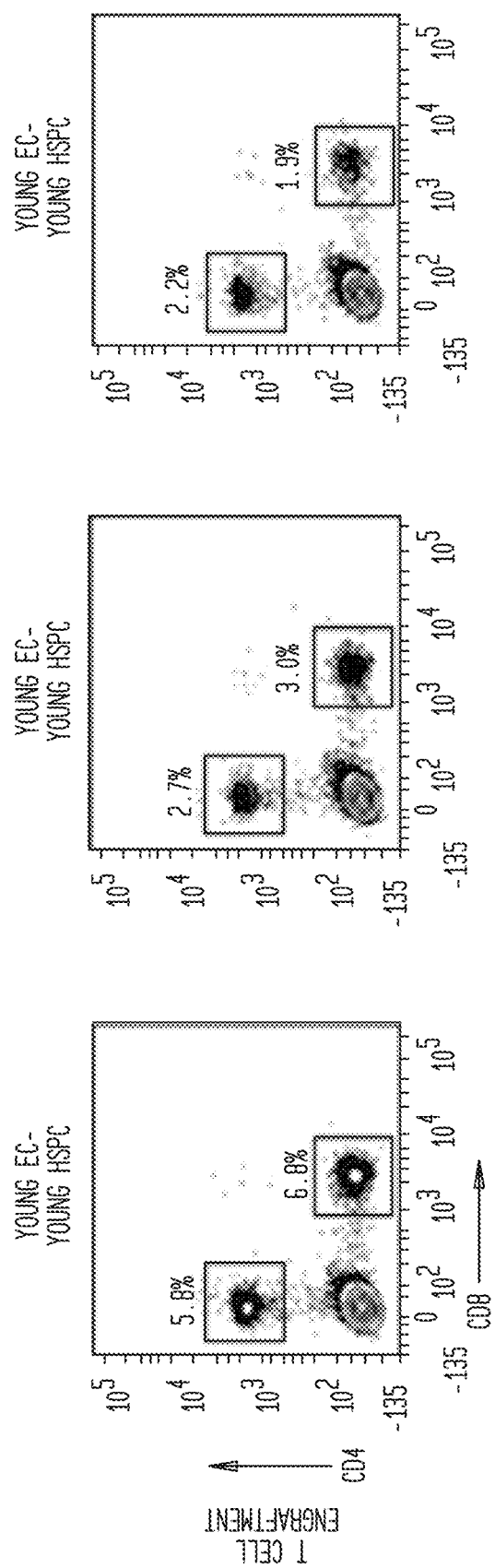

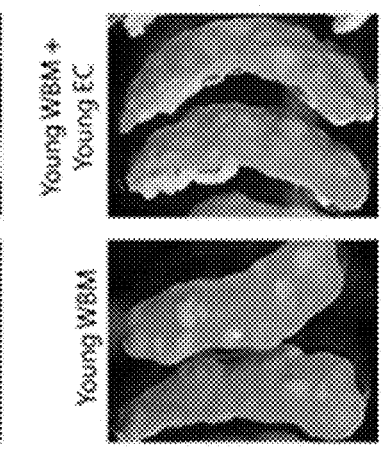
FIG. 10B
FIG. 10C
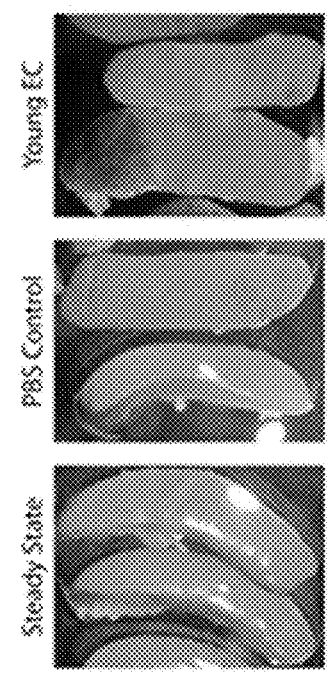
FIG. 10A

REJUVENATED AGED HEMATOPOIETIC STEM CELLS AND METHODS OF USE

RELATED APPLICATION

The present application claims priority to U.S. Provisional Application No. 62/572,130, filed on Oct. 13, 2017, entitled Methods for Promoting Hematopoietic Stem Cells Function, the entire contents of which is incorporated by reference in its entirety herein.

SEQUENCE LISTING

The instant application contains a Sequence Listing which has been submitted electronically in ASCII format and is hereby incorporated by reference in its entirety. Said ASCII copy, created on Oct. 31, 2018, is named 128533-01801_SeqID_ST25.txt and is 3,911 bytes in size.

BACKGROUND OF THE INVENTION

Despite its central role in the life cycle of a human being, aging remains one of the least understood processes of human biology. Aging is characterized by physiological decline and increased susceptibility to pathologies and mortality. The number of elderly individuals is expected to double in the next forty years, creating an increased burden of treatment for aging-related disorders, including cardiovascular disease and cancer (1-4). Aging is associated with a gradual functional decline of a variety of organs and tissues and is the highest risk factor for cancer (Smith B D, et al., J Clin Oncol. 2009 Jun. 10; 27(17):2758-65; Yancik R Cancer J. 2005 November-December; 11(6):437-41). Yet in spite of this approaching burden on the world's healthcare systems, a basic understanding of the mechanisms of aging and basic treatments to combat aging are lacking. With the onset of a demographic shift towards an older population, understanding mechanisms regulating the complex process of aging is important for understanding aging-associated disease development and promoting a longer and healthier lifespan. Stem cells, with self-renewal and multi-lineage differentiation properties, generate distinct tissue-specific cell types during development and later support homeostatic maintenance and tissue repair. During the process of aging, cells are continuously exposed to both cell-intrinsic and -extrinsic stress factors; the effects of stress on long-lasting stem cells can cause damage accumulation and impair long-term tissue homeostasis.

Blood formation, or hematopoiesis, originates from hematopoietic stem cells, whose functions and maintenance are regulated in both cell- and cell non-autonomous ways. The hematopoietic system depends on the constant replenishment of differentiated blood cells by hematopoietic stem and progenitor cells (HSCs and HPCs) throughout adulthood, a process termed hematopoiesis. Aging of the hematopoietic system is associated with a decline in adaptive immunity (5), an increased incidence of anemia (6), and a predisposition to myeloid neoplasms (7, 8). Hematopoietic stem cells (HSCs) exhibit an increase in immunophenotypically-defined cells with age, a decrease in their long-term reconstitution abilities, and a significant increase in myeloid-biased cell output at the expense of lymphopoiesis (9-15). The surroundings of HSCs in the bone marrow create a specific niche or microenvironment where HSCs nest that allows them to retain their unique characteristics and respond rapidly to external stimuli. Ageing is accompanied by reduced regenerative capacity of the organism affecting all systems, due to the progressive decline of stem cell functions. This includes blood and HSCs, which contributes to age-related haematological disorders, anemia, and immunosenescence, among others. While the cell-autonomous changes in the HSC that promote aging-related changes in hematopoiesis are more well defined, the contribution of the aged bone marrow (BM) microenvironment in promoting aged hematopoietic phenotypes is poorly understood (16, 17).

The Hematopoietic System

Hematopoiesis is the process of the generation of all differentiated blood cells in the organism, including red blood cells, platelets, innate immune cells, and lymphocytes; all found to fade in functionality in aged individuals. Hematopoiesis is carried out by a population of haematopoietic stem cells (HSCs), which in adults, reside mainly in the bone marrow. HSCs are self-renewing and give rise to all mature myeloid and lymphoid cell lineages. Although they are multipotent and self-renewing, HSCs are relatively quiescent in order to maintain an indefinite pool of HSCs (Passegué E, et al. J Exp Med. 2005 Dec. 5; 202(11):1599-611). In both humans and mice, advances in highly purified or single-cell transcriptomics and functional techniques challenge the past concept of cellular hierarchy in the haematopoietic system, where HSCs were thought to differentiate into a series of multilineage progenitors, culminating in unilineage progenitors that give rise to the variety of differentiated cells. Rather, adult HSCs seem to be a heterogeneous subset of mainly multipotent and unipotent progenitors affiliated to specific lineages, and the ratio of their skewing shifts when homeostasis is perturbed (Sanjuan-Pla, A. et al., Nature 2013, 502, 232-236; Pietras, E M et al., Cell Stem Cell 2015, 17, 35-46; Notta, F. et al., Science 2016, 351). HSC maintenance relies on the support from the microenvironment or niche, which tightly controls their function, fate, and numbers (Morrison, S. J., et al., Nature 2014, 505, 327-334). The HSC niche, a concept cued by Schofield already in 1978 (Schofield, R., Blood Cells 1978, 4, 7-25), is necessary to preserve the self-renewing potential of HSCs, which ensures the provision of newly differentiated blood cells whilst maintaining the HSC pool itself (Gomez-Lopez, S., et al., Cell. Mol. Life Sci. 2014, 71, 575-597). Extensive research on HSC niches composition shows that they are closely related to the vasculature in the bone marrow, with mainly endothelial, perivascular, and mesenchymal stromal cells secreting factors that support HSC maintenance (Crane, G. M., et al., Nat. Rev. Immunol. 2017, 17, 573-590). In this scenario, the effects of ageing on hematopoiesis may be the result of age-related alterations in all blood cell subsets, including HSCs and progenitors, as well as in the HSC niche.

The first description of murine HSC-enriched cells came about with the introduction of monoclonal antibodies and fluorescent activated cell sorting (FACS) technology (Spangrude G J, et al., Science. 1988 Jul. 1; 241(4861):58-62). Murine HSCs are commonly identified and isolated by differential expression of individual combinations of cell surface markers (Kiel M J, et al., Cell. 2005 Jul. 1; 121(7):1109-21). HSCs in adult mice are all Lineage (Lin)−, stem cell antigen-1 (Sca-1)+, and cKit+, often referred to as LSKs (Spangrude G J, et al., Science. 1988 Jul. 1; 241(4861):58-62). Murine LSKs, however, are diverse and can be further characterized with additional marker combinations. The most commonly used set of markers include the SLAM family of cell surface receptors that regulate the proliferation and activation of lymphocytes. They include CD150 (Slamf1), CD48 (Slamf2), CD229 (Slamf3), and CD244

(S1amf4) (Kiel M J, et al., Cell. 2005 Jul. 1; 121(7):1109-21; Oguro H, et al. Cell Stem Cell. 2013 Jul. 3; 13(1):102-16). These markers are differentially expressed among hematopoietic progenitors and correlate with progenitor primitiveness. This allows for adult LSKs to be subdivided into functionally distinct cell fractions containing hematopoietic stem and progenitor cells (HSPCs) and multipotent progenitors (MPPs) (Oguro H, et al. Cell Stem Cell. 2013 Jul. 3; 13(1):102-16). Even more precise isolation of HSCs can be achieved by selecting for different LSK subsets including Thy-1$^{low}$ (Morrison S J and Weissman I L Immunity. 1994 November; 1(8):661-73; Morrison S J, et al. Development. 1997 May; 124(10):1929-39), CD34$^-$ (Osawa M, et al., Science. 1996 Jul. 12; 273(5272):242-5), and Flt3$^-$ (Christensen J L and Weissman I L Proc Natl Acad Sci USA. 2001 Dec. 4; 98(25):14541-6) cells. Similar to murine HSCs, human HSCs can be divided into quiescent and self-renewing HSCs (Notta F, et al., Science. 2011 Jul. 8; 333(6039): 218-21). Human HSCs can be enriched using Lin−, CD34+, CD38−, Thy1.1+, CD45RA−, and in some cases CD49f+ (Notta F, et al., Science. 2011 Jul. 8; 333(6039):218-21).

The adult bone marrow also contains mesenchymal derived stem cells (MSCs) (Mendez-Ferrer S, et al., Nature. 2010 Aug. 12; 466(7308):829-34). MSCs regulate skeletal remodeling and are multipotent progenitor cells that can mature into osteoblasts (Zhu J, et al., Blood. 2007 May 1; 109(9):3706-12), adipocytes (Fazeli P K, et al. J Clin Endocrinol Metab. 2013 March; 98(3):935-45), myocytes, or chondrocytes. In vitro, MSCs can produce colony forming units of fibroblastoid colonies and differentiate into multiple lineages and support hematopoiesis (Kfoury Y and Scadden D T Cell Stem Cell. 2015 Mar. 5; 16(3):239-53). In vivo, the osteogenic lineage has been linked with HSC expansion (Calvi L M, et al., Nature. 2003 Oct. 23; 425(6960):841-6), while conditional ablation of osteolineage cells is associated with the loss of HSCs (Visnjic D, et al., Blood. 2004 May 1; 103(9):3258-64), demonstrating a functional role of osteolineage cells in hematopoiesis. Osteolineage cells also secrete cytokines vital for HSC regulation including granulocyte-colony stimulating factor (Taichman R S and Emerson S G, J Exp Med. 1994 May 1; 179(5):1677-82), thrombopoietin (Qian H, et al., Cell Stem Cell. 2007 Dec. 13; 1(6):671-84), angiopoietin-1 (Arai F, et al., Cell. 2004 Jul. 23; 118(2):149-61), and CXCL12 (Jung Y, et al., Bone. 2006 April; 38(4):497-508), and can be manipulated with activation of parathyroid hormone receptor 1 (Calvi L M, et al., Nature. 2003 Oct. 23; 425(6960):841-6) or bone morphogenetic protein (BMP) receptor type 1A (Zhang J, et al., Nature. 2003 Oct. 23; 425(6960):836-41) to increase HSC function.

MSCs are phenotypically heterogeneous (Churchman S M, et al., Arthritis Rheum. 2012 August; 64(8):2632-43; Harichandan A, S et al. Adv Biochem Eng Biotechnol. 2013; 1290:1-17). MSCs can be identified with platelet derived growth factor receptor α (PDGFRα), CD51, and/or Sca-1 (Morikawa S, et al., J Exp Med. 2009 Oct. 26; 206(11): 2483-96). Nestin-GFP+ cells in the murine bone marrow are also multipotent and self-renewing MSCs (Méndez-Ferrer S, et al., Nature. 2010 Aug. 12; 466(7308):829-34). MSCs can also be identified by other cell surface markers including CD105, CXCL12 abundant retricular (CAR) cells (Omatsu Y, et al., Immunity. 2010 Sep. 24; 33(3):387-99) and leptin receptor (LepR) perivascular cells (Mizoguchi T, et al., Dev Cell. 2014 May 12; 29(3):340-9).

More recently, the HSC hierarchy has been reconfigured to include megakaryocytes (Sanjuan-Pla A, et al., Nature. 2013 Oct. 10; 502(7470):232-6; Grover A, et al., Nat Commun. 2016 Mar. 24; 7:11075), particularly those with high cKit expression (Woolthuis C M and Park C Y, Blood. 2016 Mar. 10; 127(10):1242-8). Within the myeloid lineage of the classical HSC model, bipotent megakaryocyte-erythrocyte and granulocyte-macrophage progenitors produce unipotent progenitors that ultimately give rise to all mature blood cells. This model has been challenged with the idea that high cKit expressing megakaryocytes may come directly from HSCs (Heazlewood S Y, et al., Stem Cell Res. 2013 September; 11(2):782-92). Two recent studies provide functional evidence for megakaryocytes in the murine HSC niche during both steady state and stress hematopoiesis (Shin J Y, et al. J Exp Med. 2014 Feb. 10; 211(2):217-31) and in transplantation assays (Grinenko T, et al., J Exp Med. 2014 Feb. 10; 211(2):209-15). Additionally, in vivo megakaryocyte ablation results in a loss of HSC quiescence (Olson T S, et al., Blood. 2013 Jun. 27; 121(26):5238-49; Zhao M, et al., Nat Med. 2014 November; 20(11):1321-6), providing further evidence for a megakaryocytic contribution to the HSC niche.

HSCs Functional Changes with Age

Adult mammalian hematopoietic tissue homeostasis depends on the balance of HSC self-renewal with multilineage differentiation decisions (Spangrude G J, et al., Science. 1988 Jul. 1; 241(4861):58-62; Nibley W E and Spangrude G J, Bone Marrow Transplant. 1998 February; 21(4):345-54). Under steady state hematopoiesis, HSCs differentiate within the bone marrow (BM) into myeloid and lymphoid progenitors, leading to a balanced and tightly controlled production of both myeloid and lymphoid lineages. By contrast, older adults present a higher prevalence of anemia and compromised adaptive immunity due to reduced T and B-lymphocyte function caused by thymus involution and to a decreased number and/or function of aged lymphoid progenitors (Dorshkind K, et al., Nat Rev Immunol. 2009 January; 9(1):57-62; Geiger H and Rudolph K L, Trends Immunol. 2009 July; 30(7):360-5). This agingassociated impairment in immunity was initially anticipated to be a consequence of reduced numbers of HSCs.

The number of phenotypically defined HSCs in the mouse bone marrow increases by two to tenfold with age (Rossi D J, et al., Proc Natl Acad Sci USA. 2005 Jun. 28; 102(26): 9194-9; Beerman I, et al., Proc Natl Acad Sci USA. 2010 Mar. 23; 107(12):5465-70). This change in HSCs with age is highly strain dependent as aged C57BL/6 mice demonstrate two to threefold increases in HSCs (Sudo K, et al., J Exp Med. 2000 Nov. 6; 192(9):1273-80) while HSC numbers are slightly decreased in aged DBA/2 and Balb/c mice (de Haan G, et al., Blood. 1997 Mar. 1; 89(5):1543-50; Geiger H, et al., Blood. 2001 Nov. 15; 98(10):2966-72). This suggests that the self-renewal, differentiation, and quiescence of HSCs may be subject to significant genetic variation across mouse strains. Studies on human HSC aging also supports the view that phenotypic human HSC number (CD34+, CD38+, CD90+) increases with age (Pang W W, et al., Proc Natl Acad Sci USA. 2011 Dec. 13; 108(50):20012-7).

Even though murine HSCs increase with age, they appear to be dysfunctional (Sudo K, et al., J Exp Med. 2000 Nov. 6; 192(9):1273-80; Florian M C, et al., Cell Stem Cell. 2012 May 4; 10(5):520-30; Dykstra B, et al., J Exp Med. 2011 Dec. 19; 208(13):2691-703). In fact, per-cell self-renewing capacity declines with age (Janzen V, et al., Nature. 2006 Sep. 28; 443(7110):421-6). The mechanistic basis for the observed functional decline remains unknown due to variations in the quantification and purity of the HSCs assayed. It is suggested that aged HSCs are deficient in bone marrow engraftment such that when young and aged bone marrow cells are engrafted into a radioablated host and then retransplanted after twenty-four hours, the functional recovery from the recipient bone marrow is twofold lower for the aged HSCs (Liang Y, et al., Blood. 2005 Aug. 15; 106(4): 1479-87). This has been repeated in many other murine studies demonstrating that aged HSCs exhibit reduced repopulation capacity in competitive transplantation assays (Rossi D J, et al., Proc Natl Acad Sci USA. 2005 Jun. 28; 102(26):9194-9; Kamminga L M, et al., Stem Cells. 2005; 23(1):82-92; Morrison S J, et al. Nat Med. 1996 September; 2(9):1011-6). Similarly, HSCs isolated from the bone marrow of older human donors (>45 years of age) have reduced transplantation success in patients, indicating that human HSC self-renewal also decline with age (Kollman C, et al., Blood. 2001 Oct. 1; 98(7):2043-51).

Another age-associated phenotype of aged HSC donors and transplant recipients is their skewed differentiation towards the myeloid lineage (Lichtman M A and Rowe J M, Semin Oncol. 2004 April; 31(2):185-97; Gekas C and Graf T Blood. 2013 May 30; 121(22):4463-72). This phenomenon is consistent with the fact that pediatric hematopoietic malignancies are largely made up of lymphoid leukemias, while older individuals exhibit an observed increase in myelogenous diseases such as myelodysplastic syndrome (MDS) and acute myelogenous leukemia (AML) (Lichtman M A and Rowe J M, Semin Oncol. 2004 April; 31(2):185-97; Gekas C and Graf T Blood. 2013 May 30; 121(22):4463-72).

Aged HSCs also demonstrate enhanced mobilization from the bone marrow into the blood and reduced homing back to the bone marrow. Reports indicate that young and aged HSCs have distinct niche preferences in vivo, as suggested by the distinct anatomical positions of young and aged HSCs relative to the endosteum (Florian M C, et al., Cell Stem Cell. 2012 May 4; 10(5):520-30). Additionally, there is increased mobilization of aged HSCs to the blood in response to chemotherapy and cytokines compared to young HSCs (Florian M C, et al., Cell Stem Cell. 2012 May 4; 10(5):520-30; Dykstra B, et al., J Exp Med. 2011 Dec. 19; 208(13):2691-703. Aged HSCs also have impaired adhesive properties (Liang Y, et al., Blood. 2005 Aug. 15; 106(4): 1479-87; Geiger H, et al., Cell Cycle. 2007 Apr. 15; 6(8): 884-7; Xing Z, et al., Blood. 2006 Oct. 1; 108(7):2190-7.).

Hallmarks of Aged HSCs

Aging within the hematopoietic system comprises a set of distinct changes, including an increase in the frequency of myeloid cells generated linked to an increase in myeloid-related leukemia, a decrease in the output of lymphoid cells (primarily B-cells) and a reduced regenerative capacity of hematopoiesis upon stress and a decrease in the function of both the innate and adaptive branches of the immune response (Chambers S M, et al., PLoS Biol. 2007 August; 5(8):e201; Beerman I, et al., Cell Stem Cell. 2013 Apr. 4; 12(4):413-25; Miller J P and Allman D, Semin Immunol. 2005 October; 17(5):321-9). One underlying cellular cause of aging of the hematopoietic system is aging of hematopoietic stem cells (HSCs). While upon aging the number of phenotypic HSCs increases, their regenerative potential (as determined in serial transplantation assays) decreases (Dykstra B, et al., J Exp Med. 2011 Dec. 19; 208(13):2691-703). Aged HSCs differentiate preferentially into myeloid cells and show diminished support of the B-cell lineage. Loss of a polar distribution of polarity proteins like Cdc42 and Scribble but also tubulin in the cytoplasm, and loss of the polar distribution of the acetylated form of the epigenetic marker H4K16 in the nucleus, which are caused by an elevated activity of the small RhoGTPAse Cdc42 in aged HSCs, are additional recently identified hallmarks of aged HSCs (Florian M C, et al., Cell Stem Cell. 2012 May 4; 10(5):520-30; Florian M C and Geiger H, Stem Cells. 2010 September; 28(9):1623-9). Aged HSCs also present with changes in their epigenome and altered gene expression profiles (Chambers S M, et al., PLoS Biol. 2007 August; 5(8):e201; Beerman I, et al., Cell Stem Cell. 2013 Apr. 4; 12(4):413-25). Indeed, genome-wide expression studies comparing HSCs from young and old mice indicated that in aged HSCs, expression of genes involved in myeloid development was increased whereas expression of gene involved in lymphopoiesis was decreased; moreover also gene sets associated with inflammation, stress response and senescence were increased in aged HSC like Clusterin, Platelet-selectin, Cyclooxygenase 2, Toll-like receptor 4 and the Heat shock proteins 5 and 8. (Chambers S M, et al., PLoS Biol. 2007 August; 5(8):e201; Rossi D J, et al., Proc Natl Acad Sci USA. 2005 Jun. 28; 102(26):9194-9).

Changes in clonality in hematopoiesis upon aging, characterized by an accumulation of a predominantly myeloid-dominant HSC population, demonstrated that individual old HSCs are functionally inferior to their young counterparts in multiple phenotypes, including a lower functional frequency in vitro and in vivo, a delayed proliferation response in stromal co-cultures, a reduced efficiency for short-term BM homing, and a reduced long-term in vivo self-renewal activity (Dykstra B, et al., J Exp Med. 2011 Dec. 19; 208(13): 2691-703.).

Mechanisms of HSC Aging

Mechanisms of HSC aging involve distinct cell-intrinsic and cell-extrinsic regulatory pathways. In addition to altered transcriptional landscapes and abnormal transduction of signaling cascades that is observed in many aging processes, new concepts related to epigenetic modifications, cytoskeletal polarity, cellular senescence, and clonal selection are also observed with aging.

Cell-Intrinsic Mechanisms

Altered Transcriptional Landscapes

The concept of successful rejuvenation approaches was supported by Shinya Yamanaka's lab, which in 2006 established the induced pluripotent stem cell (iPSCs) technology in which the introduction of four specific genes encoding transcription factors could convert adult somatic cells into pluripotent stem cells (Takahashi K, et al, Cell. 2006 Aug. 25; 126(4):663-76.). This discovery suggested that by targeting the epigenetic landscape differentiation can be reverted, which implies that also aging, if primarily driven be epigenetic mechanism, might be reversible. Wahlestedt et al, by reprogramming old HSC into iPSCs and then re-differentiating them into HSCs, demonstrated that the resulting HSCs were functionally similar to young HSCs, thus actually experimentally demonstrating that HSC aging is reversible by epigenetic reprogramming (Wahlestedt M, et al., Blood. 2013 May 23; 121(21):4257-64). Table 1, below, summarizes published data in which intrinsic mechanisms of aging were targeted both genetically or pharmacologically to achieve at least in part a rejuvenation of the one or more functions of aged HSCs.

TABLE 1

| Target proteins | Type of intervention | Rejuvenation phenotype(s) | Reference |
|---|---|---|---|
| Satb1 | genetic | Overexpression enhances lymphoid progeny | Satoh Y, et al. Immunity. 2013 Jun. 27; 38(6): 1105-15 |

TABLE 1-continued

| Target proteins | Type of intervention | Rejuvenation phenotype(s) | Reference |
|---|---|---|---|
| Per2 | genetic | Deletion attenuates lymphoid/myeloid skewing | Wang J, et al. Nat Cell Biol. 2016 May; 18(5): 480-90 |
| Sirt3 | genetic | Overexpression decreases ROS production | Brown K, et al. Cell Rep. 2013 Feb. 21; 3(2): 319-27. |
| Sirt7 | genetic | Overexpression reduces PFSmt | Mohrin M, et al. Science. 2015 Mar. 20; 347(6228): 1374-7 |
| mTOR | pharmacologic | Inhibition increases life span | Chen C, et al. 2009; 2(98): ra75 |
| Prolonged fasting | pharmacologic | Reduces the frequency of myeloid-biased HSCs | Cheng C-W, et al. Cell Stem Cell. 2014 Jun. 5; 14(6): 810-23 |
| Cdc42 | pharmacologic | Inhibition enhances competitive repopulation | Florian M C, et al. Cell Stem Cell. 2012 May 4; 10(5): 520-30 |
| BCL-xL | pharmacologic | Inhibition depletes senescent HSCs in the BM | Chang J, et al. Nat Med. 2016 Jan; 22(1): 78-83 |

Clonality

The concept of clonality shifts is a new trademark of HSC aging and is associated with an increased risk of hematologic cancer (Jaiswal S, et al., N Engl J Med. 2014 Dec. 25; 371(26):2488-98). HSCs are considered to be equipotent in their contribution to hematopoiesis with multiple clones contributing to hematopoiesis throughout life. Higher levels of clonality, an indicator that only a few clones actively contribute to blood cell production, are observed upon aging [132-134]. Sun et al. demonstrate that multiple clones contribute to hematopoiesis during development, but, later in adulthood, long-term HSCs—as opposed to HSCs—contributed to hematopoiesis (Sun J, et al., Nature. 2014 Oct. 16; 514(7522):322-7). Using limiting dilution transplantation experiments, Bush et al. similarly demonstrated that short-term HSCs increasingly contribute to hematopoiesis during aging (Busch K, et al., Nature. 2015 Feb. 26; 518(7540): 542-6). By means of computational models, it is implied that the aged-associated myeloid bias may arise from reduced multipotent progenitor differentiation to common lymphoid progenitors rather than a change in the HSC pool (Busch K, et al., Nature. 2015 Feb. 26; 518(7540):542-6). Using high-throughput sequencing to follow the clonal contribution to hematopoiesis, Verovskaya et al. demonstrated that young mice have fewer active HSC clones that readily self-renew, but aged mice have more active HSC clones with less self-renewal capacity (Verovskaya E, et al., Blood. 2013 Jul. 25; 122(4):523-32).

Cell-Extrinsic Mechanisms

The bone marrow niche interacts with HSCs to orchestrate their survival, proliferation, self-renewal, and differentiation (Calvi L M, et al., Nature. 2003 Oct. 23; 425(6960): 841-6; Katayama Y, et al., Cell. 2006 Jan. 27; 124(2):407-21; Nakamura Y, et al., Blood. 2010 Sep. 2; 116(9):1422-32). HSC niches are composed of many cell types and their fate are additionally regulated by many secreted factors. Age-induced alterations in niche composition include decreased bone formation, increased adipogenesis, and changes in extracellular matrix components. Skewing of aged HSCs towards myeloid differentiation was recently linked to increased secretion of the pro-inflammatory CC-chemokine ligand 5 (CCL5; also known as RANTES) in aged stroma (Ergen A V, et al., Blood. 2012 Mar. 15; 119(11):2500-9). This niche-induced skewing of HSC differentiation may promote disease progression in acute myeloid leukemia (Vas V, et al., PLoS One. 2012; 7(2): e31523 and myelodysplastic syndrome (Balderman S R, et al., Blood. 2016 Feb. 4; 127(5):616-25). CXC-chemokine ligand 12 (CXCL12) is another critical chemokine in the bone marrow niche. It is a chemoattractant for HSCs, regulating their localization, turnover, and mobilization from the bone marrow. With age, there is increased fat content in the bone marrow attributed to the differentiation of bone marrow mesenchymal stem cells into adipocytes. This increase in fat content is inversely correlated with CXCL12 plasma levels in the elderly and directly correlated with the increased HSC numbers also observed in the elderly (Tuljapurkar S R, et al., J Anat. 2011 November; 219(5): 574-81).

Together, these studies demonstrate that alterations in niche composition, niche interactions, and diminished or abnormal communication between HSCs and their environment may drive HSC aging.

HSC Rejuvenation

The concept of stem cell rejuvenation is tightly linked to the finding that differentiated cells can be reprogrammed into induced pluripotent stem cells (iPSCs). This suggests that the differentiated, and perhaps aged, state, might also be reversible by changing the epigenetic landscape. Wahlestedt et al demonstrated that iPSCs generated from aged murine HSCs that were re-differentiated back into HSCs were functionally highly similar to young HSCs, suggesting that HSC aging might be driven, at least in part, by reversible epigenetic reprogramming (Wahlestedt M, et al., Blood. 2013 May 23; 121(21):4257-64). Additional evidence that stem cell rejuvenation is possible has emerged from mouse caloric restriction studies. Caloric restriction extends the life span of multiple organisms, including worms, flies, and mice (Koubova J and Guarente L, Genes Dev. 2003 Feb. 1; 17(3):313-21). Prolonged fasting has been found to rejuvenate the aging-associated myeloid differentiation bias as well as the reduced long-term repopulation capacity of aged mouse HSCs. Such rejuvenation has been mechanistically attributed to reduced IGF-1 signaling and restored youthful levels of intrinsic HSC nutrient sensing (Cheng C W, et al., Cell Stem Cell. 2014 Jun. 5; 14(6):810-23). Sirtuins, mitochondrial histone deacetylases, mediate caloric restriction effects in lower organisms such as *S.cerevisiae, C.elegans* and *D. melanogaster* (Guarente L, Kenyon C Nature. 2000 Nov. 9; 408(6809):255-62). In particular, Sirt3, a mammalian sirtuin that regulates the mitochondrial acetylation landscape, has been found to be reduced in aged mouse HSCs; furthermore, Sirt3 overexpression has been reported to rescue aging-associated HSC functional defects (Brown K, et al., Cell Rep. 2013 Feb. 21; 3(2):319-27). Expression of Sirt7 has also been shown to be decreased in aged murine HSCs, while its overexpression has been found to increase HSC reconstitution capacity and to reduce the aged HSC myeloid bias (Mohrin M, et al., Science. 2015 Mar. 20; 347(6228):1374-7).

The expression of another nutrient-sensing protein, the Mammalian target of rapamycin (mTOR) has been reported as elevated in aged murine HSCs (Chen C, et al., Sci Signal. 2009 Nov. 24; 2(98):ra75) and treatment with the mTOR inhibitor rapamycin has been found to reverse the agingassociated increase in HSC numbers, restoring reconstitution potential and self-renewal (Chen C, et al., Sci Signal. 2009). Transient treatment of aged mice with rapamycin was also shown to improve the vaccination response to influenza virus (Chen C, et al., Sci Signal. 2009), implying that improved lymphopoiesis and adaptive immunity ensue in response to mTOR inhibition.

Another example of successful HSC rejuvenation comes from studies on a specific inhibitor of Cdc42 activity (CASIN) (Florian M C, et al., Cell Stem Cell. 2012 May 4; 10(5):520-30). As discussed previously, CASIN treatment ex vivo can restore aged mouse HSC phenotypes by both regulating Cdc42 activity and epigenetic reprogramming by elevating H4K16Ac levels to those of young cells, again emphasizing the strong link between epigenetic reprogramming and stem cell rejuvenation. Further supporting the role of epigenetic reprogramming in HSC rejuvenation, Satoh et al identified that aging-associated immunosenescence could be linked to a reduced expression of Satb1, an epigenetic regulator of lymphoid progenitors (Satoh Y, et al., Immunity. 2013 Jun. 27; 38(6):1105-15). Moreover, overexpression of Satb 1 via epigenetic reprogramming could rescue aged HSC immunosenescence (Satoh Y, et al., Immunity. 2013 Jun. 27; 38(6):1105-15). Thus, multiple successful approaches currently share a common underlying theme; epigenetic reprogramming appears to be a central mechanistic contributor to HSC rejuvenation. However, in general, rejuvenating agents might not be able to revert DNA mutations in HSCs associated with clonality upon aging.

A need remains to develop novel approaches to ameliorate or even reverse aging-associated hallmarks of aged HSCs. The described invention is based on the idea that aged ECs are sufficient to promote aging of young HSCs, and that the infusion of young ECs can be exploited to improve age-related hematopoietic deficiencies. The described invention provides cellular therapies that can serve as adjuvant modalities to enhance hematopoietic recovery, particularly in the elderly population following myelosuppressive treatments, to ultimately protect patients from severe morbidities and mortality associated with the treatment of hematological disorders.

SUMMARY OF THE INVENTION

According to one aspect, the described invention provides a method for enhancing the engraftment capabilities of hematopoietic cells, comprising providing a hematopoietic cell population; contacting the hematopoietic cell population with BM endothelial cells; incubating the hematopoietic cell population and BM endothelial cells for a period of time to produce a mixed hematopoietic cell/BM endothelial cell population; and transplanting the hematopoietic cell/BM endothelial cell population into a subject in need thereof, wherein engraftment of the hematopoietic cell population is increased in the subject, compared to a control hematopoietic cell population not contacted with endothelial cells. According to one embodiment, the hematopoietic cell population comprises at least one of hematopoietic stem cells (HSCs), hematopoietic progenitor cells (HPCs), and CD34+ cells. According to one embodiment, the hematopoietic cell population is a purified population of HSCs. According to one embodiment, the HSCs are derived from donor bone marrow or cord blood. According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as VECAD$^+$CD31$^+$Lineage$^-$CD45$^-$TER119$^-$ cells. According to one embodiment, the BM endothelial cells are characterized by expression of miR-344a, miR-133b-3p, miR-294, miR-423-3p, or miR-872-3p. According to one embodiment, the BM endothelial cells are derived from an individual 35 years of age or less. According to one embodiment, the BM endothelial cells are derived from an individual 30 years of age or less. According to one embodiment, the BM endothelial cells are derived from a donor 25 years of age or less. According to one embodiment, the BM endothelial cells are derived from donor bone marrow or cord blood. According to one embodiment, reconstitution, homing and/or proliferation of the hematopoietic cell population is increased in vivo, compared to population not contacted with BM endothelial cells. According to one embodiment, the hematopoietic cell/BM endothelial cell population is treated with an additional therapeutic agent prior to, concurrently with, or after transplantation.

According to another aspect, the disclosure provides a method for enhancing engraftment of hematopoietic stem cells in a subject in need thereof, comprising infusing or co-infusing one or more of: a population of BM endothelial cells, a population of hematopoietic cells, or a mixed hematopoietic cell/BM endothelial cell population to the subject, thereby enhancing engraftment of hematopoietic stem cells. According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as VECAD$^+$CD31$^+$Lineage$^-$CD45$^-$TER119$^-$ cells. According to one embodiment, the BM endothelial cells are characterized by expression of miR-344a, miR-133b-3p, miR-294, miR-423-3p, or miR-872-3p.

According to another aspect, the disclosure provides a method of promoting hematopoietic recovery in a subject undergoing a myelosuppressive regimen, comprising infusing or co-infusing one or more of a population of BM endothelial cells (ECs), a population of hematopoietic cells, or a mixed hematopoietic cell/BM endothelial cell population to the subject, thereby promoting hematopoietic recovery in the subject. According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as VECAD$^+$CD31$^+$Lineage$^-$CD45$^-$TER119$^-$ cells. According to one embodiment, the BM endothelial cells are characterized by expression of miR-344a, miR-133b-3p, miR-294, miR-423-3p, or miR-872-3p.

According to another aspect, the disclosure provides a method of treating a subject who has received a hematopoietic stem cell transplant comprising hematopoietic stem cells and/or progenitor cells, comprising infusing or co-infusing one or more of: a population of BM endothelial cells (ECs), a population of hematopoietic cells, or a mixed hematopoietic cell/BM endothelial cell population to the subject, thereby treating the subject. According to one embodiment of the aspects and embodiments herein, the hematopoietic cell population comprises at least one of: hematopoietic stem cells (HSCs), hematopoietic progenitor cells (HPCs), and CD34+ cells. According to one embodiment, the hematopoietic cell population is a purified population of HSCs. According to one embodiment, the HSCs are derived from donor bone marrow or cord blood. According to one embodiment of the aspects and embodiments herein, the population of BM endothelial cells and the population of hematopoietic cells are administered simultaneously or sequentially. According to one embodiment of the aspects and embodiments herein, the BM endothelial cells are derived from an individual 35 years of age or less. According to one embodiment of the aspects and embodiments herein, the BM endothelial cells are derived from an individual 30 years of age or less. According to one embodiment of the aspects and embodiments herein, the BM endothelial cells are derived from a donor 25 years of age or less. According to one embodiment of the aspects and embodiments herein, the BM endothelial cells are derived from donor bone marrow or cord blood. According to one embodiment of the aspects and embodiments herein, the subject is 65 years or more in age. According to one embodiment of the aspects and embodiments herein, the subject has bone marrow disease. According to one embodiment of the aspects and embodiments herein, the bone marrow disease is selected from the group consisting of leukemia, a defect of the blood cell compartment, and a bone marrow disease induced by chemotherapy or irradiation. According to one embodiment of the aspects and embodiments herein, the subject has cancer. According to one embodiment of the aspects and embodiments herein, the subject has an autoimmune disorder. According to one embodiment of the aspects and embodiments herein, the subject has previously been treated with a myelosuppressive regimen; the subject is currently being treated with a myelosuppresive regimen; or the subject will undergo treatment with a myelosuppressive regimen. According to one embodiment, the myelosuppressive regimen comprises chemotherapy or radiation.

According to another aspect, the disclosure provides a method of reversing the aging of hematopoietic stem cells, comprising contacting the hematopoietic stem cells with BM endothelial cells, thereby reversing the aging of the hematopoietic stem cells. According to one embodiment, the hematopoietic stem cells exhibit improved performance in an assay selected from the group consisting of HSC engraftment, bone marrow reconstitution, and competitive transplantation. According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as VECAD$^+$CD31$^+$Lineage$^-$CD45$^-$TER119$^-$ cells. According to one embodiment, the endothelial cells are characterized by expression of miR-344a, miR-133b-3p, miR-294, miR-423-3p, or miR-872-3p.

According to another aspect, the disclosure provides a method of preventing the aging of hematopoietic stem cells, comprising contacting the hematopoietic stem cells with BM endothelial cells, thereby preventing the aging of the hematopoietic stem cells. In one embodiment, aging of the stem cell is delayed. According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as VECAD$^+$CD31$^+$Lineage$^-$CD45$^-$TER119$^-$ cells. According to one embodiment, the endothelial cells are characterized by expression of miR-344a, miR-133b-3p, miR-294, miR-423-3p, or miR-872-3p.

According to another aspect, the disclosure provides a method for promoting hematopoietic stem cell maintenance, comprising contacting the hematopoietic stem cells with BM endothelial cells, wherein the stem cell continues to self-renew. According to one embodiment of the aspects and embodiments herein, the hematopoietic stem cells are aged hematopoietic stem cells. According to one embodiment of the aspects and embodiments herein, the hematopoietic stem cells are in an animal. According to one embodiment, the animal is a human. According to one embodiment of the aspects and embodiments herein, the BM endothelial cells are derived from an individual 35 years of age or less. According to one embodiment of the aspects and embodiments herein, the BM endothelial cells are derived from an individual 30 years of age or less. According to one embodiment of the aspects and embodiments herein, the BM endothelial cells are derived from a donor 25 years of age or less. According to one embodiment of the aspects and embodiments herein, the BM endothelial cells are derived from donor bone marrow or cord blood. According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as VECAD$^+$CD31$^+$Lineage$^-$CD45$^-$TER119$^-$ cells. According to one embodiment, the endothelial cells are characterized by expression of miR-344a, miR-133b-3p, miR-294, miR-423-3p, or miR-872-3p. According to one embodiment of the aspects and embodiments herein, the BM endothelial cells are treated with an additional therapeutic agent prior to, concurrently with, or after transplantation.

According to another aspect, the disclosure features a method of preparing an endothelial cell vascular niche effective for maintaining functional HSCs, the method comprising providing a hematopoietic cell population; contacting the hematopoietic cell population with BM endothelial cells; and incubating the hematopoietic cell population and endothelial cells for a period of time to produce a mixed hematopoietic cell/endothelial cell population; wherein the functional HSCs are characterized by one or more of (i) improved performance in an HSC engraftment assay; (ii) improved bone marrow reconstitution; (iv) improved hematopoietic recovery; (v) increased repopulating activity; and (vi) improved self-renewal, compared to a control hematopoietic stem cell population. According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as VECAD$^+$CD31$^+$Lineage$^-$CD45$^-$TER119$^-$ cells. According to one embodiment, the endothelial cells are characterized by expression of miR-344a, miR-133b-3p, miR-294, miR-423-3p, or miR-872-3p.

In one embodiment, the hematopoietic cell population is a purified population of HSCs. In one embodiment, the HSCs are derived from donor bone marrow or cord blood. In one embodiment, the control hematopoietic stem cell population comprises aged HSCs.

According to another aspect, the disclosure provides a hematopoietic stem cell population produced by the methods described according to the aspects and embodiments herein.

According to another aspect, the disclosure provides a preserved and rejuvenated hematopoietic stem cell population, wherein the population is characterized by one or more of (i) improved performance in an HSC engraftment assay; (ii) improved bone marrow reconstitution; (iv) improved hematopoietic recovery; (v) increased repopulating activity; and (vi) improved self-renewal, compared to a control hematopoietic stem cell population.

In one embodiment, the control hematopoietic stem cell population comprises aged HSCs.

According to one aspect, the described invention provides a method of promoting hematopoietic recovery in an elderly (>65 years of age) human patient undergoing a myelosuppressive regimen, comprising of transplanting hematopoietic stem cell (HSC)-supportive endothelial cells (ECs) to the patient. According to one embodiment, the ECs are derived from a donor under the age of 35, 30, or 25. According to one embodiment, the ECs are purified from the bone marrow of the donor. According to another embodiment, the ECS are isolated from human umbilical vein (HUVECs). According to one embodiment, the ECs are transplanted before, during, or after the myelosuppressive regimen. According to one embodiment, the myelosuppressive regimen comprises chemotherapy or radiation. According to another embodiment, the patient is a cancer patient or any patient with hematopoietic failure syndromes. According to one embodiment, the patient is over the age of 65.

According to another aspect, the described invention provides a method of promoting aged HSC (>65 years of age) engraftment in a human patient, comprising transplanting HSCs and HSC-supportive ECs. According to one embodiment, the ECs are derived from a donor under the age of 35, 30, or 25. According to one embodiment, the ECs are purified from the bone marrow of the donor. According to one embodiment, the ECS are isolated from human umbilical vein (HUVECs). According to another embodiment, the ECs are transplanted before, simultaneously with, and/or after the transplantation of the HSCs. According to one embodiment, the aged HSCs (>65 years of age) and ECs have been in co-cultured prior to the transplantation. According to a further embodiment, the patient has a damaged or defective bone marrow or immune system, as a result of, for example, cancer or autoimmune disorder, such as, multiple myeloma, Non-Hodgkin lymphoma, Hodgkin disease, acute myeloid leukemia, acute lymphoblastic leukemia, chronic myeloid leukemia, chronic lymphocytic leukemia, myeloproliferative disorders, myelodysplastic syndromes, aplastic anemia, pure red cell aplasia, paroxysmal nocturnal hemoglobinuria, Fanconi Anemia, thalassemia major, sickle cell anemia, severe combined immunodeficiency, neuroblastoma, germ cell tumors, system lupus erythematosus, systemic sclerosis, amyloidosis, Wiskott-Aldrich syndrome, hemophagocytic lymphohistiocytosis, inborn errors of metabolism, epidermolysis bullosa, severe congenital neutropenia, Schwachman-Diamond syndrome, Diamond-Blackfan anemia, and leukocyte adhesion deficiency. According to one embodiment, the patient is over the age of 65.

According to another aspect, the disclosure provides a method of promoting HSC engraftment in a human patient over the age of 65, comprising co-culturing HSCs with HSC-supportive ECs prior to transplantation of the HSCs to the patient. According to one embodiment, after co-culturing, the HSCs are transplanted to the patient with the ECs.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1H show aged bone marrow vasculature displays functional alterations in vivo. (FIG. 1A) Representative longitudinal and inset images of femurs intravitally-labeled with a vascular-specific VECAD (VE Cadherin) antibody (red) demonstrating morphological alterations in aged vasculature (dashed lines demarcate cortical bone). Longitudinal and inset scale bar=100 μm and 50 μm, respectively. (FIG. 1B-FIG. 1C) Analysis of bone marrow (BM) vascular leakiness in young and aged femurs. (FIG. 1B) Quantification of Evan's Blue Dye (EBD) extravasation (n=5 mice/cohort). (FIG. 1C) Representative femurs injected with EBD. Non-injected controls were used to determine baselines (n=5 mice/cohort). (FIG. 1D-FIG. 1E) Frequency of recoverable (FIG. 1D) VECAD$^+$CD31$^+$CD45$^-$TER119$^-$ BM endothelial cells (ECs) and (FIG. 1E) VECAD$^-$CD31$^-$CD45$^-$TER119$^-$ stroma in young and aged femurs (n=5 mice/cohort). (FIG. 1F) Quantification of mean fluorescence intensity (MFI) and representative histogram of reactive oxygen species (ROS) in VECAD$^+$CD31$^+$CD45" endothelial cells (ECs) from young and aged femurs demonstrating an increase in ROS in aged ECs (n=3 mice/cohort). (FIG. 1G) MFI quantification and representative histogram of pimonidazole adducts as detected by an anti-pimonidazole antibody (HypoxyProbe) in VECAD$^+$CD31$^+$CD45$^-$ endothelial cells (ECs) from young and aged femurs, demonstrating an increased hypoxia state in aged ECs (n=3 mice/cohort). (FIG. 1H) Representative immunofluorescence images of HypoxyProbe stained young and aged femurs, demonstrating local changes in hypoxia. Scale bar=50 μm. Error bars represent sample mean±SEM. Comparisons using two-tailed unpaired Student's t-test was performed to determine significance. * P<0.05;  P<0.01; * P<0.001.

FIGS. 2A-2K show characterization of cultured endothelial cells from aged mice. (FIG. 2A) Representative phase contrast and immunofluorescence images of cultured bone-marrow derived endothelial cells (ECs) from young and aged mice. Phase scale bar=200 μm. Immunofluorescence scale bar=50 μm. (FIG. 2B) Representative flow plots of cultured ECs stained for VECAD$^+$CD31$^+$ demonstrating highly-purified endothelial populations. (FIG. 2C-FIG. 2E) Analysis of elasticity in cultured young and aged ECs using Atomic Force Microscopy (AFM) demonstrating an increase in aged EC stiffness. (FIG. 2C) Representative reconstructed images of EC monolayers. (FIG. 2D) Box plots of the median stiffness in cultured young and aged ECs (n=3 biological replicates). (FIG. 2E) Normalized relative EC stiffness (n=3 biological replicates). (FIG. 2F-FIG. 2G) Proliferation status of cultured young and aged ECs. (FIG.

2F) Representative histograms of Edu incorporation following cell cycle synchronization. (FIG. 2G) Quantification of Edu incorporation demonstrating an early inhibition of cell cycle entry into S-phase in aged ECs that is resolved by 24 hours (n=3 biological replicates). (FIG. 2H) Quantification of senescence-associated Beta-Galactosidase (SA β-Gal) activity in young and aged ECs (n=3 biological replicates). (FIG. 2I-FIG. 2J) In vitro scratch wound healing assay demonstrating a functional delay in cell migration in aged ECs. (FIG. 2I) Representative phase contrast images (dashed lines demarcate initial scratch wound). Phase scale bar=400 μm. (FIG. 2J) Quantification of EC wound healing (n=3 biological replicates). (FIG. 2K) Normalized gene expression in cultured young and aged ECs (n=3 biological replicates). Unless noted, significance was determine using a two-tailed unpaired Student's t-test with error bars representing the sample mean±SEM. Non-parametric one-sided Wilcoxon Rank Sum test was used to compare (FIG. 2D) median endothelial stiffness. Data is presented as a box plot with whiskers representing ±1.5 interquartile range (IQR). Relative endothelial stiffness (FIG. 2E) is normalized to young ECs and presented as a 95% confidence interval. * $P<0.05$;  $P<0.01$; * $P<0.001$; n.s.=not significant.

FIGS. 3A-3F show aged endothelial cells are sufficient to induce aged hematopoietic phenotypes. (FIG. 3A-FIG. 3B) Quantification of hematopoietic expansion by flow cytometry. (FIG. 3A) Total phenotypic $CD45^+$ hematopoietic cell and (FIG. 3B) $CD45^+lineage^-cKIT^+SCA1^+$ hematopoietic stem and progenitor cells (HSPCs) (n=3 independent co-cultures). (FIG. 3C) Quantification of $CD45.2^+$ donor chimerism in the peripheral blood four months post-transplantation, as measured by flow cytometry (n=5 mice/cohort). Results demonstrate the ability of young ECs to restore hematopoietic engraftment of HSPCs following co-culture, while aged ECs impair young hematopoietic engraftment relative to age-matched co-culture controls. Un-manipulated pre-expansion whole bone marrow (WBM) from young or aged mice were competitively transplanted into lethally-irradiated recipients to confirm age-dependent hematopoietic reconstitution phenotypes (n=5 mice/cohort). (FIG. 3D-FIG. 3F) Quantification of donor-derived $lineage^+$ hematopoietic repopulation four months post-transplantation. (FIG. 3D) Frequency of $CD11B^+GR1^+$ myeloid cells, (FIG. 3E) $B220^+CD19^+$ B cells, and (FIG. 3F) $CD8^+$ (black)/$CD4^+$ (grey) T cells populations in peripheral blood were determined by flow cytometry. Young HSPCs co-cultured with aged ECs acquire myeloid-biased engraftment at the expense of lymphopoiesis, while young ECs are unable to reverse myeloid-bias in aged HSPC expansions. Error bars represent sample mean±SEM. Two-tailed unpaired Student's t-tests of like groupings were performed to determine significance (* $P<0.05$;  $P<0.01$; * $P<0.001$).

(FIG. 4A) Schematic of endothelial cell (EC) infusion strategy. (FIG. 4B-FIG. 4C) Time-course of peripheral blood (PB) recovery of (FIG. 4B) young or (FIG. 4C) aged mice following irradiation (650 Rads) and either young EC, aged EC, or PBS vehicle control infusion (n=5 mice/cohort). Results demonstrate the myeloprotective effect of young EC transplantation (Tpx) following hematopoietic insult in both young and aged recipients, while aged EC Tpx is indistinguishable from PBS vehicle controls. (FIG. 4D-FIG. 4F) Quantification of $CD45.2^+$ donor chimerism and multi-lineage engraftment in PB four months post-donor WBM transplantation, as measured by flow cytometry (n=5 mice/cohort). (FIG. 4D) Unmanipulated steady state young and aged WBM was competitively transplanted to confirm reduced $CD45.2^+$ hematopoietic engraftment and phenotypic $CD11B^+/GR1^+$ myeloid bias in aged WBM Tpx cohort (n=5 mice/cohort). (FIG. 4E) Young and (FIG. 4F) aged donors infused with young ECs demonstrate an increase in hematopoietic engraftment, while supporting an increase in $B220^+$ and $CD3^+$ lymphoid reconstitution. Error bars represent sample mean±SEM. Comparisons using two-tailed unpaired Student's t-tests at individual time points were performed to determine significance (* $P<0.05$;  $P<0.01$; * $P<0.001$). Steady state and PBS controls are included as recovery reference points and are not incorporated in statistical analysis.

FIGS. 5A-5H show co-infusion of young endothelium enhances bone marrow transplantation. (FIG. 5A-FIG. 5B) Survival curves of mice transplanted (Tpx) with $10^5$ WBM cells from either (FIG. 5A) young or (FIG. 5B) aged animals demonstrating an increase in overall survival in WBM cohorts co-infused with endothelial cells (ECs) (n=10 mice/cohort). Note: Panel A-B share the same figure legend and steady state, PBS, and EC alone controls. Survival curve significance between WBM and WBM+EC cohorts was calculated using the Log-Rank test. (FIG. 5C-FIG. 5D) Time-course of hematopoietic recovery in the peripheral blood of recipient mice co-infused with $10^5$ young or aged WBM with or without young endothelium. EC co-infused animals display a significant increase in hematopoietic recovery (n=10 mice/cohort). (FIG. 5E-FIG. 5F) Quantification of colony-forming units-spleen (CFU-S) in mice transplanted with $10^5$ WBM from (FIG. 5E) young or (FIG. 5F) aged donors with or without young endothelium demonstrating an increase in hematopoietic progenitor activity in cohorts co-infused with ECs. CFU-S were scored eight days post-irradiation (n>5 mice/cohort). (FIG. 5G-FIG. 5H) A log-fraction plot of limiting dilution analysis demonstrating the frequency of long-term multi-lineage repopulation of WBM from (FIG. 5G) young or (FIG. 5H) aged mice transplanted into lethally-irradiated recipients and co-infused with or without young ECs (n=10 mice/cohort). Dashed lines indicated 95% confidence intervals. Stem cell frequency and significance was determined using Extreme Limiting Dilution Analysis (ELDA). Unless noted, error bars represent sample mean±SEM. Unpaired two-tailed Student's t-test was performed to determine significance (* $P<0.05$;  $P<0.01$; * $P<0.001$). Steady state, PBS, and EC alone controls are reference points and are not included in statistical analysis.

FIG. 6A-FIG. 6F show endothelial cell co-infusion radioprotects the bone marrow microenvironment. Lethally-irradiated (950 Rads) mice were co-infused with either $10^5$ young or aged whole bone marrow (WBM) and $5\times10^5$ young bone marrow (BM) endothelial cells (ECs). (FIG. 6A) Representative Hematoxylin and Eosin (H&E) stained longitudinal femur sections from co-infused mice seven days post-irradiation (n=10 mice/cohort; 100× magnification). (FIG. 6B) Representative images of damaged $VEGFR3^+$ femoral vessels, including Type I hemorrhagic (asterisk), Type I discontinuous (red arrow), and Type II regressed (blue arrow) seven days post-irradiation, demonstrating the radioprotection of the vascular niche (n=10 mice/cohort; 200× magnification). Sections are counter-stained with Hematoxylin. (FIG. 6C-FIG. 6D) Quantification of total bone marrow (BM) $CD45^+$ cells demonstrating mitigation of pan-hematopoietic injury in young or aged WBM-young EC co-infused cohorts (n=10 mice/cohort; related to panel A). (FIG. 6E-FIG. 6F) Quantification of Type I/II damaged VEGFR3$^+$ sinusoidal vessels in young or aged WBM-young EC co-infused cohorts (n=10 mice/cohort; related to panel B). Error bars represent sample mean±SEM. Two-tailed unpaired Student's t-test were used to determine significance (* P<0.05;  P<0.01; * P<0.001). Steady state controls are used as a reference point and are not included in statistical analysis.

FIG. 7A-FIG. 7F show endothelial cell co-infusion mitigates myeloablative hematopoietic injury. (FIG. 7A-FIG. 7B) Representative Hematoxylin and Eosin (H&E) stained longitudinal femur time-course post-irradiation (950 Rads) from (FIG. 7A) young or (FIG. 7B) aged whole bone marrow (WBM)-endothelial cell (EC) co-infused mice (n=10 mice/cohort; 100× magnification). Steady state control H&E sections are inset. (FIG. 7C-FIG. 7D) Representative contour plots of bone marrow (BM) granulocyte-macrophage (GM) frequency in (FIG. 7C) young and (FIG. 7D) aged WBM-EC co-infusions seven days post-irradiation. (FIG. 7E-FIG. 7F) Time-course of BM GM counts in (FIG. 7E) young and (FIG. 7F) aged WBM-EC co-infusions seven days post-irradiation. Comparisons of WBM to WBM+EC cohorts using two-tailed unpaired Student's t-test at individual time points was performed to determine significance (* P<0.05;  P<0.01; * P<0.001). Steady state controls are used as a reference point and are not included in statistical analysis.

FIG. 8A-FIG. 8F show representative contour plots of hematopoietic expansion and multi-lineage engraftment. (FIG. 8A-FIG. 8B) Hematopoietic populations following 14 days of expansion on endothelial cells (ECs). Hematopoietic populations were enriched using CD45 microbeads following expansion. (FIG. 8A) Lineage$^-$ (GR1$^-$CD11B$^-$B220$^-$CD3$^-$CD41$^-$TER119$^-$) cell populations. Red box/arrow indicates gating strategy for phenotypic hematopoietic stem and progenitor cells (HSPCs). (FIG. 8B) Phenotypic lineage$^-$cKIT$^+$SCA1$^+$ (LKS) HSPCs (red box). Lineage$^-$cKIT$^+$SCA1$^{High}$ populations are indicated (dashed blue box). (FIG. 8C-FIG. 8F) Long-term multi-lineage reconstitution of HSPC/EC ex vivo expansions four months post-transplantation. (FIG. 8C) Representative plots of CD45.2$^+$ CD45$^-$ peripheral blood hematopoietic engraftment. All engraftment plots were gated on TER119$^-$ cell populations. (FIG. 8D) Representative plots of GR1$^+$CD11B$^+$ myeloid cell, (FIG. 8E) B220$^+$CD19$^+$ B Cell, and (FIG. 8F) CD8$^+$/CD4$^+$ T Cell reconstitution. All multi-lineage plots were gated on total CD45.2$^+$ cell populations.

(FIG. 9A-FIG. 9B) Whole bone marrow (105 cells) from (FIG. 9A) young (3 month) or (FIG. 9B) aged (24 month) C57BL/6 mice were co-infused with or without 5×10$^5$ young endothelial cells (ECs) in a non-competitive setting following lethal total body irradiation (950 Rads). Surviving mice were assessed for multi-lineage reconstitution four months post-TBI (n=10 mice/cohort). Unpaired two-tailed Student's t-tests were performed to determine significance (* P<0.05;  P<0.01; * P<0.001).

FIG. 10A-FIG. 10E shows co-infusion of young endothelium supports HSPC activity. Whole bone marrow (WBM) from young (3 month) and aged (24 month) C57BL/6 mice were co-infused with or without 5×10$^5$ young endothelial cells (ECs) into lethally-irradiated recipients (950 Rads) and assessed for hematopoietic stem and progenitor activity. (FIG. 10A) Representative images of colony-forming units-spleen (CFU-S) in mice eight days following transplantation with 10$^5$ WBM with or without young ECs. (FIG. 10B-FIG. 10C) Limiting dilution data displaying the frequency of long-term multi-lineage reconstitution (LTMR) of non-competitive WBM transplantations from (FIG. 10B) young and (FIG. 10C) aged mice (n=10 mice/cohort). Stem cell frequency and 95% confidence intervals were determined using Extreme Limiting Dilution Analysis (ELDA). (FIG. 10D-FIG. 10E) Hematopoietic homing analysis of 10$^6$ young and aged CD45.2$^+$ WBM with and without 5×10$^5$ young ECs infused/co-infused in lethally-irradiated (950 Rads) recipients. Data demonstrates no observable differences between hematopoietic homing in the (FIG. 10D) bone marrow or (FIG. 10E) spleen 16 hours post-infusion. Unpaired two-tailed Student's t-tests were performed to determine significance (* P<0.05;  P<0.01; * P<0.001).

DETAILED DESCRIPTION OF THE INVENTION

Figure 4A:
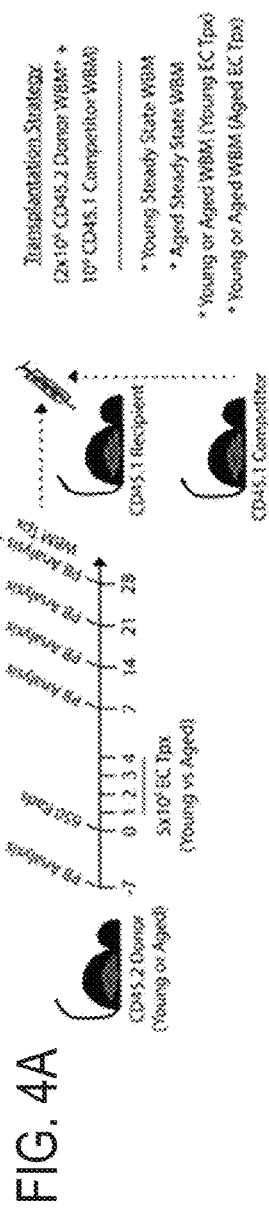
FIGS. 4A-4F show infusion of young endothelium promotes hematopoietic recovery in aged recipients following myelosuppressive injury.

Studies describing age-related changes in the hematopoietic compartment have primarily focused on cell-intrinsic hematopoietic stem cell (HSC) alterations. While these studies demonstrate that intrinsic changes contribute to aging of the hematopoietic system, most have not adequately taken into account the effects of the aged bone marrow (BM) microenvironment. Understanding the aging-dependent cellular changes to the BM microenvironment that impair HSC function and hematopoietic output will be critical in developing new and adjunct therapies to treat age-related hematological disorders. The present disclosure is based, in part, on the finding that the aging of endothelial cells (ECs), a critical component of the BM microenvironment, is sufficient to drive hematopoietic aging phenotypes in young HSCs. The present disclosure describes that an age-dependent dysregulation of the BM endothelial niche is sufficient to disrupt the homeostatic HSC supportive microenvironment and drive aging-associated hematopoietic phenotypes. The findings presented in the present disclosure lay the groundwork for the exploration of EC therapies that can serve as adjuvant modalities to enhance HSC engraftment and accelerate hematopoietic recovery in the elderly population following myelosuppressive regimens.

It has been determined herein that aging of endothelial cells (ECs), a critical component of the bone marrow (BM) microenvironment, is sufficient to drive hematopoietic aging phenotypes in young hematopoietic stem cells (HSCs). Conversely, it has been demonstrated herein that young ECs can restore the repopulating capacity of aged HSCs. Furthermore, it has been shown herein that infusion of young bone marrow ECs (BMECs) enhanced the hematopoietic recovery following myelosuppressive injury and restored endogenous HSC function in aged mice. Moreover, it has been shown herein that coinfusion of young ECs augmented aged HSC engraftment and enhanced overall survival in lethally irradiated mice by mitigating damage to the BM endothelial niche. Accordingly, this disclosure provides therapeutic methods utilizing ECs as adjuvant modalities to enhance HSC engraftment and accelerate hematopoietic recovery in the elderly population following myelosuppressive regimens.

I. Definitions

In order that the described invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to" or "including, without limitation."

The term "or" is used herein to mean, and is used interchangeably with, the term "and/or," unless context clearly indicates otherwise. For example, a nucleoside with a modified base or a modified sugar is understood to include the options of a nucleoside with a modified base, a nucleoside with a modified sugar, and a nucleoside with a modified base and a modified sugar.

The term "about" is used herein to mean within the typical ranges of tolerances in the art. For example, "about" can be understood as about 2 standard deviations from the mean. According to certain embodiments, about means+10%. According to certain embodiments, about means+5%. When about is present before a series of numbers or a range, it is understood that "about" can modify each of the numbers in the series or range.

The term "at least" prior to a number or series of numbers (e.g. "at least two") is understood to include the number adjacent to the term "at least", and all subsequent numbers or integers that could logically be included, as clear from context. When at least is present before a series of numbers or a range, it is understood that "at least" can modify each of the numbers in the series or range.

As used herein, "up to" as in "up to 10" is understood as up to and including 10, i.e., 0, 1, 2, 3, 4, 5, 6, 7, 8, 9, or 10.

Ranges provided herein are understood to include all individual integer values and all subranges within the ranges.

As used herein, the term "in combination with," is not intended to imply that the therapy or the therapeutic agents must be administered at the same time and/or formulated for delivery together, although these methods of delivery are within the scope described herein. The therapeutic agents can be administered concurrently with, prior to, or subsequent to, one or more other additional therapies or therapeutic agents.

As used herein, the term "administration" and its various grammatical forms as it applies to a mammal, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. "Administration" also encompasses in vitro and ex vivo treatments, e.g., of a cell, by a reagent, diagnostic, binding composition, or by another cell.

As used herein, the term "aging stem cell" or "aged stem cell" is meant to refer to a stem cell(s) that may exhibit one or more of the following properties: decreased per cell repopulating activity, decreased self-renewal and homing abilities, myeloid skewing of differentiation, and increased apoptosis with stress (Janzen et al., Nature, 2006, v. 443, p. 421, incorporated by reference in its entirety herein). Any methods known in the art to evaluate these properties may be used to identify aging stem cells. For example, assays such as competitive repopulation and transplantation, engraftment, colony-forming unit assays, and long-term culture assays may be used.

As used herein, the term "autoimmune disease" is meant to refer generally to conditions in which a subject's immune system attacks the body's own cells, causing tissue destruction. Autoimmune diseases may be diagnosed using blood tests, cerebrospinal fluid analysis, electromyogram (measures muscle function), and magnetic resonance imaging of the brain, but antibody testing in the blood, for self-antibodies (or auto-antibodies) is particularly useful.

As used herein, the term "bone marrow disease" is meant to refer to a disease in which the normal bone marrow architecture is displaced by malignancies, sickle cell disease, myelodysplastic syndrome, myeloproliferative disorders, aplastic anemia, or infections leading to a decrease in the production of blood cells and blood platelets. Said bone marrow disease can be for example leukemia, a defect of the blood cell compartment or a need for bone marrow transplantation after chemotherapy or irradiation treatment. In some embodiments, the defect of the blood cell compartment can be a hemoglobinopathy like thalassaemia, defects in neutrophil granulocyte function, a defect in neutrophil granulocyte function, a defect in T- and/or B-lymphocytes, e.g., severe combined immunodeficiency, Bruton's agammaglobulinemia. In some embodiments, the bone marrow disease is aplastic anemia. In some embodiments, the bone marrow disease is a myeloproliferative disorder. In some embodiments, the bone marrow disease is a lymphoma.

As used herein, the term "cancer" refers to diseases in which abnormal cells divide without control and are able to invade other tissues. There are more than 100 different types of cancer. Most cancers are named for the organ or type of cell in which they start—for example, cancer that begins in the colon is called colon cancer; cancer that begins in melanocytes of the skin is called melanoma. Cancer types can be grouped into broader categories. The main categories of cancer include: carcinoma (meaning a cancer that begins in the skin or in tissues that line or cover internal organs, and its subtypes, including adenocarcinoma, basal cell carcinoma, squamous cell carcinoma, and transitional cell carcinoma); sarcoma (meaning a cancer that begins in bone, cartilage, fat, muscle, blood vessels, or other connective or supportive tissue); leukemia (meaning a cancer that starts in blood-forming tissue (e.g., bone marrow) and causes large numbers of abnormal blood cells to be produced and enter the blood; lymphoma and myeloma (meaning cancers that begin in the cells of the immune system); and Central nervous system cancers (meaning cancers that begin in the tissues of the brain and spinal cord). The term "myelodysplastic syndrome" refers to a type of cancer in which the bone marrow does not make enough healthy blood cells (white blood cells, red blood cells, and platelets) and there are abnormal cells in the blood and/or bone marrow. Myelodysplastic syndrome may become acute myeloid leukemia (AML).

As used herein, the term "cellular migration" or "cell migration" is meant to refer to the orchestrated movement of cells in particular directions to specific locations.

As used herein, a "control hematopoietic cell population" is meant to refer to a group of HSCs that is not contacted with endothelial cells. According to some embodiments, the control hematopoietic cell population is aged matched to the group of HSCs contacted with endothelial cells. According to some embodiments, the control hematopoietic cell population comprises hematopoietic stem cells from a young adult.

As used herein, the term "contact" and its various grammatical forms is meant to refer to a state or condition of touching or of immediate or local proximity. Contacting a composition to a target destination may occur by any means of administration known to the skilled artisan.

As used herein, the term "derived from" is meant to refer to a cell or group of cells (a cell population) generated from a source.

As used herein, the term "dose" is meant to refer to the quantity of a therapeutic substance prescribed to be taken at one time.

As used herein, the term "endothelial cell vascular niche" is meant to refer to the microenvironment where the endothelial cells and stem cells reside. According to one embodiment, the vascular niche promotes proliferation, differentiation of actively cycling, and short-term HSCs.

As used herein, the term "endothelial stiffness" is meant to refer to a property of endothelial cells that, amongst other things, depends on the stiffness of the nucleus, the osmotic pressure and the cellular coat (i.e. the glycocalyx) (Fels et al., 2014 Cell Tissue Res. 355, 727-737). According to one embodiment, cytoskeletal dynamics, triggered through adhesion receptors or by soluble receptor ligands, regulate cellular stiffness in a highly dynamic and well-organized fashion. According to certain embodiments, endothelial stiffness of living endothelial cells can be determined by using atomic force microscopy (AFM). Endothelial stiffness is associated with many vascular pathologies.

As used herein, the term "enrich" is meant to refer to an increase in a certain cell type within a given population. According to one embodiment, a CD34+CD38−phenotype defines a cell population enriched in HSCs. According to one embodiment, a CD34+CD38−CD45RA− phenotype defines a cell populationenriched in HSCs. According to one embodiment, a CD34+CD38−CD45RA−CD90+ phenotype is now customarily accepted to defines a cell population enriched in HSCs.

As used herein, the term "epigenetic" is meant to refer to relating to or arising from nongenetic influences on gene expression. According to some embodiments, epigenetic refers to the temporal and spatial control of gene activity during development.

As used herein, the term "expand" is meant to refer to an increase in total number of cells. According to one embodiment, HSC expansion refers to an increase in total number of HSCs.

As used herein, the term "hematopoiesis" is meant to refer generally to the process of cellular differentiation or formation of specialized blood cells from an HSC. During development, hematopoiesis translocates from the fetal liver to the bone marrow, which then remains the site of hematopoiesis throughout adulthood. Once established in the bone marrow, HSCs are not distributed randomly throughout the bone cavity. Rather, HSCs are typically found in close proximity to the endosteal surfaces. The more mature stem cells increase in number as the distance from the bone surface increases.

As used herein, "hematopoietic cells" are meant to include all types of blood cells from the myeloid (monocyte, macrophases, neutrophils, basophils, eosinophils, erythrocytes, platelets and dendritic cells) and lymphoid lineages (T-cells, B-cells and NK-cells).

As used herein, the term "hematopoietic recovery" is meant to refer to the reconstitution of the hematopoietic system in a subject. According to one embodiment, hematopoietic recovery is assessed by the number of red blood cells, white blood cells and/or platelets. According to one embodiment, a red blood cell count of 4.32-5.72 trillion cells/L or greater indicates hematopoietic recovery in a male subject and a red blood cell count of 3.90-5.03 trillion cells/L or greater indicates hematopoietic recovery in a female subject. According to one embodiment, a white blood cell count of 3.5-10.5 billion cells/L or greater indicates hematopoietic recovery in a male or female subject. According to one embodiment, a platelet count of 150-450 billion/L or greater indicates hematopoietic recovery in a male or female subject.

As used herein, the term "hematopoietic stem cells" (HSCs) is meant to refer to either pluripotent or multipotent hematopoietic stem cells that give rise to the blood cell types, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art. HSCs may be identified according to certain phenotypic or genotypic markers. For example, HSCs may be identified by their small size, lack of lineage (lin) markers (lin(−)), low staining (side population) with vital dyes such as rhodamine 123, or Hoechst 33342, and presence of various antigenic markers on their surface, many of which belong to the cluster of differentiation series (e.g., CD5, CD11b, CD34, CD38, CD90, CD133, CD105, CD45, GR-1 (=Ly-6G/C), 7-4, Ter-119 and c-kit). HSCs are mainly negative for the markers that are typically used to detect lineage commitment, and, thus, are often referred to as lin(−) cells. Most human HSCs may be characterized as CD5$^+$, CD45R (B220)+, CD11$^+$, GR-1$^+$, CD34+, CD59$^+$, Thy1/CD90$^+$, CD38$^{low}$, C-kit/CD117$^+$, and lin($^-$). However, not all stem cells are covered by these combinations, as certain HSCs are CD347$^+$ and CD38$^+$. Also some studies suggest that earliest stem cells may lack c-kit on the cell surface.

As used herein, the term "hematopoietic progenitors" is meant to refer to cells which are derived from HSCs, and give rise to selected blood cell types. Hematopoietic progenitors have limited replicative potential and burn out after a few days-weeks.

As used herein, the term "incubating" is meant to refer to hematopoietic stem cells that are brought into contact with another cell (e.g. endothelial cells) or agent. In some embodiments, it means that a sample containing hematopoietic stem cells is mixed with endothelial stem cells to obtain a hematopoietic cell/endothelial cell population.

As used herein, "lineage-restricted progenitor cells (LRPs)" is meant to refer to a progenitor cell that is functionally and structurally limited to behave in a differentiated manner. According to one embodiment, the cell lineages are produced from a population of multipotent cells. According to one embodiment, LRPs are CD150−CD48+CD244+.

As used herein, the term "lymphoid lineage" is meant to refer to blood cells that are generated from HSCs, and include T, B, and natural killer (NK) cells. Lymphoid lineage is separable from myeloid lineage at the progenitor stage.

As used herein, the terms "marker" or "cell surface marker" are used interchangeably herein to refer to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

As used herein, the term "multipotent" is meant to refer to a cell that can develop into more than one cell type, but is more limited than pluripotent cells. According to some embodiments, adult stem cells and cord blood stem cells are considered multipotent.

As used herein, the term "myeloid lineage" is meant to refer to blood cells that are generated from HSCs, and include megakaryocytes and erythrocytes (MegE) as well as granulocytes and macrophages. Myeloid lineage is separable from lymphoid lineage at the progenitor stage.

As used herein, the term "myelosuppresive regimen" or "myelosuppresive therapy" is meant to refer to a treatment that stops or slows the growth of blood-forming cells in the bone marrow. Myelosuppressive therapies, such as chemotherapy and radiation therapy, kill normal cells and cancer cells in the bone marrow. This lowers the number of normal red blood cells, white blood cells, and platelets in the blood and bone marrow. Myelosuppressive therapy may be given before a bone marrow or stem cell transplant. According to certain embodiments, a myelosuppresive regimen is selected from peginterferon alfa-2a, interferon alfa-n3, peginterferon alfa-2b, aldesleukin, gemtuzumab ozogamicin, interferon alfacon-1, rituximab, ibritumomab tiuxetan, tositumomab and alemtuzumab.

As used herein, the term "oligopotent" is meant to refer to the ability of progenitor cells to differentiate into a few cell types. According to some embodiments, oligopotent is a degree of potency. Examples of oligopotent stem cells are the lymphoid or myeloid stem cells.

As used herein, the term "pediatric subject" is meant to refer to a subject who is an infant or a child.

As used herein, the term "progenitor cell" is meant to include a biological cell that, like a stem cell, has a tendency to differentiate into a specific type of cell, but is already more specific than a stem cell and is pushed to differentiate into its target cell. Progenitor cells are early descendants of stem cells that can differentiate to form one or more kinds of cells. The most important difference between stem cells and progenitor cells is that stem cells can replicate indefinitely, whereas progenitor cells can divide only a limited number of times. Most progenitors are described as oligopotent, they may be compared to adult stem cells. Progenitors are said to be in a further stage of cell differentiation, i.e. they are in the "center" between stem cells and fully differentiated cells. The kind of potency they have depends on the type of their "parent" stem cell and also on their niche. Progenitor can move through the body and migrate towards the tissue where they are needed. Many properties are shared by adult stem cells and progenitor cells.

As used herein, the phrase "promoting HSC engraftment" is meant that the survival, BM hematopoietic reconstitution, and/or hematopoietic progenitor activity following HSC transplant are supported or enhanced. By "HSC-supportive ECs", it is meant that the ECs can support, promote, and/or enhance HSC function (i.e. support, promote, and/or enhance the self-renewal, survival, and repopulating activity, including both long-term and short-term regeneration abilities, to give rise to both the myeloid and lymphoid lineages of the blood.

As used herein, the term "stem cell" is meant to refer to cells that are characterized by their ability to form multiple cell types (i.e. being multipotent) and their ability for self-renewal. Oligopotent and unipotent progenitors may be included also.

As used herein, the terms "subject" or "individual" or "patient" are used interchangeably to refer to a member of an animal species of mammalian origin, including humans. According to some embodiments, a "subject" includes anyone who is a candidate for autologous stem cell or bone marrow transplantation during the course of treatment for malignant disease or as a component of gene therapy. Other possible candidates are subjects who donate stem cells or bone marrow to subjects for allogeneic transplantation for malignant disease or gene therapy. Subjects may have undergone irradiation therapy, for example, as a treatment for malignancy of cell type other than hematopoietic. Subjects may be suffering from anemia, e.g., sickle cell anemia, thalessemia, aplastic anemia, or other deficiency of HSC derivatives.

As used herein, the term "therapeutic agent" is meant to refer to a drug, molecule, nucleic acid, protein, metabolite, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably herein.

As used herein, the term "transplant" is meant to refer to the transplantation of multipotent hematopoietic stem cells, usually derived from bone marrow, peripheral blood, or umbilical cord blood or the transplantation bone marrow endothelial cells, derived from the bone marrow. Transplant of HSCs or bone marrow endothelial cells may be autologous (the patient's own stem cells are used) or allogeneic (the stem cells come from a donor).

As used herein, the term "treat" or "treating" includes abrogating, substantially inhibiting, slowing or reversing the progression of a condition, substantially ameliorating clinical symptoms of a condition, or substantially preventing the appearance of clinical symptoms of a condition. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

As used herein, the term "wound healing" is meant to refer to the regeneration and tissue repair processes consisting of a sequence of molecular and cellular events which occur after the onset of a tissue lesion in order to restore the damaged tissue. According to some embodiments, wound healing consists of exudative, proliferative, and extracellular matrix remodeling phases According to one embodiment, wound healing can be assessed using a scratch wound assay. A scratch wound assay can measure cell migration parameters such as speed, persistence, and polarity. In a typical scratch wound healing assay, a wound gap in a cell monolayer is created by scratching, and the healing of this gap by cell migration and growth towards the center of the gap is monitored and often quantitated. Factors that alter the motility and/or growth of the cells can lead to increased or decreased rate of "healing" of the gap (Lampugnani, M. G. (1999). Methods in Mol Biol 96: 177-182, incorporated by reference in its entirety herein).

Hematopoietic Stem Cells

The methods of the described invention utilize hematopoietic stem cells (HSCs). Hematopoietic stem cells may be isolated from blood (i.e. hematopoietic tissue). Possible sources of human hematopoietic tissue include, but are not limited to, embryonic hematopoietic tissue, fetal hematopoietic tissue, and post-natal hematopoietic tissue. Embryonic hematopoietic tissue can be yolk sac or embryonic liver. Fetal hematopoietic tissue can come from fetal liver, fetal bone marrow and fetal peripheral blood. The post-natal hematopoietic can be cord blood, bone marrow, normal peripheral blood, mobilized peripheral blood, hepatic hematopoietic tissue, or splenic hematopoietic tissue.

Exemplary HSCs for use with the methods of the present disclosure may be derived by any technique known in the art. For example, HSCs may be found in the bone marrow of a donor, which includes femurs, hip, ribs, sternum, and other bones. Any method known in the art for extracting or harvesting bone marrow cells may be used. According to one non-limiting example, HSCs may be derived directly from the marrow cavity of the hip using a needle and syringe to aspirate cells from the marrow cavity. Rich marrow may be derived from the hip by performing multiple small aspirations.

Alternatively, exemplary HSCs may be derived from peripheral blood cells found in the blood of a donor, optionally following pre-treatment with cytokines, such as G-CSF (granulocyte colony-stimulating factors), that mobilizes HSCs to be released from the bone marrow compartment of the donor. HSCs may also be derived from peripheral blood that has undergone an apheresis procedure to enrich for HSCs. Any apheresis procedure known in the art may be used (e.g. a leukapheresis procedure).

Additionally, exemplary HSCs may be derived from umbilical cord blood, placenta, and mobilized peripheral blood. For experimental purposes, fetal liver, fetal spleen, and AGM (Aorta-gonad-mesonephros) of animals are also useful sources of HSCs. Additionally, HSCs may be procured from a source that derived HSCs from the bone marrow, peripheral blood, umbilical cord, or fetal tissue of a donor.

According to some embodiments, HSCs are derived from a human umbilical cord or placenta. Another source of HSCs that may be utilized is the developing blood-producing tissues of fetal animals. In humans, HSCs may be found in the circulating blood of a human fetus by about 12 to 18 weeks.

According to some embodiments, human HSCs are derived from any source, e.g., the bone marrow, umbilical cord, peripheral blood, or fetal tissue of blood, of type A+, A−, B+, B−, O+, O−, AB+, and AB− donors. According to other embodiments, human HSCs are derived from any source, e.g., the bone marrow, umbilical cord, peripheral blood, or fetal tissue of blood, of universal donors or donors having a rare blood type.

According to other embodiments, human HSCs are derived from any source, e.g., the bone marrow, umbilical cord, peripheral blood, or fetal tissue of blood, of donors having an aging disorder or aging-associated condition that would benefit from a transplantation of HSCs and/or transfusion of blood. Such donors may also be the recipients. Advantageously, HSCs derived from such donor may be used for personalized HSC and/or blood therapy.

According to one non-limiting example, human HSCs may be derived by anesthetizing the stem cell donor, puncturing the posterior superior iliac crest with a needle, and performing aspiration of bone marrow cells with a syringe. According to another non-limiting example, HSCs may be derived from the peripheral blood of a donor, where a few days prior to harvesting the stem cells form the peripheral blood, the donor is injected with G-CSF in order to mobilize the stem cells to the peripheral blood.

Cells derived from, for example, bone marrow, peripheral blood, or cord blood, are typically processed after extraction or harvest. Any method known in the art for processing extracted or harvested cells may be used. Examples of processing steps include, without limitation, filtration, centrifugation, screening for hematopathologies, screening for viral and/or microbial infection, erythrocyte depletion, T-cell depletion to reduce incidence of graft-versus-host disease in allogenic stem cell transplant recipients, volume reduction, cell separation, resuspension of cells in culture medium or a buffer used for subsequent processing, separation of stem cells from non-stem cells (e.g., stem cell enrichment), ex vivo or in vitro stem cell expansion with growth factors, cytokines, and/or hormones, and cryopreservation.

Any exemplary method for stem cell enrichment known in the art may be used. Examples of stem cell enrichment methods include, without limitation, fluorescence activated cell sorting (FACS) and magnetic activated cell sorting (MACS).

According to certain embodiments, exemplary HSCs for use in the methods of the present disclosure are human HSCs.

Identification and Targeting of HSCs

HSCs derived from a donor may be identified and/or enriched by any exemplary method of stem cell identification and enrichment known in the art, such as by utilizing certain phenotypic or genotypic markers. For example, in some embodiments, identification of HSCs includes using cell surface markers associated with HSCs or specifically associated with terminally differentiated cells of the system. Exemplary surface markers may include, without limitation, one or more of c-kit (Invitrogen Cat #34-8800, Cat #17-1179-42, Cat #47-1171-82), Sca-1 (Invitrogen Cat #11-5981-82), CD4 (AbCam [EPR6855] (ab133616); AbCam [EPR19514] (ab183685)), CD34 (Invitrogen Cat #07-3403; Invitrogen Cat #11-0341-82), CD38 (MACS Clone: REA572), Thy1 (Invitrogen Cat #11-0903-82), CD2 (Creative Biolabs HPAB-0019-LS: Creative Biolabs MOB-1136z), CD3 (AbCam (ab16669)), CD4 (AbCam (ab133616)), CD5 (AbCam (ab75877)), CD8 (AbCam (ab4055)), CD43 (AbCam (ab9088)), CD45 (AbCam (ab10558)), CD59 (AbCam (ab9182)), CD90 (AbCam (ab225)), CD105 (AbCam (ab11414)), CD133 (AbCam (ab19898)), CD135 (AbCam,(ab197838)), NK1.1 (AbCam (ab236533)), B220 (AbCam (ab10558)), Ter-119 (AbCam (ab91113)), Flk-2 (AbCam (ab37847)), CDCP1 (AbCam (ab1377)), Endomucin (AbCam (ab106100)), Gr-1 (AbCam), CD46 (AbCam (ab108307)), Mac-1, Thy1.1 (AbCam (ab95813)), and the signaling lymphocyte activation molecule (SLAM) family of receptors. Examples of SLAM receptors include, without limitation, CD150 (AbCam (ab2604)), CD48 (AbCam (ab9185)), and CD244 (AbCam (ab95805)).

Additionally, HSCs derived from a donor may be separated from non-stem cells by any exemplary method known in the art including, without limitation, fluorescence activated cell sorting (FACS) and magnetic activated cell sorting (MACS).

According to one non-limiting example, human peripheral blood cells are incubated with antibodies recognizing c-kit (Invitrogen Cat #34-8800, Cat #17-1179-42, Cat #47-1171-82), Sca-1 (Invitrogen Cat #11-5981-82), CD4 (AbCam [EPR6855] (ab133616); AbCam [EPR19514] (ab183685)), CD34 (Invitrogen Cat #07-3403; Invitrogen Cat #11-0341-82), CD38 (MACS Clone: REA572), Thy1 (Invitrogen Cat #11-0903-82), CD2 (Creative Biolabs HPAB-0019-LS: Creative Biolabs MOB-1136z), CD3 (AbCam (ab16669)), CD4 (AbCam (ab133616)), CD5 (AbCam (ab75877)), CD8 (AbCam (ab4055)), CD43 (AbCam (ab9088)), CD45 (AbCam (ab10558)), CD59 (AbCam (ab9182)), CD90 (AbCam (ab225)), CD105 (AbCam (ab11414)), CD133 (AbCam (ab19898)), CD135 (AbCam, (ab197838)), NK1.1 (AbCam (ab236533)), B220 (AbCam (ab10558)), Ter-119 (AbCam (ab91113)), Flk-2 (AbCam (ab37847)), CDCP1 (AbCam (ab1377)), Endomucin (AbCam (ab106100)), or Gr-1 (AbCam). Antibodies for CD2, CD3, CD4, CD5, CD8, NK1.1, B220, Ter-119, and Gr-1 are conjugated with magnetic beads. The cells expressing CD2, CD3, CD4, CD5, CD8, NK1.1, B220, Ter-119, or Gr-1 are retained in the column equipped to trap magnetic beads and cells attached to magnetic bead conjugated antibodies. The cells that are not captured by the MACS column are subjected to FACS analysis. Antibodies for c-kit (Invitrogen Cat #34-8800, Cat #17-1179-42, Cat #47-1171-82), Sca-1 (Invitrogen Cat #11-5981-82), CD34 (Invitrogen anti-CD34 Monoclonal Antibody (BI-3C5); anti-CD34 Monoclonal Antibody (RAM34), FITC, eBioscience), CD38 (BD Pharmingen Alexa Fluor 647 Rat Anti-Mouse CD38), Thy1 (Invitrogen Cat #11-0903-82; Invitrogen Cat #11-0909-42), are conjugated with fluorescent materials known in the art. The cells that are CD34$^+$, CD38$^{low/-1}$, Thy1$^+$ are separated from the rest of sample by virtue of the types of fluorescent antibodies associated with the cells. These cells are provided as exemplary human long-term HSCs for use with any of the methods of the present disclosure.

According to another non-limiting example, cells derived from a subject are labeled with the same set of magnetic bead conjugated antibodies as described above (antibodies against one or more of CD2, CD3, CD4, CD5, CD8, NK1.1, B220, Ter-119, or Gr-1) and fluorescent conjugated CD150 (AbCam (ab2604)), CD244 (AbCam (ab95805)) and/or CD48 (AbCam (ab9185)) antibodies. After removing cells captured by the magnetic bead conjugated antibodies from the sample, the sample is analyzed by FACS and CD150$^+$, CD244$^-$ and CD48$^-$ cells are retained as long-term HSCs.

According to some embodiments, HSCs utilized in the methods of the present disclosure contain one or more of the markers: c-kit$^+$, Sca-1$^+$, CD34$^{low/-}$, CD38$^+$, Thy1$^{+/low}$, CD34$^+$, CD38$^{low/-}$, c-kit$^{-/low}$, and/or Thy1$^+$. According to some embodiments, the HSCs utilized in the methods of the present disclosure lack one or more of the markers: CD2, CD3, CD4, CD5, CD8, NK1.1, B220, Ter-119, and/or Gr-1. According to certain embodiments, the HSCs are of an A+, A−, B+, B−, O+, O−, AB+, or AB− type.

According to one embodiment, the following panel of antibodies (Caltag/Invitrogen and BD Biosciences) can be used for analysis and sorting of human hematopoietic stem and progenitor populations: PE-Cy5-conjugated anti-human lineage markers (anti-CD2, RPA-2.10; anti-CD3, S4.1; anti-CD4, S3.5; anti-CD7, CD7-6B7; anti-CD8, 3B5; anti-CD10, 5-1B4; anti-CD11b, ICRF44; anti-CD14, TU.K.4; anti-CD19, SJ25-C1; anti-CD20, 13.6E12; anti-CD56, B159; anti-GPA, GA-R2), PB-conjugated anti-CD45RA, MEM56; PE-Cy7-conjugated anti-CD38, HIT2; FITC-conjugated or Alexa Fluor 700-conjugated anti-CD90 (Thy-1), 5E10; PE-conjugated or FITC-conjugated anti-CD123; PE-conjugated anti-CD127, hIL-7R-M21.

According to one embodiment, the following panel of antibodies (Caltag/Invitrogen and BD Biosciences) can be used for analysis of differentiated human hematopoietic populations and human engraftment/chimerism: PB-conjugated CD45, HI30; APC-conjugated anti-CD34, 8G12; Alexa Fluor 750-conjugated CD3, S4.1; Alexa Fluor 700-conjugated CD19, SJ25-C1; PE-conjugated CD13, TK1; PE-conjugated CD33, P67.6; PE-Cy5-conjugated GPA, GA-R2; FITC-conjugated CD41a, HIP8. The following panel of antibodies (eBiosciences) was used to identify mouse leukocytes and red blood cells, respectively: Alexa Fluor 488- or PE-Cy7-conjugated CD45.1, A20.1.7; PE-Cy5- or PE-Cy7-conjugated Ter119. Single-cell suspensions were prepared using standard methods from bone marrow of transplanted mice. Red blood cells were lysed using ACK buffer.

Alternatively, exemplary HSCs may be derived from a non-human source. Exemplary non-human HSCs may be isolated from, femurs, hip, ribs, sternum, and other bones of a non-human animal, including, without limitation, laboratory/research animals, rodents, pets, livestock, farm animals, work animals, pack animals, rare or endangered species, racing animals, and zoo animals. Further examples of exemplary non-human animals include, without limitation, monkeys, primates, mice, rats, guinea pigs, hamsters, dogs, cats, horses, cows, pigs, sheep, goats, and chickens. For example, HSCs may be derived from murine bone marrow cells, by incubating the bone marrow cells with antibodies recognizing cell surface molecules such as one or more of c-kit, Sca-1, CD34, CD38, Thy1, CD2, CD3, CD4, CD5, CD8, CD43, CD45, CD59, CD90, CD105, CD133, ABCG2, NK1.1, B220, Ter-119, Flk-2, CDCP1, Endomucin, or Gr-1. Antibodies for CD2, CD3, CD4, CD5, CD5, NK1.1, B220, Ter-119, and Gr-1 are conjugated with magnetic beads. In MACS equipment, the cells harboring CD2, CD3, CD4, CD5, CD8, NK1.1, B220, Ter-119, or Gr-1 on their surface are retained in the column equipped to trap magnetic beads and the cells attached to magnetic bead conjugated antibodies. The cells that are not captured by MACS column are subjected to FACS analysis. For FACS analysis, Antibodies for surface molecules such as c-kit, Sca-1, CD34, CD38, Thy1, are conjugated with fluorescent materials. The cells that are c-kit$^+$, Sca-1$^+$, CD34$^{low/-}$, CD38$^+$, Thy1$^{+/low}$ are separated from the rest of the sample by virtue of the types of fluorescent antibodies associated with the cells. These cells are provided as murine long-term HSCs that can be used with any of the methods of the present disclosure. According to other embodiments, different sets of marker are used to separate murine long-term HSCs from cells of bone marrow, umbilical cord blood, fetal tissue, and peripheral blood.

According to some embodiments, obtaining HSCs from bone marrow includes first injecting the HSC donor, such as a mouse or other non-human animal, with 5-fluorouracil (5-FU) to induce the HSCs to proliferate in order to enrich for HSCs in the bone marrow of the donor.

Further, exemplary HSCs for use with any of the methods of the present disclosure, whether derived from, or present in, cord blood, bone marrow, peripheral blood, or other source, may be grown or expanded in any known, commercially available or custom defined medium (e.g., Hartshorn et al., Cell Technology for Cell Products, pages 221-224, R. Smith, Editor; Springer Netherlands, 2007). For example, serum free medium may utilize albumin and/or transferrin, which have been shown to be useful for the growth and expansion of CD34.sup.+ cells in serum free medium. Also, cytokines may be included, such as Flt-3 ligand, stem cell factor (SCF), and thrombopoietin (TPO), among others. HSCs may also be grown in vessels such as bioreactors (e.g., Liu et al., Journal of Biotechnology 124:592-601, 2006). An exemplary medium for ex vivo expansion of HSCs may also contain HSC supporting cells, such as stromal cells (e.g., lymphoreticular stromal cells), which can be derived, for example, from the disaggregation of lymphoid tissue, and which have been shown to support the in vitro, ex vivo, and in vivo maintenance, growth, and differentiation of HSCs, as well as their progeny.

HSC growth or expansion may be measured in vitro or in vivo according to routine techniques known in the art. For example, WO 2008/073748, describes methods for measuring in vivo and in vitro expansion of HSCs, and for distinguishing between the growth/expansion of HSCs and the growth/expansion of other cells in a potentially heterogeneous population (e.g., bone marrow), including for example intermediate progenitor cells.

HSC Cell Lines

According to some embodiments, exemplary HSCs for use in any of the methods of the present disclosure may also be derived from an HSC cell line. Exemplary HSC cell lines include any cultured hematopoietic stem cell line known in the art. Non-limiting examples include the conditionally immortalized long-term stem cell lines described in U.S. Patent Application Publication Nos. US 2007/0116691 and US 2010/0047217.

In any of aspects and embodiments described herein, the source of hematopoietic stem cells is autologous. In any of the foregoing embodiments, the source of hematopoietic stem cells is allogeneic and the donor cells are HLA-matched to the recipient.

Identifying Rejuvenated and/or Preserved HSCs

According to certain aspects, the disclosure provides a hematopoietic stem cell population, wherein the population is characterized by one or more of (i) improved performance in an HSC engraftment assay; (ii) improved bone marrow reconstitution; (iv) improved hematopoietic recovery; (v) increased repopulating activity; and (vi) improved self-renewal, compared to a control hematopoietic stem cell population.

According to some embodiments, improved performance in an engraftment assay can be determined by percent CD45.2+ engraftment. According to a further embodiment, improved performance in an engraftment assay can be determined by FACS analysis of the HSC population for CD45.2+CD45.1−, gating for TER119−(TER119; BioLegend).

According to some embodiments, aged HSCs maintain a bias in CD11B+GR1+ myeloid cell production at the expense of B220+CD19+ B cells and CD8+/CD4+ T cells when compared to young HSCs.

SLAM cell-surface markers delineate differentiation steps in early hematopoiesis. Originating with pluripotent hematopoietic stem cells (HSCs), differentiation steps include multipotent progenitor cells (MPPs) and lineage-restricted progenitor cells (LRPs). Each is characterized by a different complement of SLAM markers: HSCs are CD150+CD48−CD244− (CD150 AbCam (ab2604); CD48 (AbCam (ab9185); CD244 (AbCam (ab95808)); MPPs are CD150−CD48−CD244+; LRPs are CD150−CD48+CD244+. It should be noted that CD48 is a ligand for CD244, thus CD150+CD48− is sufficient to distinguish HSCs from MPPs and LRPs.

According to some embodiments, aged HSCs show an increase in hypoxia compared to Bone Marrow Endothelial Cells The bone marrow (BM) microenvironment is a complex three-dimensional structure where hematopoietic cells proliferate, mature, migrate into the sinusoidal space and enter the circulation in an exquisitely regulated fashion. The BM microenvironment, consisting of the vascular endothelial cell (EC) and perivascular stromal niches, normally provides paracrine signals to support HSC maintenance and function. Stromal cells within the BM microenvironment provide a suitable environment for self-renewal, proliferation, and differentiation of hematopoietic stem cells. BM stromal cells consisting of endothelial cells, fibroblasts, reticular cells, monocytes, osteoclasts, osteoblasts, and adipocytes secrete cytokines and produce extracellular matrix in addition to providing direct cellular contact that regulates hematopoiesis.

Bone Marrow Endothelial Cells (BMECs) are an important component of the hematopoietic microenvironment.

According to one embodiment, young BM endothelial cells are defined as $VECAD^+CD31^+Lineage^-CD45^-TER119^-$ cells.

According to some embodiments, several methods of isolating endothelial cells (ECs) from human bone marrow (BM) can be used, including fluorescence activated cell sorting (FACS) and separation by immunomagnetic beads. According to some embodiments, isolation or purification of ECs can be achieved by using conventional technologies. According to certain embodiments, bone marrow endothelial cells can be identified by FACS sorting using anti-CD31 antibody (390; Biolegend); BD Horizon PE-CF594 Mouse Anti-Human CD31), anti-CD34 antibody (Invitrogen anti-CD34 Monoclonal Antibody (BI-3C5); anti-CD34 Monoclonal Antibody (RAM34), FITC, eBioscience), anti-VE-Cadherin (VECAD) antibody (Invitrogen anti-VE-cadherin Monoclonal Antibody (BV9); Invitrogen anti-CD144 (VE-cadherin) Monoclonal Antibody (16B1), eBioscience), or manually isolated via magnetic separation using Dynabeads coated with antibodies (e.g. anti-CD31, anti-CD34, anti-VECAD). According to certain embodiments, the BMEC is CD34+. According to certain embodiments, the BMEC is CD31+. According to certain embodiments, the BMEC is VECAD+.

According to certain embodiments, to determine endothelial and stromal cell frequencies in a BM sample, flow cytometry is used with antibodies against CD31 (390; Biolegend), CD45 (30-F11; Biolegend), and TER119 (Cat No. 116211 TER119; Biolegend), where endothelial and stromal cell populations were defined as $VECAD^+CD31^+Lineage^-CD45^-TER119^-$ and $VECAD^-CD31^-Lineage^-CD45^-TER119^-$, respectively.

According to one embodiment of any of the aspects herein, the endothelial cells are derived from donor bone marrow or cord blood.

According to another embodiment of any of the aspects herein, primary endothelial cells are isolated from an individual and stable endothelial cell cultures are established as described in the Examples herein.

According to one embodiment of any of the aspects herein, the endothelial cells are derived from an aged individual (e.g. an individual 65 years of age or more). According to one embodiment of any of the aspects herein, the endothelial cells are derived from a young individual (e.g. an individual 35 years of age or less). According to one embodiment of any of the aspects herein, the endothelial cells are derived from an individual between 20 and 35 years of age.

According to another embodiment of any of the aspects herein, bone marrow endothelial cells from an aged individual have a reduced frequency of VECAD+CD31+CD45−TER119−. According to a further embodiment of any of the aspects herein, bone marrow endothelial cells from an aged individual have an increase in VECAD$^-$CD31$^-$CD45$^-$TER119$^-$ pan-BM stromal cells. According to another embodiment of any of the aspects herein, bone marrow endothelial cells from an aged individual have metabolic dysregulation, including an increase in reactive oxygen species (ROS).

According to one embodiment of any of the aspects herein, bone marrow endothelial cells isolated from an aged individual demonstrate functional alterations in vitro that are consistent with aging-related phenotype cells. For example, according to one embodiment, bone marrow endothelial cells from an aged individual have an in increase in median cellular stiffness, which can be measured, e.g., by atomic force microscopy (AFM). According to another embodiment of any of the aspects herein, bone marrow endothelial cells from an aged individual show a delay in wound healing, which is suggestive of an age-related impairment in cell migration.

According to one embodiment of any of the aspects herein, BM endothelial cells from an aged individual comprise an altered expression of pro-hematopoietic factors including, but not limited to, Kitl, Cxcl12, and Jag1. According to further embodiments of any of the aspects herein, endothelial cells from an aged individual comprise a decrease in one or more of Kitl, Cxcl12, and NOTCH ligand expression.

According to one embodiment of any of the aspects herein, the endothelial cells are derived from an individual 35 years of age or less, for example an individual 35, 34, 33, 32, 31, 30, 29, 28, 27, 26, 25, 24, 23, 22, 21, 20, 19 or 18 years of age or less. According to one embodiment of any of the aspects herein, the endothelial cells are derived from an individual 18 years of age or less, or example an individual 18, 17, 16, 15, 14, 13, 12, 11, 10, 9, 8, 7, 6, 5, 4, 3, 2, or 1 year(s) of age or less. According to some embodiments, the subject is a pediatric subject. According to one embodiment of any of the aspects herein, the endothelial cells are derived from an individual between about 20-35 years of age. According to one embodiment of any of the aspects herein, the endothelial cells are derived from an individual between about 25-35 years of age. According to one embodiment of any of the aspects herein, the endothelial cells are derived from an individual between about 30-35 years of age. According to one embodiment of any of the aspects herein, the endothelial cells are derived from an individual between about 20-30 years of age. According to one embodiment of any of the aspects herein, the endothelial cells are derived from an individual between about 20-25 years of age. According to one embodiment of any of the aspects herein, the endothelial cells are derived from an individual 30 years of age or less. According to one embodiment of any of the aspects herein, the endothelial cells are derived from a donor 25 years of age or less.

Methods
Methods of Enhancing Engraftment of HSCs

According to one aspect, the disclosed invention features a method for enhancing the engraftment capabilities of hematopoietic cells, comprising providing a hematopoietic cell population; contacting the hematopoietic cell population with endothelial cells; incubating the hematopoietic cell population and bone marrow (BM) endothelial cells for a period of time to produce a mixed hematopoietic cell/endothelial cell population; and transplanting the hematopoietic cell/endothelial cell population into a subject in need thereof, wherein engraftment of the hematopoietic cell population is increased in the subject, compared to a control hematopoietic cell population not contacted with BM endothelial cells. According to some embodiments, the control hematopoietic cell population is aged matched to the group of HSCs contacted with endothelial cells.

According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as VECAD$^+$CD31$^+$Lineage$^-$CD45$^-$TER119$^-$ cells. According to one embodiment, the endothelial cells are characterized by expression of miR-344a, miR-133b-3p, miR-294, miR-423-3p, or miR-872-3p. According to one embodiment, the period of time that the hematopoietic cell population and endothelial cells are incubated to produce a mixed hematopoietic cell/endothelial cell population is 2 hours, 4 hours, 6 hours 8 hours, 10 hours, 12 hours, 18 hours, 24 hours, 36 hours, 48 hours or more.

According to another aspect, the disclosed invention features a method for enhancing engraftment of hematopoietic stem cells in a subject in need thereof, comprising co-infusing one or more of a population of BM endothelial cells (ECs), a population of hematopoietic cells, or a mixed hematopoietic cell/BM endothelial cell population to the subject, thereby enhancing engraftment of hematopoietic stem cells. According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as VECAD$^+$CD31$^+$Lineage$^-$CD45$^-$TER119$^-$ cells. According to one embodiment, the endothelial cells are characterized by expression of miR-344a, miR-133b-3p, miR-294, miR-423-3p, or miR-872-3p.

According to one embodiment of the above aspect, the hematopoietic cell population comprises at least one of hematopoietic stem cells (HSCs), hematopoietic progenitor cells (HPCs), and CD34+ cells. According to one embodiment of the above aspects, the hematopoietic cell population is a purified population of HSCs. According to one embodiment of the above aspects, the HSCs are derived from donor bone marrow or cord blood.

According to one embodiment of the above aspects, the hematopoietic cell population comprises at least one of hematopoietic stem cells (HSCs), hematopoietic progenitor cells (HPCs), and CD34+ cells. According to another embodiment of the above aspects, the hematopoietic cell population is a purified population of HSCs. According to one embodiment, the purified population of HSCs has a higher relative proportion of CD34+ cells compared to an unpurified population. According to one embodiment, the purified population of HSCs has a higher relative proportion of CD34+ cells and Lin(-) cells compared to an unpurified population. According to some embodiments, CD34+ can be detected with FACS using anti-CD34 antibody (Invitrogen anti-CD34 Monoclonal Antibody (BI-3C5); anti-CD34 Monoclonal Antibody (RAM34), FITC, eBioscience). According to a further embodiment of the above aspects, the HSCs are derived from donor bone marrow or cord blood.

According to one embodiment, the population of endothelial cells (ECs) and the population of hematopoietic cells are administered simultaneously or sequentially.

Methods of Promoting Hematopoietic Recovery

Hematopoietic recovery in a subject refers to the reconstitution of the hematopoietic system in a subject assessed, for example by counts of red blood cells, white blood cells and/or platelets. To assess blood count recovery, differential blood counts can be measured using an automated Hematology Analyzer (e.g. Bayer ADVIA 120 Multispecies) calibrated for humans.

According to one aspect, the present disclosure features a method of promoting hematopoietic recovery in a subject undergoing a myelosuppressive regimen, comprising co-infusing one or more of a population of BM endothelial cells, a population of hematopoietic cells, or a mixed hematopoietic cell/BM endothelial cell population to the subject, thereby promoting hematopoietic recovery in the subject. According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as $VECAD^+CD31^+Lineage^-CD45^-TER119^-$ cells. According to one embodiment, the endothelial cells are characterized by expression of miR-344a, miR-133b-3p, miR-294, miR-423-3p, or miR-872-3p. Hematopoietic recovery can be assessed by red blood cell, white blood cell and/or platelet counts.

According to one embodiment, reconstitution, homing and/or proliferation of the hematopoietic cell population is increased in vivo, compared to population not contacted with endothelial cells. According to some embodiments, the control hematopoietic cell population is aged matched to the group of HSCs contacted with endothelial cells.

Methods of Reversing or Preventing Aging of HSCs

According to one aspect, the disclosure features a method of reversing the aging of a hematopoietic stem cells, comprising contacting the hematopoietic stem cells with BM endothelial cells, thereby reversing the aging of the hematopoietic stem cells. According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as $VECAD^+CD31^+Lineage^-CD45^-TER119^-$ cells. According to one embodiment, the endothelial cells are characterized by expression of miR-344a, miR-133b-3p, miR-294, miR-423-3p, or miR-872-3p. According to one embodiment, the hematopoietic stem cells exhibit improved performance in an assay selected from the group consisting of HSC engraftment, bone marrow reconstitution, and competitive transplantation.

According to another aspect, the disclosure features a method of preventing the aging of hematopoietic stem cells, comprising contacting the hematopoietic stem cells with BM endothelial cells, thereby preventing the aging of the hematopoietic stem cells. According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as $VECAD^+CD31^+Lineage^-CD45^-TER119^-$ cells. According to one embodiment, the endothelial cells are characterized by expression of miR-344a, miR-133b-3p, miR-294, miR-423-3p, or miR-872-3p.

According to one embodiment, aging of the hematopoietic stem cell is delayed. According to some embodiments, aging of a hematopoietic stem cell is prevented where aging of the hematopoietic stem cell is delayed. According to another embodiment, aging of a hematopoietic stem cell is reversed. According to certain embodiments, the aging of a hematopoietic stem cell is reversed where any property of an aging stem cell changes to be characteristic of a non-aging stem cell. Aging of a hematopoietic stem cell is delayed where, for example, characteristics or properties of an aging hematopoietic stem cell occur later than those characteristics or properties would occur for an unmanipulated stem cell. A delay in aging of a hematopoietic stem cell may be apparent when stem cells from an older adult have similar characteristics to hematopoietic stem cells from a young adult. Characteristics or properties of an aging hematopoietic stem cell and of hematopoietic stem cells from an older adult include, without limitation, decreased per cell repopulating activity, decreased self-renewal and homing abilities, myeloid skewing of differentiation, and increased apoptosis with stress, compared to hematopoietic stem cells from a hematologically normal young bone marrow sample.

According to another aspect, the disclosure features a method for promoting hematopoietic stem cell maintenance, comprising contacting the hematopoietic stem cells with BM endothelial cells, wherein the hematopoietic stem cell continues to self-renew. According to one embodiment, the BM endothelial cells are expanded in culture prior to contact with the hemaptopoietic cell population. According to one embodiment, contacting the hematopoietic cell population with BM endothelial cells includes direct contact of the hematopoietic stem cells to the bone marrow endothelial cells, or proximity of the hematopoietic stem cells to the BM endothelial cells. According to one embodiment, the BM endothelial cells are defined as $VECAD^+CD31^+Lineage^-CD45^-TER119^-$ cells. According to one embodiment, the endothelial cells are characterized by expression of miR-344a, miR-133b-3p, miR-294, miR-423-3p, or miR-872-3p. According to some embodiments, self-renewal of hematopoietic stem cells is division of the hematopoietic stem cell with maintenance of the undifferentiated state. Assays to measure the self-renewal capabilities of stem cells include, without limitation, a serial dilution assay, a colony-forming unit assay, a long-term culture assay, and a secondary neurophore formation assay. According to one embodiment, the hematopoietic stem cells are aging stem cells.

According to one embodiment, the hematopoietic stem cells are in an animal. According to a further embodiment, the animal is a human.

Aging hematopoietic stem cells may exhibit one or more of the following properties or characteristics compared to hematopoietic stem cells from a hematologically normal young bone marrow sample: decreased per cell repopulating activity, decreased self-renewal and homing abilities, myeloid skewing of differentiation, and increased apoptosis with stress (Janzen et al., Nature, 2006, v. 443, p. 421). Thus, in some embodiments, aging of the hematopoietic stem cell is prevented, delayed or reversed when the hematopoietic stem cell exhibits one or more of the following characteristics: reduced occurrence of cell death, increased quiescence, increased occurrence of self-renewal, increased ability to repopulate its organ or tissue of origin, increased homing ability, a change in differentiation profile, decreased transcriptional activity, decreased cell size, decreased mitochondrial metabolic activity, and a change in chromatin profile. Any methods known in the art to evaluate these properties may be used to identify whether the aging of a stem cell is prevented, delayed or reversed. For example, assays such as competitive repopulation assays and transplantation, engraftment, colony-forming unit assays, long-term culture assays, cell proliferation assays such as BrdU or EdU incorporation, transcriptional profiling by microarray analysis, chromatin immunoprecipitation sequencing (ChIP-seq), cellular ATP measurements, secondary neurophore formation assays, secondary neurophore differentiation assays, and caspase activity assays may be used. Description of these assays and others may be found, for example, in the following publications: Mohrin et al., Science 347, 1374 (Mar. 20, 2015); Tang, Rando, EMBO J. 33, 2782 (Dec. 1, 2014); Rodgers et al., Nature 510, 393 (Jun. 19, 2014); Liu, et al., Cell Rep. 4, 189 (Jul. 11, 2013); Renault et al., Cell Stem Cell. 5, 527 (Nov. 6, 2009); Webb et al., Cell Rep. 4, 477 (Aug. 15, 2013); Keyes et al., PNAS 110, E4950 (Dec. 17, 2013); Hsu et al., Nat. Med. 20, 847 (August 2014).

In some embodiments, aging of the hematopoietic stem cell is prevented, delayed or reversed where the hematopoietic stem cell exhibits improved performance in an assays such as HSC engraftment, bone marrow reconstitution, or competitive transplantation. These assays measure the ability of transplanted hematopoietic stem cells to gain access to the bone marrow of an irradiated recipient animal, take up residence in the bone marrow, undergo self-renewing cell division to produce a larger pool of hematopoietic stem cells, and differentiate to generate different cell types (See, e.g., J. Clin Invest. 2002; 110(3): 303-304). In some embodiments where the stem cell is in a human, prevention, delay or reversal of hematopoietic stem cell aging is detected by drawing and testing blood. Blood drawn from a human where hematopoietic stem cell aging has been prevented, delayed or reversed does not exhibit one or more of the following characteristics typical of aging, such as increased myeloid differentiation, fewer lymphoid cells, or anemia. Myeloid differentiation, lymphoid cells, and anemia may be measured with standard assays known in the art (See, e.g., Pang et al., PNAS 108, 20012 (Dec. 13, 2011). According to one embodiment, aging HSCs exhibit diminished capacity to give rise to lymphoid B lineage cells (CD19+(Invitrogen Cat #MHCD1901) compared to a hematologically normal young bone marrow sample. According to one embodiment, aging HSCs exhibit an increased myeloid-to-lymphoid ratio, as a result of a decreased efficiency in the generation of lymphoid B lineage cells by aged HSC compared to a hematologically normal young bone marrow sample. According to one embodiment, FACS is used to determine CD13+ and/or CD33+ myeloid versus CD19+ B-lymphoid distribution (with CD45+ gating). According to some embodiments, aging HSCs up-regulate genes that specify myeloerythroid fate and function (e.g. HOXA9, FUT1, CSF2RB, CCDC88A, USP46, F2RL1, PTGS1, MICAL3, SELP, and ANXA3), and down-regulate genes associated with lymphopoiesis (e.g. EMP1, SOX4, ADA, FLT3, DUSP1, CISH, DUSP6 and TSC22D3).

Methods of Preparing

According to another aspect, the present disclosure provides a method of preparing an endothelial cell vascular niche effective for maintaining functional HSCs, the method comprising providing a hematopoietic cell population; contacting the hematopoietic cell population with endothelial cells; and incubating the hematopoietic cell population and endothelial cells for a period of time to produce a mixed hematopoietic cell/endothelial cell population; wherein the functional HSCs are characterized by one or more of (i) improved performance in an HSC engraftment assay; (ii) improved bone marrow reconstitution; (iv) improved hematopoietic recovery; (v) increased repopulating activity; and (vi) improved self-renewal, compared to a control hematopoietic stem cell population. According to one embodiment, the endothelial cells are expanded in culture prior to contact with the hemaptopoietic cell population. According to one embodiment, the expanded endothelial cells are CD34+/CD38− or CD34+/CD45+. According to some embodiments, the BM vascular niche supports young HSC homeostasis in vivo through the expression of prohematopoietic factors such as Kitl, Cxcl12, and Jag1.

According to one embodiment, the period of time that the hematopoietic cell population and endothelial cells are incubated to produce a mixed hematopoietic cell/endothelial cell population is 2 hours, 4 hours, 6 hours 8 hours, 10 hours, 12 hours, 18 hours, 24 hours, 36 hours, 48 hours or more.

According to one embodiment, the hematopoietic cell population is a purified population of HSCs. According to one embodiment, the purified population of HSCs has a higher relative proportion of CD34+ cells compared to an unpurified population. According to one embodiment, the purified population of HSCs has a higher relative proportion of CD34+ cells and Lin(−) cells compared to an unpurified population. According to another embodiment, the HSCs are derived from donor bone marrow or cord blood. According to a further embodiment, the control hematopoietic stem cell population comprises aged HSCs.

Methods of Treatment

According to one aspect, the disclosure features a method of treating a subject who has received a hematopoietic stem cell transplant comprising hematopoietic stem cells and/or progenitor cells, comprising co-infusing one or more of: a population of bone marrow endothelial cells, a population of hematopoietic cells, or a mixed hematopoietic cell/endothelial cell population to the subject, thereby treating the subject. According to one embodiment, the hematopoietic cell population comprises at least one of hematopoietic stem cells (HSCs), hematopoietic progenitor cells (HPCs), and CD34+ cells. According to another embodiment, the hematopoietic cell population is a purified population of HSCs. According to a further embodiment, the HSCs are derived from donor bone marrow or cord blood. According to one embodiment, the population of endothelial cells (ECs) and the population of hematopoietic cells are administered simultaneously or sequentially.

According to some embodiments, patients of all ages will benefit from the therapeutic method disclosed herein.

According to some embodiments, a patient greater than 65 years of age (e.g. 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96. 97, 98, 99 years of age or greater) suffer severe side effects to current chemotherapeutic regimens and they will likely receive the greatest benefit from the present method.

The therapeutic benefits provided by the aspects of the disclosure include, for example, reduced duration and/or extent of cytopenias (including neutropenia and/or thrombocytopenia), improved white blood cell, red blood cell, and platelet counts in the peripheral blood, preserved HSC function, and improved integrity of the BM endothelial niche following the myelosuppressive regimen.

According to any of the foregoing embodiments, a sample containing the hematopoietic cell population is derived from and optionally processed to expand the number of stem cells within the sample, in vitro, prior to administering to the subject the hematopoietic stem cell population or a mixed hematopoietic cell/endothelial cell population. In any of the foregoing embodiments, a sample containing the hematopoietic stem cells is derived and optionally processed to increase the percentage of stem cells within the sample, in vitro, prior to administering to the subject the hematopoietic stem cells. The sample can be autologous or not. In any of the foregoing embodiments, at least 5, 10, 15, 20, 25, 30, 35, 40, 45, or 50% of the hematopoietic stem cells are CCR2 positive (CCR2$^+$) (Abiotech 250580), CD34 positive (CD34+) (Invitrogen anti-CD34 Monoclonal Antibody (BI-3C5); anti-CD34 Monoclonal Antibody (RAM34), FITC, eBioscience), and/or lineage negative (lin−) cells. In any of the foregoing embodiments, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50% of the hematopoietic stem cells are CCR2 positive (CCR2+) (Abiotech 250580), CD34 positive (CD34+) (Invitrogen anti-CD34 Monoclonal Antibody (BI-3C5); anti-CD34 Monoclonal Antibody (RAM34), FITC, eBioscience), and/or lineage negative (lin−) cells. In any of the foregoing embodiments, between about 20% and 98%, e.g., about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the hematopoietic stem cells for administration to the subject are CCR2 positive (CCR2+), CD34 positive (CD34+), or lineage negative (lin−). lin(−) cells can be identified by FITC-conjugated lineage markers (e.g. Ter119 (Cat No. 116211 TER119; Biolegend)), where no staining indicated lin(−) cells.

Combination Treatment

According to one embodiment of any of the aspects herein, the endothelial cells are administered with the hematopoietic cells (e.g. a hematopoietic cell/endothelial cell population as described herein). According to another embodiment, the endothelial cells are administered alone. According to some embodiments, the hematopoietic cell/endothelial cell population or the endothelial cells are administered with an additional agent prior to, concurrently with, or after transplantation. According to one embodiment of any of the aspects herein, the additional agent is a chemotherapeutic. According to another embodiment, the chemotherapeutic drug or a combination of drugs, includes, but is not limited to, Capecitabane (Xeloda), Carboplatin (Paraplatin), Cisplatin (CDDP), Cisplatin (Platinol), Cyclophosphamide (Cytoxan), Cytarabine, Docetaxel (Taxotere), Doxorubicin (Adriamycin), Etoposide (VePesid), Floxuridine (FUDR), 5-flurouracil, Gemcitibine, Ifosfamide (Ifex) Iressa, Irinotecan (Camptosar), Mitomycin (Mutamycin) Navelbine, Oxaliplatin (Eloxatin), Paclitaxel (Abraxane), Paclitaxel (Taxol), Pemetrexed (Alimta) Temozolomide, Topotecan (Hycamtin). Examples of combinations of chemotherapeutic drugs for treating cancers include Leucovorin/Floxuridine/Cisplatin/Mitomycin, Pemetrexed/Cisplatin/Cetuximab, Docetaxel/Carboplatin, Docetaxel/Carboplatin, Pemetrexed/Cisplatin, Leucovorin/Floxuridine, Cetuximab/Irinotecan, Pemetrexed/Cisplatin, Docetaxel/Carboplatin, Paclitaxel/Carbolplatin, Leucovorin/Floxuridine/Topotecan, Leucovorin/Floxuridine/Topotecan, Leucovorin/Floxuridine/Cetuximab/Mitomycin, Leucovorin/Floxuridine/Cisplatin/Mitomycin, Leucovorin/Floxuridine/Cisplatin/Mitomycin, Leucovorin/Floxuridine/Oxaliplatin, Docetaxel/Carboplatin/Pemetrexed/Cisplatin, Docetaxel/Carboplatin, Cetuximab/Irinotecan, Doxorubicin/Cyclophosphamide, Docetaxel/Carboplatin, Pemetrexed, Capecitabane, Capecitabane/Oxaliplatin/Irinotecan, Docetaxel, Etoposide/Trastuzumab/Zoledronic Acid/Carboplatin/Mesna/Ifosfamide, and Leucovorin/Floxuridine/Cisplatin/Mitomycin. According to one embodiment, the chemotherapy is high dose chemotherapy, which refers to a dosage and intensity of chemotherapy which is regarded as "high-dose" when a significant myelosuppression follows with significantly reduced peripheral blood leukocyte and platelet counts and an increased risk of infection. According to another embodiment, the chemotherapy is myelosupressive chemotherapy. Myelosupressive chemotherapy refers to the effect of the chemotherapy on bone marrow functions. A chemotherapy is myelosuppressive when the peripheral blood leukocyte counts and possibly platelet counts decrease for a limited period of time and recover thereafter spontaneously or under hematopoietic growth factor stimulation. Depending on the degree of myelosuppression there can be an increased risk of infection. According to a further embodiment, the myelosupressive therapy comprises cyclophosphamide, etoposide, carmustine, cytarabine, melphalan, busulfan, doxorubicin, epirubicin, paclitaxel, docetaxel, thiotepa, fludarabine, vincristine, bendamustine, cisplatin, carboplatin, daunorubicin, fluorouracil, gemcitabine, idarubicin, ifosfamide, irinotecan, methotrexate, mitoxantrone, oxaliplatin, treosulfan, vinblastine, vinorelbine.

According to another embodiment of any of the aspects herein, the additional agent is radiation therapy (or radiotherapy). Radiation therapy refers to any therapeutic application of ionic radiation. The radiation may be radioactive radiation including fast electrons, neutrons, protons, or Pi-mesons, microwaves, IR, and UV radiation. Preferably, said radiation is used to treat cancer or malignant hematopoietic diseases.

According to a further embodiment of any of the aspects herein, the additional agent is a myelosuppresive regimen or therapy, for example, but not limited to, peginterferon alfa-2a, interferon alfa-n3, peginterferon alfa-2b, aldesleukin, gemtuzumab ozogamicin, interferon alfacon-1, rituximab, ibritumomab tiuxetan, tositumomab and alemtuzumab.

According to any of the foregoing embodiments, the method further comprises administering a hematopoietic stem cell mobilizing agent to the subject. According to one embodiment, the mobilizing agent is granulocyte-macrophage colony-stimulating factor (GM-CSF), granulocyte colony-stimulating factor (G-CSF), PEGylated G-CSF (pegfilgratism), lenogratism, a glycosylated form of G-CSF, C—X—C motif chemokine 2 (CXCL2), C—X—C chemokine receptor type 4 (CXCR-4), or plerixafor.

According to some embodiments, the endothelial cells or the hematopoietic cell/endothelial cell population may be administered to the subject after completion of chemotherapy treatment. In such embodiments, the hematopoietic stem cells may be administered to the subject within six weeks after completion of chemotherapy or radiation treatment. In such embodiments, the endothelial cells or the hematopoietic cell/endothelial cell population may be administered to the subject zero days, one day, two days, three days, four days, five days, six days, one week, two weeks, three weeks, four weeks, five weeks, or six weeks after completion of chemotherapy or radiation treatment.

According to any of the foregoing embodiments, the endothelial cells or the hematopoietic cell/endothelial cell population can be treated with one or more different cytokines before administration of the hematopoietic stem cells to the subject. According any of the foregoing embodiments, the endothelial cells or the hematopoietic cell/endothelial cell population can be administered to the subject concurrently with one or more different cytokines. According to any of the foregoing embodiments, the endothelial cells or the hematopoietic cell/25 endothelial cell population are treated with one or more cytokines on the same day as, 1 day before, 2 days before, 3 days before, 4 days before, or 5 days before administration to the subject. In any of the foregoing embodiments, the endothelial cells or the hematopoietic cell/endothelial cell population are treated with one or more cytokines for 1, 2, 3, 4, or 5 days, before administration to the subject.

According to any of the foregoing aspects, one or more different immune checkpoint inhibitors can be used concurrently in combination with endothelial cells or the hematopoietic cell/endothelial cell population and/or a hematopoietic stem cell mobilizing agent for treatment of a subject having cancer or an infectious disease. For example, the immune checkpoint inhibitor can be an antagonist of programmed death 1 (PD-1), programmed death ligand 1 (PD-L1), cytotoxic T-lymphocyte-associated antigen 4 (CTLA-4), V-domain Ig suppressor of T cell activation (VISTA), programmed death ligand 2 (PD-L2), indoleamine 2,3-dioxygenase (IDO), arginase, B7 family inhibitory ligand B7-H3, B7 family inhibitory ligand B7-H4, lymphocyte activation gene 3 (LAG3), 2B4, B and T lymphocyte attenuator (BTLA), T cell membrane protein 3 (TIM3), adenosine Ata receptor (A2aR), and/or a killer inhibitory receptor.

According to any of the foregoing embodiments, adoptive cell therapy (ACT) also can be administered to the subject. In any of the foregoing embodiments, the adoptive cell therapy (ACT) is administered to the subject close enough in time with at least one of the said treatments to enhance treatment of the disease.

Subjects

According to some embodiments, a subject of the disclosed invention includes anyone who is a candidate for autologous stem cell or bone marrow transplantation during the course of treatment for malignant disease or as a component of gene therapy. Other possible candidates are subjects who donate stem cells or bone marrow to subjects for allogeneic transplantation for malignant disease or gene therapy. Subjects may have undergone irradiation therapy, for example, as a treatment for malignancy of cell type other than hematopoietic. Subjects may be suffering from anemia, e.g., sickle cell anemia, thalessemia, aplastic anemia, or other deficiency of HSC derivatives.

According to one embodiment, the subject has previously been treated with a myelosuppressive regimen; the subject is currently being treated with a myelosuppresive regimen; or the subject will undergo treatment with a myelosuppressive regimen. According to one embodiment, the myelosuppressive regimen comprises chemotherapy or radiation.

According to one embodiment, the subject is 65 years or more in age, e.g. 65, 66, 67, 68 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 years of age or more.

According to one embodiment, the subject has bone marrow disease. According to one embodiment, a bone marrow disease is a disease characterized by abnormal or decrease function of stem cells and/or stem cell development. According to another embodiment, a bone marrow disease refers to a disease in which the normal bone marrow architecture is displaced by malignancies, sickle cell disease, myelodysplastic syndrome, myeloproliferative disorders, aplastic anaemia, or infections leading to a decrease in the production of blood cells and blood platelets. Said bone marrow disease can be for example leukemia, a defect of the blood cell compartment or a need for bone marrow transplantation after chemotherapy or irradiation treatment. In some embodiments, the defect of the blood cell compartment can be a hemoglobinopathy like thalassaemia, defects in neutrophil granulocyte function, a defect in neutrophil granulocyte function, a defect in T- and/or B-lymphocytes, e.g., severe combined immunodeficiency, Bruton's agammaglobulinemia. In some embodiments, the bone marrow disease is aplastic anemia. In aplastic anemia the bone marrow doesn't make red blood cells. In some embodiments, the bone marrow disease is a myeloproliferative disorder. In myeloproliferative disorders, the bone marrow makes too many white blood cells. In some embodiments, the bone marrow disease is a lymphoma, a cancer of a part of the immune system called the lymph system. According to one embodiment, the lymphoma spreads into the bone marrow and affect the production of blood cells. According to one embodiment, the bone marrow disease is selected from the group consisting of leukemia, a defect of the blood cell compartment, and a bone marrow disease induced by chemotherapy or irradiation. According to a further embodiment, the subject has a secondary bone marrow disease, which encompasses those diseases and disorders where the bone marrow becomes involved secondarily like in case of bone marrow metastases of a cancer.

According to one embodiment, the subject has cancer.

According to one embodiment, the subject has an autoimmune disorder. According to one embodiment, an autoimmune disease refers to those diseases which are associated with the presence of autoantibodies in a subject. Examples for said diseases include, but are not limited to, rheumatoid arthritis or lupus erythematosus.

Effective Amount

Subjects are treated with effective amounts of the solutions of the disclosure. An "effective amount" of an agent generally refers to an amount sufficient to elicit the desired biological response, i.e., treat the condition. As will be appreciated by those of ordinary skill in the art, the effective amount of an agent described herein may vary depending on such factors as the condition being treated, the mode of administration, and the age, body composition, and health of the subject.

For therapeutic treatment, an effective amount is an amount sufficient to provide a therapeutic benefit in the treatment of a condition or to reduce or eliminate one or more symptoms associated with the condition. This may encompass an amount that improves overall therapy, reduces or avoids symptoms or causes of the condition, or enhances the therapeutic efficacy of another therapeutic agent.

An exemplary effective amount of hematopoietic stem cells for injection is about $2 \times 10^6$ cells per kilogram (kg) body weight of the subject. Exemplary effective amounts of hematopoietic stem cells for injection can range above and below this amount. Examples include from about 1, 1.5, 2, 2.5, 3, 3.5, 4, 4.5, 5, 5.5, 6, 6.5, or $7 \times 10^6$ cells/kg.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which can independently be included in the smaller ranges is also encompassed within the invention, subject to any specifically excluded limit in the stated range. Where the stated range includes one or both of the limits, ranges excluding either both of those included limits are also included in the invention.

Unless otherwise defined, all technical and scientific terms used herein have the same meaning as commonly understood by one of ordinary skill in the art to which this invention belongs. Although methods and materials similar or equivalent to any of those described herein can be used in the practice of the invention, exemplary methods and materials are described below. In addition, the materials, methods, and examples are illustrative only and not intended to be limiting.

The publications discussed herein are provided solely for their disclosure prior to the filing date of the present application and each is incorporated by reference in its entirety. Nothing herein is to be construed as an admission that the described invention is not entitled to antedate such publication by virtue of prior invention. Further, the dates of publication provided may be different from the actual publication dates which may need to be independently confirmed.

EXAMPLES

The Examples described herein illustrate several advantages of the described invention and are not intended to limit the scope of what the inventors regard as the invention, nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, parts are by weight, molecular weight is weight average molecular weight, temperature is in degrees Centigrade, and pressure is at or near atmospheric.

In summary, the results described herein demonstrate that an age-dependent dysregulation of the BM endothelial niche is sufficient to disrupt the homeostatic HSC supportive microenvironment and drive aging-associated hematopoietic phenotype cells. Using an established ex vivo co-culture system, the results described herein demonstrate that culture of young hematopoietic stem and progenitor cells (HSPCs) on aged endothelium inhibit long-term HSC repopulating activity in a competitive transplantation setting and promote a myeloid bias at the expense of B cell and T cell lymphopoiesis. Moreover, aged HSPCs cultured on young endothelium demonstrate marked increase in hematopoietic reconstitution. These results extend to endothelial infusions in young and aged mice, in which aged BM-derived ECs fail to support endogenous hematopoietic recovery following myelosuppressive irradiation and impart a myeloid bias in young mice; conversely, young EC infusions enhance HSC activity and increase B cell and T cell output in young and aged animals. Moreover, young EC co-infusions enhance aged HSC transplantation (HSCT) and overall survival in a limiting dilution setting through protection of the endogenous BM vascular niche.

Example 1. Methods

Examples 2-8 were carried out using, but not limited to, the following methods:

Mice

Young and aged C57BL/6 (CD45.2) mice were purchased from the National Institute on Aging and Taconic Biosciences and used as further described. B6.SJL-Pqvc$^a$Pepc$^b$/BoyJ (CD45.1) mice were purchased from The Jackson Laboratory and used as further described. All animals were maintained in specific-pathogen-free housing and used at indicated ages. For hematopoietic recovery, reconstitution and endothelial cell (EC) transplantation studies, mice were subjected to total body γ-irradiation ($^{137}$Cs) 24 hrs prior to transplantation at indicated doses. Transplant recipients were given PicoLab Mouse 20 antibiotic feed (0.025% Trimethoprim and 0.124% Sulfamethoxazole; LabDiet) 24 hrs prior to irradiation and subsequently maintained for 28 days.

Femur Immunohistochemistry

Young (3 month) and aged (24 month) mice were intravitally-labeled for 10 min with 25 μg Alexa Fluor 647-conjugated VECAD antibody (BV13; Biolegend) via retro-orbital injection. Following labeling, mice were sacrificed and perfused via intracardiac PBS (pH 7.2) injection. Femurs were fixed overnight in 4% paraformaldehyde (PFA) in PBS (pH 7.2), decalcified in 10% EDTA for 72 hrs at room temperature, cryopreserved in 30% sucrose for 48 hrs at 4° C., and embedded in 50% optimal cutting temperature (OCT; Tissue-Tek) and 50% sucrose. Longitudinal femur sections (12 μm) were cut using a CM 3050S Cryostat (Leica), counter-stained with 1 μg/mL 4-6, Diamidino-2-Phenylindole (DAPI) (Biolegend), and mounted using Prolong Gold anti-fade solution (Life Technologies). Femur sections were imaged on a LSM 710 confocal microscope (Zeiss).

Flow Cytometry and Cell Sorting

Before cell staining, $F_c$ receptors were blocked with a CD16/32 antibody (93; Biolegend) in PBS (pH 7.2) containing 0.5% BSA (Fraction V) and 2 mM EDTA for 10 mins at 4° C. $F_c$-blocked samples were stained in PBS (pH 7.2) containing 0.5% BSA (Fraction V) and 2 mM EDTA for 30 mins at 4° C. with fluorochrome-conjugated antibodies according to the manufacturer's recommendation. Stained cells were washed in PBS (pH 7.2) containing 0.5% BSA (Fraction V) and 2 mM EDTA and fixed in 1% PFA in PBS (pH 7.2) with 2 mM EDTA for flow analysis or resuspended in PBS (pH 7.2) with 2 mM EDTA and 1 μg/mL DAPI (Biolegend) for cell sorting. Samples were analyzed using a LSR II SORP (BD Biosciences) and sorted using an ARIA II SORP (BD Biosciences). Data was collected and analyzed using FACs DIVA 8.0.1 software (BD Biosciences).

Endothelial and Stromal Cell Quantification

Young (3 month) and aged (24 month) C57BL/6 mice were intravitally-labeled for 10 min with 25 μg Alexa Fluor 647-conjugated VECAD antibody (BV13; Biolegend) via retro-orbital injection. Mice were sacrificed and femurs were crushed using a mortar and pestle, and whole bone marrow was enzymatically disassociated in Hanks Balanced Salt Solution (Life Technologies) containing 20 mM HEPES (CellGro), 2.5 mg/mL Collagenase A (Roche), and 1 Unit/mL Dispase II (Roche) for 15 mins at 37° C. with gentle agitation. Cell suspensions were filtered (40 µm), washed in PBS (pH 7.2) containing 0.5% BSA (Fraction V) and 2 mM EDTA, and depleted of terminally-differentiated hematopoietic cells using a murine hematopoietic Lineage Cell Depletion Kit (Miltenyi Biotec) according to the manufacturer's recommendations. To determine endothelial and stromal cell frequencies via flow cytometry, resulting cell suspensions were stained using antibodies against CD31 (390; Biolegend), CD45 (30-F11; Biolegend), and TER119 (TER119; Biolegend); endothelial and stromal cell populations were defined as $VECAD^+CD31^+Lineage^-CD45^-TER119^-$ and $VECAD^-CD31"Lineage^-CD45^-TER119^-$, respectively.

Vascular Permeability

To measure bone marrow vascular integrity, Evans Blue Dye (Sigma Aldrich) 0.5% w/v in PBS (pH 7.2) was infused via tail vein injection into young (3 month) and aged (19 month) C57BL/6 mice at 25 mg dye/kg total body weight. Three hours post injection, mice were sacrificed via cervical dislocation and cardiac perfused with 10 mL PBS (pH 7.2). Femurs were removed, denuded of excess tissue, and weighed. To extract Evan's Blue Dye, resulting femurs were crushed using a mortar and pestle in 600 µL formamide and incubated at 55° C. overnight. Femurs from non-injected mice were used as baseline controls. Following extraction, samples were briefly vortexed and centrifuged at 16,000 g for 5 min at room temperature. Supernatant absorbance (Abs) was recorded at 620 nm and 740 nm. Sample Abs was corrected for Heme-containing proteins [$Abs_{620}-(1.426 \times Abs_{740}+0.03)$] and blanked using non-injected controls [corrected sample $Abs_{620}$–corrected non-injected control $Abs_{620}$]. Total Evan's Blue Dye was determined using a standard curve and normalized to femur weight.

Reactive Oxygen Species

To examine reactive oxygen species, young (3 month) and aged (24 month) C57BL/6 mice were intravitally-labeled for 10 min with 25 µg Alexa Fluor 647-conjugated VECAD antibody (BV13; Biolegend) via retro-orbital injection. Mice were sacrificed and femurs were crushed using a mortar and pestle, and whole bone marrow was enzymatically disassociated in Hanks Balanced Salt Solution (Life Technologies) containing 20 mM HEPES (CellGro), 2.5 mg/mL Collagenase A (Roche), and 1 Unit/mL Dispase II (Roche) for 15 mins at 37° C. with gentle agitation. Cell suspensions were filtered (40 µm), washed in PBS (pH 7.2) containing 0.5% BSA (Fraction V) and 2 mM EDTA, and depleted of terminally-differentiated hematopoietic cells using a murine hematopoietic Lineage Cell Depletion Kit (Miltenyi Biotec) according to the manufacturer's suggestions. Cell suspensions were stained using antibodies against CD31 (390; Biolegend), CD45 (30-F11; Biolegend), and TER119 (TER119; Biolegend). Stained cell suspensions were then incubated with 5 µM CM-H2DCFDA (ThermoFisher Scientific) in PBS at 37° C. for 20 min, washed with PBS (pH 7.2) containing 0.5% BSA (Fraction V) and 2 mM EDTA, and incubated at 37° C. for 15 min. Endothelial populations were defined as $VECAD^+CD31^+Lineage^-CD45^-TER119^-$. ROS levels were estimated using Flow Cytometry.

Hypoxyprobe

To evaluate bone marrow oxygenation status, young (3 month) and aged (24 month) C57BL/6 mice were intraperitoneally injected with 120 mg/kg of 100 mg/mL Pimonidazole HCl (Hypoxyprobe-1; Hypoxyprobe, Inc.). Following 90 min, mice were intravitally-labeled for 10 min with 25 µg Alexa Fluor 647-conjugated VECAD antibody (BV13; Biolegend) via retro-orbital injection. For bone marrow EC analysis by flow cytometry, mice were sacrificed and femurs were crushed using a mortar and pestle. Whole bone marrow was enzymatically disassociated in Hanks Balanced Salt Solution (Life Technologies) containing 20 mM HEPES (CellGro), 2.5 mg/mL Collagenase A (Roche), and 1 Unit/mL Dispase II (Roche) for 15-30 mins at 37° C. with gentle agitation. Cell suspensions were filtered (40 µm), washed in PBS (pH 7.2) containing 0.5% BSA (Fraction V) and 2 mM EDTA, and depleted of terminally-differentiated hematopoietic cells using a murine hematopoietic Lineage Cell Depletion Kit (Miltenyi Biotec) according to the manufacturer's recommendations. Resulting cell suspensions were stained using antibodies against CD31 (390; Biolegend), CD45 (30-F11; Biolegend), and TER119 (TER119; Biolegend). Following cell surface staining, cells were fixed and permeabilized using the BD Cytofix/Cytoperm Kit (BD Biosciences) and stained with a monoclonal antibody raised against pimonidazole adducts at a 1:100 dilution (HP-Red549; Hypoxyprobe, Inc.) according to the manufacturer's suggestions. Endothelial populations were defined as $VECAD^+CD31^+Lineage^-CD45^-TER119^-$.

For bone marrow immunohistochemical analysis, mice were sacrificed and femurs were fixed in 4% PFA in PBS (pH 7.2) overnight at 4° C., washed in PBS (pH 7.2), and decalcified for 72 hrs in 10% EDTA in PBS (pH 7.2) at room temperature with gentle rocking. Femurs were next washed in PBS (pH 7.2), cryopreserved in 30% sucrose for 48 hrs at 4° C., and embedded in 50% optimal cutting temperature (OCT; Tissue-Tek) and 50% sucrose. Longitudinal femur sections (12 µm) were cut using a CM 3050S Cryostat (Leica), permeabilized in blocking buffer (10% normal donkey serum (Jackson ImmunoResearch) and 0.1% Triton X-100 in PBS, pH 7.2) for 30 min at room temperature, and incubated with a monoclonal antibody raised against pimonidazole adducts at a 1:100 dilution in blocking buffer (HP-Red549; Hypoxyprobe, Inc.) overnight at 4° C. Sections were washed in blocking buffer and counter-stained with 1 µg/mL DAPI (Biolegend), and mounted using Prolong Gold anti-fade solution (Life Technologies). Femur sections were imaged on a LSM 710 confocal microscope (Zeiss).

Akt1 Lentivirus

Lentivirus (21) was generated by co-transfecting pCCL-myrAkt1 backbone (13 µg) with RRE (5 µg), REV (2.5 µg), and VSV-G (3 µg) packaging plasmids into a 10 cm plate of 80% confluent 293T/17 cells (ATCC) using Lipofectamine 2000 (Life Technologies) according to the manufacturer's suggestions. Forty-eight hrs post-transfection, supernatants were processed using Lenti-X Concentrator (ClonTech) according to the manufacturer's recommendations. Resulting myrAkt1-expressing lentivirus was resuspended in 0.5 mL THE Buffer (50 mM Tris, pH 8.0, 1 mM EDTA, 130 mM NaCl), and stored at −80° C. Viral titers were determined using Lenti-X p24 Rapid Titer Kit (ClonTech). All transductions were done using 10,000 pg virus per 30,000 $ECs/cm^2$.

Endothelial Cell Isolation

Primary murine endothelium was generated from young (3 month) and aged (24 month) C57BL/6 mice. To establish stable endothelial cultures, long bones were denuded of excess tissue and crushed using a mortar and pestle and lungs were removed and minced with a surgical scalpel. Tissues were enzymatically disassociated in Hanks Balanced Salt Solution (Life Technologies) containing 20 mM HEPES (CellGro), 2.5 mg/mL Collagenase A (Roche), and 1 Unit/mL Dispase II (Roche) for 15 mins at 37° C. with gentle agitation. Cell suspensions were filtered (40 µm), washed in PBS (pH 7.2) containing 0.5% BSA (Fraction V) and 2 mM EDTA, and depleted of terminally-differentiated hematopoietic cells using a murine hematopoietic Lineage Cell Depletion Kit (Miltenyi Biotec) according to the manufacturer's recommendations. Endothelium were immunopurified from resulting cell suspensions using Dynabeads (Life Technologies) pre-captured with a monoclonal CD31 antibody (MEC13.3; Biolegend). Briefly, $4 \times 10^6$ sheep anti-rat IgG Dynabeads were incubated with 10 µg of CD31 antibody (per isolation) in 0.5 mL PBS (pH 7.2) containing 0.5% BSA (Fraction V) and 2 mM EDTA for 30 mins at 4° C. Antibody-captured beads were washed three times in 1 mL PBS (pH 7.2) containing 0.5% BSA (Fraction V) and 2 mM EDTA according to the manufacturer's suggestions. CD31-Dynabeads were then added to lineage-depleted cell suspensions in a final volume of 1 mL, and incubated for 30 mins at 4° C. $CD31^+$ cells were captured and washed five times in 1 mL PBS (pH 7.2) containing 0.5% BSA (Fraction V) and 2 mM EDTA using a DynaMag-2 magnet (Life Technologies), plated and grown on fibronectin-coated (Sigma-Aldrich) 12-well plates (Fisher Scientific). Endothelium were cultured in endothelial growth media, composed of low-glucose DMEM (Life Technologies) and Ham's F-12 (CellGro) (1:1 ratio), supplemented with 20% heat-inactivated FBS, antibiotic-antimycotic (CellGro), non-essential amino acids (CellGro), 10 mM HEPES (CellGro), 100 µg/mL heparin (Sigma-Aldrich), and 50 µg/mL endothelial mitogen (Biomedical Technologies, Inc). To select for Akt1-expressing ECs, cultures were grown for seven days in serum- and cytokine-free StemSpan SFEM (StemCell Technologies, Inc.) media. Cells were maintained and cultured in EC growth media in humidified incubators at 37° C. under 5% $CO_2$. All endothelial lines were subsequently stained and sorted for $VECAD^+$ (BV13; Biolegend), $CD31^+$ (390; Biolegend), $CD45^-$ (30-F11; Biolegend) populations to ensure purity. Phase contrast images were derived using a Evos XL (AMG) cell imaging system. For immunocytochemistry, young and aged endothelium were stained with an antibody raised against VECAD (BV13; Biolegend), counter-stained with 1 µg/mL DAPI (Biolegend), and imaged using an LSM 710 confocal microscope (Zeiss).

Atomic Force Microscopy

Cultured endothelium from young (3 month) and aged (24 month) C57BL/6 mice (as described above) were grown to 80-90% confluency on fibronectin-coated (Sigma-Aldrich) 60 mm dishes (Corning), fixed in 4% PFA in PBS (pH 7.2) for 15 mins at room temperature, and washed in PBS (pH 7.2). Force maps were generated with an MFP-3D Bio Atomic Force Microscope (Asylum Research) using a TR400PB pyramidal silicon nitride tip (k=0.02 N/m, h=3) and composed of a 32×32 grid (1,024 force curves) covering 90 µm². Force curves were taken by 250 nm indentation with a trigger point of 200 pN at 600 nm/s; initial 100 nm were fitted to the Hertz-Sneddon Model (53). Images were taken using an MLCT probe (Bruker) in a 90 µm² area with 256 points and lines resolution. Igor Pro 6.34A software (Asylum Research) was used to determine the cantilever spring constant via thermal tune calibration. Median endothelial stiffness is presented as a box plot. Relative stiffness was calculated by normalizing young and aged ECs to young EC stiffness measurements.

Proliferation

To assess the proliferation status of young (3 month) and aged (24 month) endothelium in culture, fluorescent-labeled EdU incorporation was quantified by flow cytometry using Click-iT Plus EdU Flow Cytometry Assay Kit (ThermoFisher Scientific) according to the manufacturer's recommendations. In short, subconfluent ECs were incubated in serum-free StemSpan SFEM (StemCell Technologies, Inc.) overnight at 37° C. 5% $CO_2$ to synchronize the cell cycle in G0/G1. The following day, ECs were pulsed in 10 µM EdU (Alexa Fluor 488) in serum-containing growth media and analyzed at 6 and 24 hrs.

Senescence

To quantify senescent cells, subconfluent young (3 month) and aged (24 month) endothelial cultures were analyzed using the Fluorometric Quantitative Cellular Senescence Assay Kit (Cell BioLabs, Inc.) by flow cytometry, according to the manufacturer's suggestions.

Wound Healing

Cultured ECs from young (3 month) and aged (24 month) mice were plated at $10^4$ cells/well in a fibronectin-coated (Sigma-Aldrich) 96 well ImageLock tissue culture plate (Essen Bioscience) (n=8 replicate wells). At approximately 90% cell confluency, an approximately 700 µm homogenous scratch was generated using a 96 well WoundMaker (Essen Bioscience) according to the manufacturer's suggestions. Wells were subsequently washed two times using endothelial growth media to remove any dislodged cells. Wound healing was monitored for 48 hrs using IncuCyte ZOOM (Essen Bioscience) and calculated as a percent of original wound mask at 12 hr intervals. Relative wound density (RWD) was calculated using % $RWD_{(t)} = 100 * (w_{(t)} - w_{(0)})/(c_{(t)} - w_{(0)})$, in which $w_{(t)}$=Density of wound region at time (t) and $c_{(t)}$=Density of cell region at time (t).

Gene Expression

For gene expression analysis, total RNA from young (3 month) and aged (24 month) cultured endothelium was isolated using TRIzol Reagent (ThermoFisher Scientific) and cDNA was generated from 2 µg of total RNA using SuperScript III Reverse Transcriptase according to the manufacturer's suggested protocol. Reverse transcription quantitative PCR (RT-qPCR) analysis was performed using 40 ng cDNA template with 1 µM gene-specific primers and 1×SYBR Green Master Mix (Applied Biosystems) on a ViiA7 real-time PCR System (Applied Biosystems). Appropriate minus reverse transcriptase controls were included in all experiments. Primer sets were derived from Harvard Primer Bank or designed in-house (54-56). For a complete list of primers used, see Table 2, below.

TABLE 2

Primer sets used for young and aged endothelial gene expression analysis.

| Gene | Primer Bank ID | Fwd Primer (5'-3') | SEQ ID NO: | Rev Primer (5'-3') | SEQ ID NO: |
|---|---|---|---|---|---|
| Vcam1 | 26326181a1 | gttccagcgagggtctacc | 1 | aactcttggcaaacattaggtgt | 2 |

TABLE 2-continued

Primer sets used for young and aged endothelial gene expression analysis.

| Gene | Primer Bank ID | Fwd Primer (5'-3') | SEQ ID NO: | Rev Primer (5'-3') | SEQ ID NO: |
|---|---|---|---|---|---|
| Sele | 6755452a1 | atgcctcgcgct ttctctc | 3 | gtagtcccgctg acagtatgc | 4 |
| Kitl | 198596a1 | gaatctccgaag aggccagaa | 5 | gctgcaacaggg ggtaacat | 6 |
| Cxcl12 | 7305465a1 | tgcatcagtgac ggtaaacca | 7 | ttcttcagccgt gcaacaatc | 8 |
| Jag1 | 7305197a1 | cctcgggtcagt ttgagctg | 9 | cctt-gaggcaca ctttgaagta | 10 |
| Jag2 | 21553297a1 | caatgacac-cac tccagatgag | 11 | ggccaaa-gacgt cgttgcg | 12 |
| Dll1 | 164565442c2 | cccatcc-gattc cccttcg | 13 | ggttttctgtt gcgaggtcatc | 14 |
| Dll4 | 9506547a1 | ttccaggcaacc ttctccga | 15 | actgccgctat tcttgtccc | 16 |
| Igfbp3 | 6680385a1 | ccaggaaa-catc agtgagtcc | 17 | ggatggaactt ggaatcggtca | 18 |
| Csf1 | 166064045c1 | gtgtcagaacac tgtagccac | 19 | tcaaaggcaat ctggcatgaag | 20 |
| Il6 | 13624311a1 | tagtccttccta ccccaatttcc | 21 | ttggtccttag ccactccttc | 22 |
| Actb | In-house | cgtgcgtga-cat caaagagaa | 23 | ggccatctcct gctcgaa | 24 |

Ex Vivo Co-Culture

Primary murine young (3 month) or aged (24 month) hematopoietic stem and progenitor cells (HSPCs) were co-cultured on young or aged Akt-transduced endothelium in serum-free conditions with sKITL supplementation for fourteen days. To establish co-cultures, femurs and tibia from young and aged C57BL/6 (CD45.2$^+$) mice were isolated and whole bone marrow (WBM) was flushed using a 26.5-gauge needle with PBS (pH 7.2) containing 0.5% BSA (Fraction V) and 2 mM EDTA. Isolated WBM was subsequently depleted of hematopoietic lineage-committed cells using a murine hematopoietic Lineage Cell Depletion Kit (Miltenyi Biotec) according to the manufacturer's suggestions. Lineage-depleted HSPCs (10$^5$/well) were plated on a single well of a 12-well dish with confluent young or aged endothelium in 1 mL serum-free StemSpan SFEM (Stem-Cell Technologies, Inc.) with 50 ng/mL recombinant murine sKITL (PeproTech). Three independently-isolated HSPC populations were tested in parallel per EC line. Co-cultures were incubated at 37° C. and 5% CO$_2$ for a total of fourteen days as described: (Day 2) Co-cultures were supplemented 1 mL StemSpan SFEM and 50 ng/mL sKITL. (Day 4) Non-adherent hematopoietic cells were collected, pelleted (500×g 5 min), resuspended in 3 mLs StemSpan SFEM, and split 1:2 (1.5 mLs/well) into the original and adjacent 12-well with ECs (2×12-wells total). Co-cultures were supplemented with 50 ng/mL sKITL. (Day 6) Non-adherent hematopoietic cells were collected and split 1:2 into adjacent 12-wells with StemSpan SFEM to a final volume of 1.5 mLs (4×12-wells total). Co-cultures were supplemented with 50 ng/mL sKITL. (Day 7) Non-adherent hematopoietic cells were collected and depleted of lineage-committed cells using a murine hematopoietic Lineage Cell Depletion Kit. Lineage-depleted HSPCs (10$^5$/well) were plated on a single well of a new 12-well plate with confluent young or aged endothelium in 1 mL serum-free StemSpan SFEM with 50 ng/mL sKITL. StemSpan SFEM (1 mL/well) was added back to the original 12-well plate with 50 ng/mL sKITL. (Day 8-13) New 12-well plate was split as described above. StemSpan SFEM was exchanged every two days and re-plated with 50 ng/mL sKITL on the original 12-well co-culture plate. (Day 14) Endothelial and hematopoietic cells were collected using Accutase (Biolegend) for analysis. Cell numbers were determined using hemocytometer counts with Trypan Blue (Life Technologies) for live/dead exclusion. Total hematopoietic cell and HSPC frequency was assessed following co-culture using antibodies against CD45 (30-F11; Biolegend), GR1 (RB6-8C5; Biolegend), CD11B (M1/70; Biolegend), B220 (RA3-6B2; Biolegend), CD3 (17A2; Biolegend), CD41 (MWReg30; Biolegend), cKIT (2B8; Biolegend), and SCA1 (D7; Biolegend). To assess hematopoietic stem cell (HSC) repopulating activity, co-cultures were enriched for hematopoietic cells using murine CD45 Microbeads (Miltenyi Biotec); 5×10$^5$ CD45.2+(C57BL/6) co-cultured cells were transplanted into lethally-irradiated (950 Rads) young (3 months) CD45.1$^+$ (B6. SJL-Ptprc$^a$-

Pepc$^b$/BoyJ) recipients with 5×10$^5$ young (3 month) CD45.1$^+$ competitive WBM (per mouse) via retro-orbital sinus injection. Multi-lineage engraftment in peripheral blood was assayed four months post-transplant using antibodies raised against: GR1 (RB6-8C5; Biolegend), CD11B (M1/70; Biolegend), B220 (RA3-6B2; Biolegend), CD19 (1D3; BD Biosciences), CD4 (GK1.5; Biolegend), and CD8 at 1:100 (53-6.7; Biolegend). Antibodies used for hematopoietic engraftment: CD45.1 (A20; Biolegend), CD45.2 (104; Biolegend), TER119 (TER119; Biolegend).

Peripheral Blood Analysis

Peripheral blood was collected using 75 mm heparinized glass capillary tubes (Kimble-Chase) via retro-orbital sinus bleeds at indicated time points. To assess hematopoietic recovery following myeloablation, complete blood counts (CBC) were analyzed using an Advia120 (Bayer Healthcare). To quantify multi-lineage hematopoietic and HSC engraftment, peripheral blood was depleted of red blood cells (RBC lysis; Biolegend), stained with pre-conjugated antibodies and analyzed using flow cytometry as indicated.

Endothelial Cell Infusions

Young (3 month) or aged (24 month) C57BL/6 (CD45.2) mice were subjected to a myelosuppressive dose of total body γ-irradiation (TBI) (650 Rads) and infused with 5×10$^5$ young (3 month) or 5×10$^5$ aged (24 month) ECs via retro-orbital sinus injections on four successive days. PBS (vehicle) injections and steady state mice (non-irradiated) were used as controls. Peripheral blood CBCs were analyzed for hematopoietic recovery weekly for twenty-eight days following TBI. Pre-irradiated animals were bled to establish CBC baselines. To assess HSC activity, femurs were isolated twenty-eight days post-TBI and flushed using a 26.5-gauge needle with PBS (pH 7.2) containing 0.5% BSA (Fraction V) and 2 mM EDTA, counted using hemocytometers and Trypan Blue (Life Technologies) for live/dead exclusion, and 2×10$^6$ WBM cells were transplanted into lethally-irradiated (950 Rads) young (3 month) CD45.1$^+$ (B6. SJL-Ptprc$^a$Pepc$^b$/BoyJ) recipients with 10$^6$ young (3 month) CD45.1$^+$ competitive WBM (per mouse) via retro-orbital sinus injection. Multi-lineage engraftment in peripheral blood was assayed four months post-transplant using antibodies raised against GR1 (RB6-8C5; Biolegend), CD11B (M1/70; Biolegend), B220 (RA3-6B2; Biolegend), CD3 (17A2; Biolegend). Antibodies raised against CD45.1 (A20; Biolegend), CD45.2 (104; Biolegend), TER119 (TER119; Biolegend) were used for hematopoietic engraftment.

Endothelial-WBM Co-Infusions

Femurs and tibiae were harvested from young (3 month) or aged (24 month) C57BL/6 mice and flushed using a 26.5-gauge needle with PBS (pH 7.2) containing 0.5% BSA (Fraction V) and 2 mM EDTA, and counted using hemocytometers and Trypan Blue (Life Technologies) for live/dead exclusion. 10$^5$ WBM cells were transplanted into lethally-irradiated (950 Rads) young (3 month) C57BL/6 recipients with or without 5×10$^5$ young ECs via retro-orbital injection. PBS (vehicle) and steady state mice (non-irradiated) were used as controls. Hematopoietic recovery was monitored by peripheral blood CBCs at indicated time points. Mice were monitored daily to generate survival curves. To assess spleen colony-forming units (CFU-S), spleens were removed eight days post-TBI, fixed in Bouin's Solution (Sigma-Aldrich) overnight, and macroscopic surface colonies were quantified (48). Tissue histology was performed by Histoserv, Inc (Germantown, MD). In short, indicated tissues were fixed in 4% PFA in PBS (pH 7.2) overnight at 4° C., washed in PBS (pH 7.2), and subsequently dehydrated in 70% ethanol. Femurs were decalcified for 72 hrs in 10% EDTA in PBS (pH 7.2) at room temperature with gentle rocking prior to dehydration. Paraffin embedded femur, spleen, and small intestine tissues were sectioned (6 μm) and stained with Hematoxylin and Eosin (H&E) (Histoserv, Inc). Paraffin embedded femurs were processed for VEGFR3$^+$ sinusoidal vessel regression analysis using an antibody raised against VEGFR3 (AFL4; Biolegend) and counter-stained with Hematoxylin, as previously described (43). Images were taken on a BX51 (Olympus) light microscope at 10× or 20× magnification. To quantify bone marrow hematopoietic recovery, femurs were crushed using a mortar and pestle in PBS (pH 7.2) containing 0.5% BSA (Fraction V) and 2 mM EDTA and stained using antibodies raised against CD45 (30-F11; Biolegend), GR1 (RB6-8C5; Biolegend), CD115 (AFS98; Biolegend), and F4/80 (BM8; Biolegend).

Limiting Dilution

Femurs and tibiae were harvested from young (3 month) or aged (24 month) C57BL/6 mice and flushed using a 26.5-gauge needle with PBS (pH 7.2) containing 0.5% BSA (Fraction V) and 2 mM EDTA, and counted using hemocytometers and Trypan Blue (Life Technologies) for live/dead exclusion. For limiting dilution analysis, indicated numbers of WBM were transplanted into lethally-irradiated young (3 month) C57BL/6 recipients (950 Rads) in a non-competitive manner (per mouse) via retro-orbital injection (n=10 mice/cohort). Percent negative responding/dead mice were monitored throughout a four-month post-transplant period. Surviving mice were analyzed for multi-lineage engraftment in the peripheral blood, using antibodies raised against GR1 (RB6-8C5; Biolegend), CD11B (M1/70; Biolegend), B220 (RA3-6B2; Biolegend), CD3 (17A2; Biolegend). Long-term multi-lineage HSC frequency and 95% confidence intervals were determined using ELDA software (http://bioinf.wehi.edu.au/software/elda/) (57).

Hematopoietic Homing Analysis

Femurs and tibiae were harvested from young (3 month) or aged (24 month) C57BL/6 (CD45.2$^+$) mice and flushed using a 26.5-gauge needle with PBS (pH 7.2) containing 0.5% BSA (Fraction V) and 2 mM EDTA, and counted using hemocytometers and Trypan Blue (Life Technologies) for live/dead exclusion. For hematopoietic homing assessment, 10$^6$ young or aged WBM with or without 5×10$^5$ young (3 month) ECs were infused/co-infused into young (3 month) lethally-irradiated (950 Rads) CD45.1$^+$ (B6.SJL-Pqvc$^a$-Pepc$^b$/BoyJ) recipients. Femurs and spleens were removed 16 hours post-infusion, flushed with PBS (pH 7.2) containing 0.5% BSA (Fraction V) and 2 mM EDTA, and lysed for red blood cells (RBC lysis; Biolegend). Resulting cells were then stained for antibodies raised against CD45.1 (A20; Biolegend), CD45.2 (104; Biolegend), TER119 (TER119; Biolegend). CD45.2$^+$ hematopoietic cells were quantified by flow cytometry as a frequency per total WBM or splenocytes.

Statistics

No statistical models were employed to predetermine experimental sample sizes. Unless otherwise noted, all bar graphs and line graphs are displayed as mean±standard error of the mean (SEM) and significance was determine using unpaired two-tailed Student's t-tests with a threshold set at $P<0.05$. Median endothelial stiffness and significance (FIG. 2D) was determined using a non-parametric one-sided Wilcoxon Rank Sum test (alpha=0.001) to compare repeated force measurements. Data is presented as a box plot with whiskers representing ±1.5 interquartile range (IQR). Relative endothelial stiffness (FIG. 2E) is normalized to young ECs and presented as a 95% confidence interval. Survival curves (FIGS. 5, A and B) were calculated using the Log- Rank test to compare WBM to WBM+EC cohorts. Long-term multi-lineage HSC frequency and 95% confidence intervals (FIGS. 5, G and H) were determined using ELDA software (http://bioinfwehi.edu.au/software/elda/) (57).

Example 2. Characterization of the Aged Bone Marrow Microvasculature

To examine potential aging-related alterations in BM endothelium, the vasculature of young (3 month) and aged (24 month) C57B/6 mice was intra-vitally labeled with an EC-specific antibody raised against VECAD to assess endothelial morphology in the BM microenvironment. Aged mice display distinct changes in vascular morphology, appearing dilated and more discontinuous and suggesting a potential change in vascular integrity (FIG. 1A). We next examined vascular permeability using intravenous injection of Evans Blue Dye. Femurs from aged mice demonstrated a significant increase in vascular leakiness, as measured by dye extraversion (FIG. 1B and FIG. 1C). The frequency of $VECAD^+CD31^+CD45^-TER119^-$ BM ECs was also significantly reduced, with a marked increase in $VECAD^-CD31^-CD45^-TER119^-$ pan-BM stromal cells (FIG. 1D and FIG. 1E). BM ECs from aged mice also displayed metabolic dysregulation, including a significant increase in reactive oxygen species (ROS) (FIG. 1F) and hypoxic status (FIG. 1G and FIG. 1H). These observations are consistent with aging-related vascular dysfunction (31-36), and suggest that instructive endothelial niche function might also be compromised during aging.

Example 3. Cultured ECs from Aged Mice Display Aging-Related Functional Alterations To examine changes in the hematopoiesis-instructive function of aged endothelium, BM-derived ECs were isolated from young (3 month) and aged (24 month) C57BL/6 mice, as previously described (37). Cultured ECs displayed uniform cell-surface expression of VECAD by immunofluorescence (FIG. 2A) and expressed pan-endothelial markers ($VECAD^+$ and $CD31^+$) by Flow Cytometry (FIG. 2B). Next, aging-related characteristics in young and aged BM ECs were examined. While young and aged ECs did not have any differences in overall cell dimensions, aged ECs displayed an increase in median cellular stiffness, as measured by atomic force microscopy (AFM) (FIG. 2B-FIG. 2D). An increase in vascular stiffness in vivo has been reported to be associated with an aging-related senescence and a decrease in endothelial angiogenic potential (38-40). However, aged EC cultures displayed no overt senescence-related morphology or significant changes in senescence-associated β-galactosidase (SA β-Gal) activity (FIG. 2A and FIG. 2H). Aged ECs demonstrated a delay in cell cycle progression at 6 hours post cell-cycle synchronization, that was resolved by 24 hours (FIG. 2F and FIG. 2G). The angiogenic potential of aged ECs in an in vitro wound healing assay was examined next. Aged ECs displayed a significant delay in wound healing, suggesting an age-related impairment in cell migration (FIG. 2I and FIG. 2J). Taken together, cultured BM-derived ECs isolated from aged mice demonstrate functional alterations in vitro that are consistent with aging-related phenotype cells.

The BM vascular niche supports young HSC homeostasis in vivo through the expression of pro-hematopoietic factors such as Kitl, Cxcl12, and Jag1. Genetic deletion of these factors using EC-specific Tie2-cre and Cdh5-cre results in loss of HSC frequency and repopulating activity (19, 20, 22, 23). Secreted and cellular levels of KITL was reported to be significantly decreased within BM of aged mice (27). In humans, plasma levels of SDF1 (CXCL12) are also diminished with aging, positively correlating with a phenotypic expansion of BM HSCs and inversely correlating with BM fat accumulation, two hallmarks of BM aging (41). To determine whether aged ECs display an aberrant expression of these critical pro-HSC factors, we performed gene expression analysis by reverse transcriptase-quantitative PCR (RT-qPCR) on cultured aged ECs which demonstrated a decrease in Kitl, Cxcl12, and NOTCH ligand expression (FIG. 2K), suggesting an impaired instructive function in aged ECs.

Figure 8A:
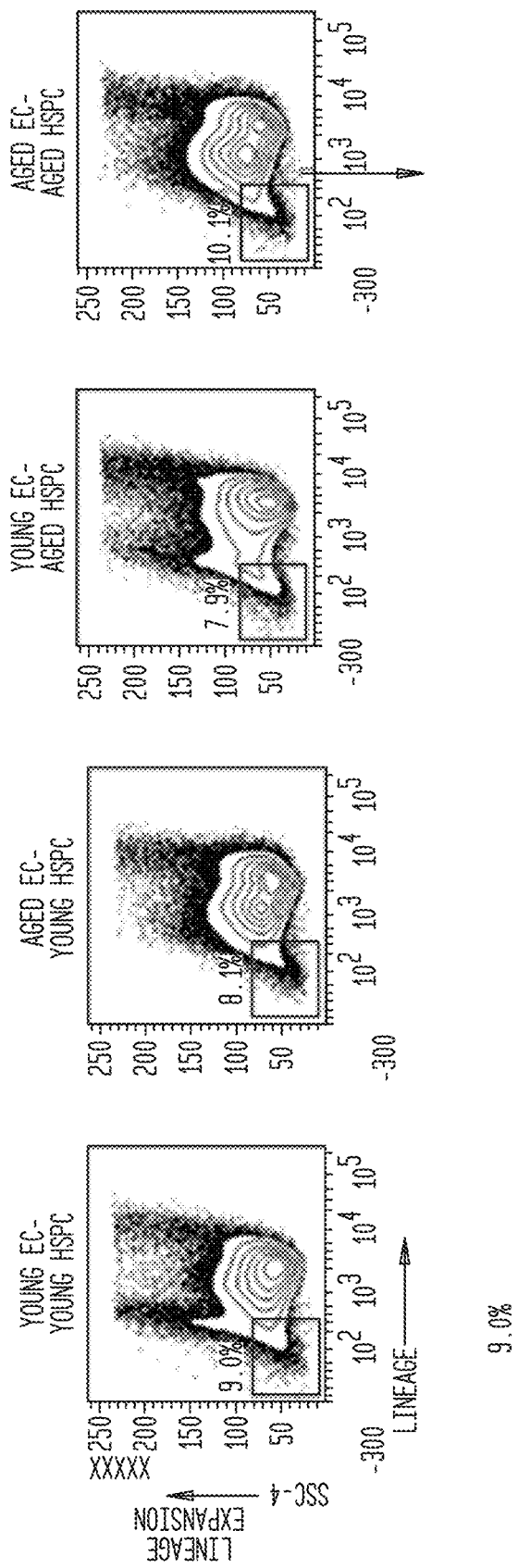
Figure 8B:
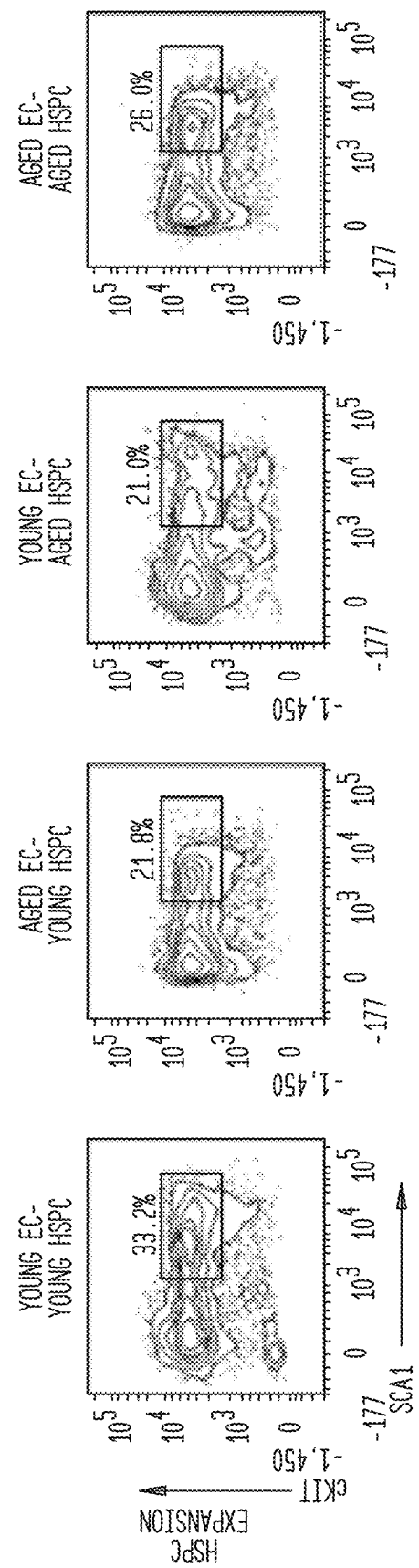
Figure 8E:
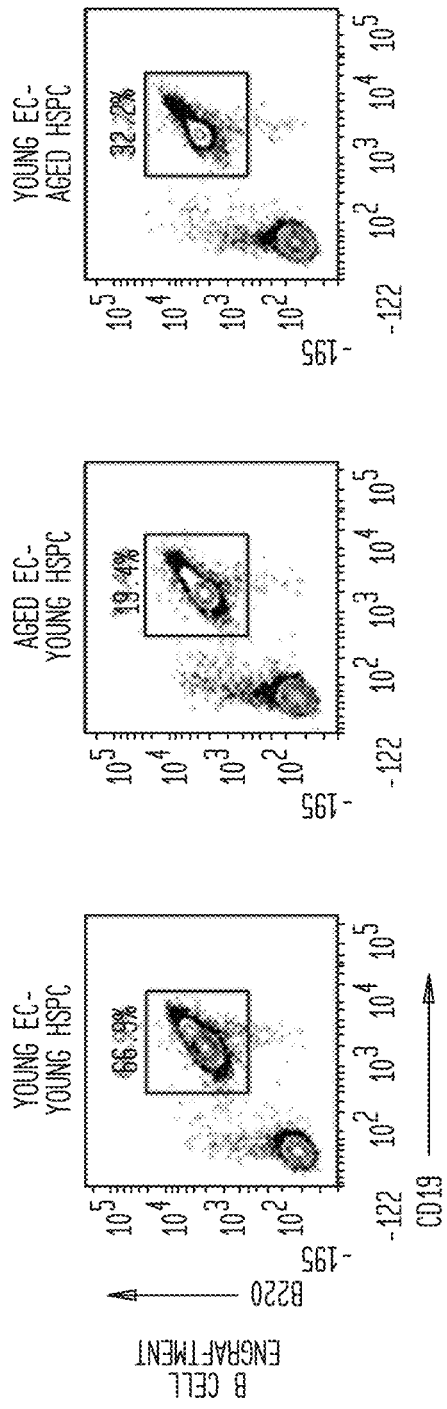

Example 4. Aged ECs Promote Hematopoietic Aging Phenotypes on Co-Cultured Young HSPCs Aging of the hematopoietic system is, in part, functionally defined by a decrease in HSC repopulating activity and an increase in the frequency of myeloid cell output at the expense of lymphoid cells (8, 42). To examine the possibility that aged ECs play a direct role in promoting aging-related hematopoietic phenotype cells, the recently described ex vivo hematopoietic stem and progenitor cell (HSPC)/EC co-culture system was employed (37). This model has been used to faithfully recapitulate in vivo endothelial NOTCH and NF-κB mediated regulation of HSCs in the vascular niche (23, 43). By culturing isolated HSPCs directly on ECs in serum-free conditions, it is possible to segregate and examine the instructive role played by aged ECs in maintaining HSPC homeostasis. To this end, $CD45.2^+$ whole BM (WBM) was isolated from young (3 month) and aged (24 month) mice and depleted of lineage-committed hematopoietic cells; resulting young and aged HSPCs ($10^5$ lineage$^-$ cells) were plated on young (3 month) and aged (24 month) ECs for 14 days in serum-free media with supplementation of 50 ng/mL soluble KITL (sKITL). To examine hematopoietic expansion following ex vivo co-culture, phenotypic $CD45.2^+$ hematopoietic cells and $CD45.2^+lineage^-cKIT^+SCA1^+$ HSPCs were quantified. Aged ECs promoted an increase in total $CD45.2^+$ hematopoietic cell expansion in both young and aged HSPC co-cultures when compared with their young EC counterparts (FIG. 3A). Within this population, aged ECs promoted a significant increase in phenotypic aged HSPC expansion, while young HSPCs displayed no observable differences when compared with young EC feeders (FIG. 3B and FIGS. 8A and 8B). To examine the long-term repopulating capacity of young and aged HSPCs cultured on young and aged ECs following nine days of ex vivo expansion, total co-cultured cells were collected and $CD45.2^+$ hematopoietic cells were purified from EC feeders and competitively transplanted in a 1:1 ratio with young (3 month) $CD45.1^+$ WBM cells into lethally irradiated young (3 month) CD45.1 recipient mice. Mice were assessed for long-term multi-lineage engraftment four months post-transplantation. To control for young and aged hematopoietic phenotype cells, pre-expansion WBM input was competitively transplanted in a 1:1 ratio and analyzed at four months to confirm hematopoietic engraftment deficiencies and myeloid biased output associated with aging (FIG. 3C-FIG. 3F). Young HSPCs co-cultured on aged ECs demonstrated a significant decrease in engraftment when compared with young HSPCs co-cultured on young ECs (FIG. 3C and FIG. 8C). Moreover, aged HSPCs co-cultured on aged ECs were unable to competitively engraft lethally-irradiated animals, while aged HSPCs co-cultured on young ECs were partially rejuvenated and displayed robust hematopoietic engraftment (FIG. 3C and FIG. 8C).

Taken together, this data suggests that aged ECs are significantly impaired in their HSC-instructive function. Despite the observed increase in engraftment of aged HSPCs co-cultured on young ECs, aged HSCs maintained a bias in $CD11B^+GR1^+$ myeloid cell production at the expense of $B220^+CD19^+$ B cells and $CD8^+/CD4^+$ T cells when compared to young HSPC-young EC co-cultured controls (FIG. 3D-FIG. 3F and FIG. 8D-8F). Conversely, young HSPCs co-cultured on aged ECs acquired a myeloid bias with a decrease in B cell and T cell frequency (FIG. 3D-FIG. 3F and FIG. 8D-8F). This data, along with the observed decline in engraftment of young HSPCs co-cultured on aged ECs, suggests that aged vascular endothelium, independent of other stromal constituents, is sufficient to impart hematopoietic aging phenotypes on young HSCs. Moreover, these data also allow for the possibility that EC-specific intervention may provide a therapeutic opportunity to increase HSC function in aged populations following hematopoietic injury.

Example 5. Infusion of Aged ECs Promotes a Myeloid Bias In Vivo

Figure 4B:
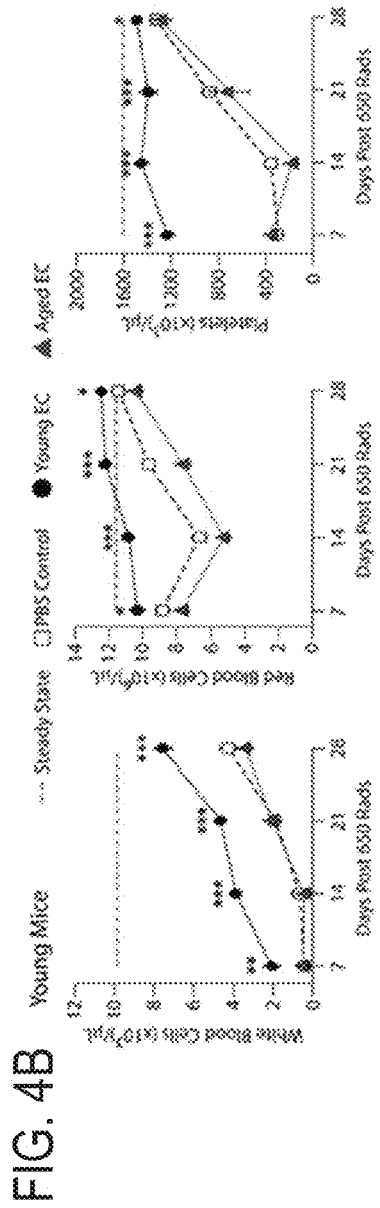
Figure 4C:
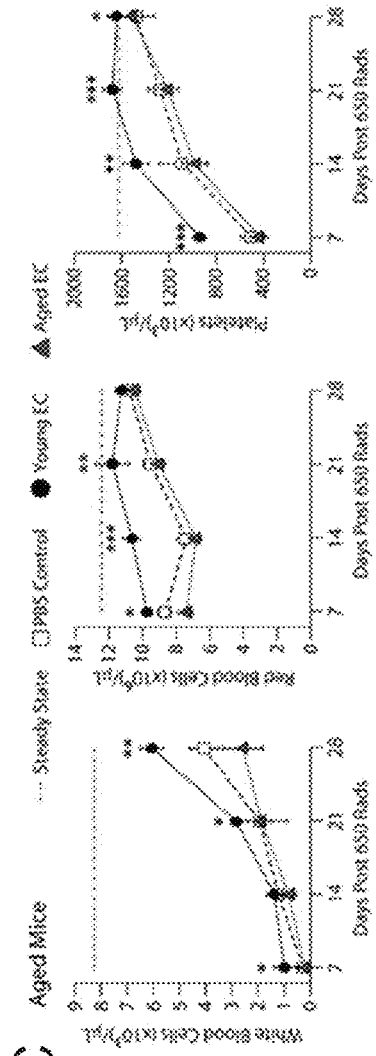
Figure 4D:
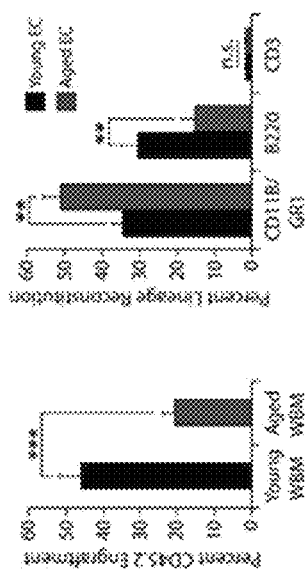
Figure 4E:
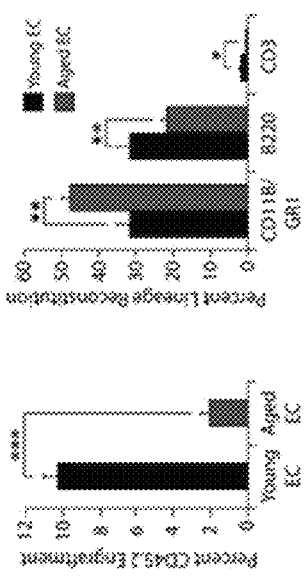
Figure 12:
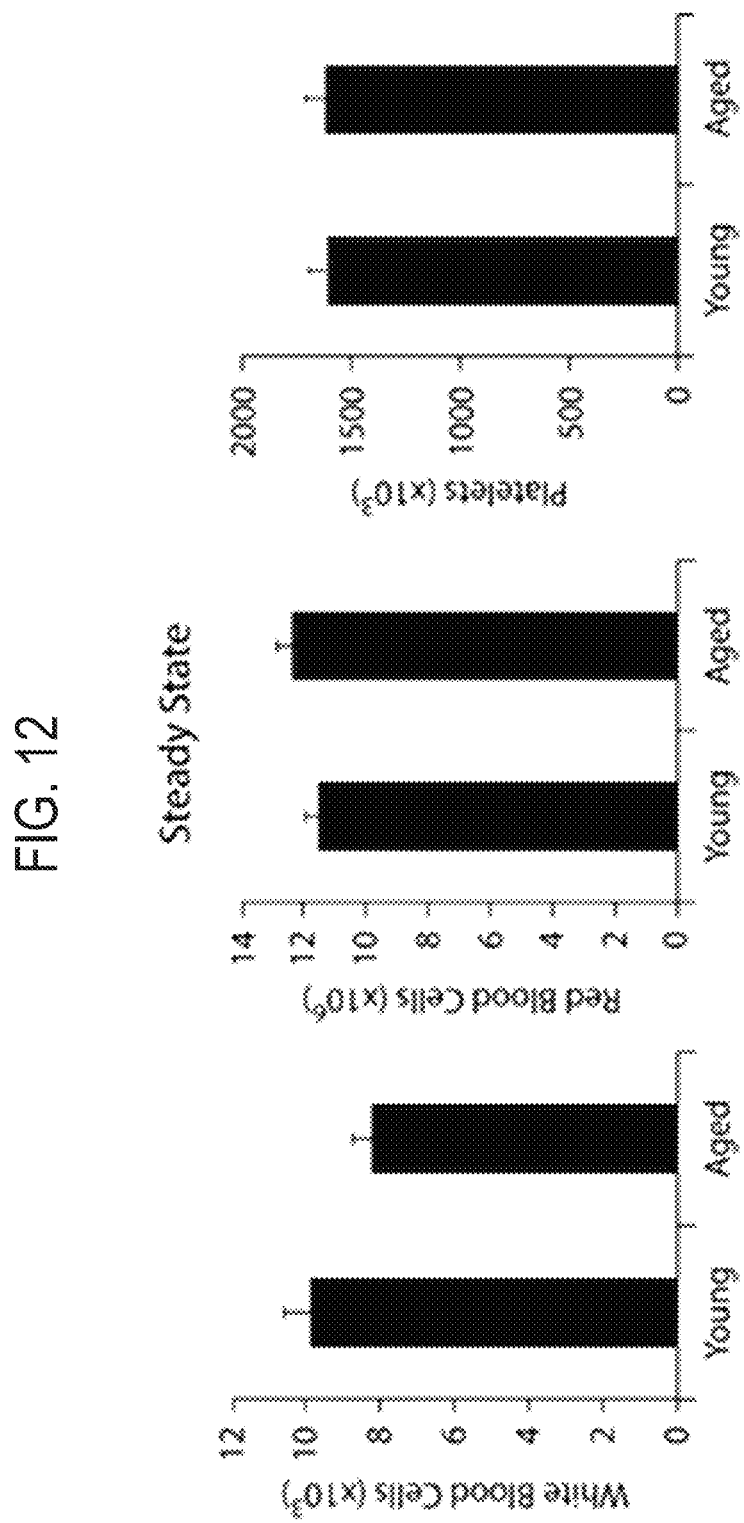
FIG. 12 shows complete blood counts of young and aged control mice. Steady state (pre-irradiation) young (3 month) and aged (24 month) C57BL/6 mice were bled and analyzed for peripheral blood counts (n=5). Results demonstrate no observable differences between pre-irradiation young or aged animals. Unpaired two-tailed Student's t-tests were performed to determine significance (* P<0.05;  P<0.01; * P<0.001).

Endothelial cells generated from a number of hematopoietic and non-hematopoietic tissues have been used to demonstrate their therapeutic potential following irradiative hematopoietic insult (37, 44-46). It was previously shown that young niche-specific BM-derived ECs infused into young recipients following radiation- and chemotherapy-mediated myeloablative injury promotes rapid and efficient regeneration of the hematopoietic system by reducing the duration of pancytopenias and safeguarding HSC function (37, 43). In ex vivo co-culture experiments, aged ECs were unable to support young HSC repopulating activity and imparted a myeloid bias at the expense of B and T cell output in long-term engraftment mice (FIG. 3C-FIG. 3F). To further examine the aging-related impaired instructive function of aged ECs in an in vivo context, $5 \times 10^5$ aged ECs were infused into young C57BL/6 mice on four successive days following myelosuppressive total body irradiation (TBI) and assessed peripheral hematopoietic recovery weekly (FIG. 4A). Young ECs were used as a positive control. It is important to note that in these experiments, EC infusions are done in the absence of exogenous HSCT and address only endogenous hematopoietic recovery in young mice following myelosuppressive injury. Infusion of young ECs into young mice following myelosuppressive insult promotes rapid recovery of the hematopoietic system (RBCs, WBCs and platelet counts), while infusion of aged ECs were unable to support efficient hematopoietic recovery in young recipients (FIG. 4B), suggesting that aged ECs have an impaired hematopoietic-instructive function in vivo. After allowing 28 days for recovery, the HSC-protective potential of EC infusions was examined in these mice. WBM isolated from EC-infused young cohorts ($CD45.2^+$ donor) was transplanted with a competitive dose of freshly isolated young $CD45.1^+$ WBM in a 2:1 ratio into lethally-irradiated young CD45.1 recipients (FIG. 4A). Competitive transplantation of WBM ($CD45.2^+$) isolated from steady state young and aged mice (non-irradiated and without EC infusion) was performed to serve as baseline controls for comparing aging induced hematopoietic phenotype cells (FIG. 4D and FIG. 12). Long-term, multi-lineage engraftment was analyzed four months post-transplantation. In agreement with ex vivo HSPC expansions (FIG. 3C), aged ECs infusions were unable to support endogenous HSC activity in young mice, (FIG. 4E). Interestingly, aged EC infusions also promoted a significant $CD11B^+/GR1^+$ myeloid biased output at the expense of $B220^+$ B cell and $CD3^+$ T cell engraftment when compared with young EC-infused animals (FIG. 4E). Collectively, this data demonstrates that infusion of aged ECs into young recipients following myelosuppressive injury impairs their endogenous HSC activity and imparts a myeloid bias, further supporting the idea that an aged vascular niche can impart aged hematopoietic phenotypes on a young hematopoietic system.

Example 6. Young ECs Enhance Endogenous HSC Activity of Aged Mice

Figure 4F:
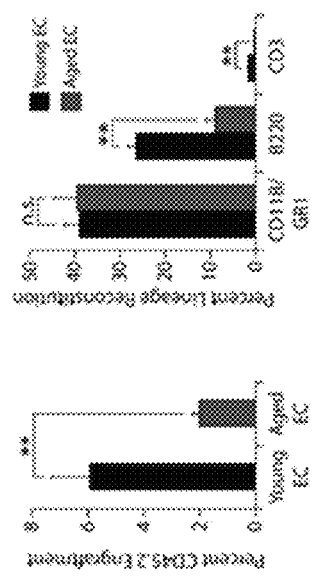

Given that the elderly population responds poorly to intensive myelosupressive therapy often required to treat hematopoietic malignancies (47), it was next tested if infusion of young ECs into aged recipients could provide therapeutic potential by diminishing the duration of cytopenias following myelosuppressive irradiation. As observed in young cohorts, aged mice receiving young EC infusions following myelosuppressive TBI demonstrated increased recovery of WBCs, RBCs, and platelet cell counts in the peripheral blood (PB), while aged EC infusions failed to promote improvement (FIG. 4C). HSC-rejuvenating potential of young EC infusions in aged mice following TBI-mediated myelosuppression was examined. As previously described, WBM isolated from EC-infused aged cohorts ($CD45.2^+$ donor) was transplanted 28 days post-irradiation with a competitive dose of young $CD45.1^+$ WBM in a 2:1 ratio into lethally-irradiated young CD45.1 recipients (FIG. 4A). Long-term, multi-lineage engraftment was analyzed four months post-transplantation. As previously observed in aged HSPCs-young EC co-cultures (FIG. 3C), aged mice that received young ECs also demonstrated a marked improvement in overall hematopoietic engraftment (FIG. 4F). Moreover, while young EC infusions could not resolve the myeloid biased output of aged HSCs, young ECs were able to significantly increase the output of the B and T cell lineages in recipients (FIG. 4F). Taken together, these data suggest that not only can young ECs be used to rejuvenate the functional output of endogenous aged hematopoietic cells in vivo, but they also could potentially be utilized to enhance the exogenous hematopoietic engraftment following myeloablative pre-conditioning and BM transplantation.

Example 7. Young EC Co-Infusion Enhances HSCT and Promotes Overall Survival

Figure 9A:
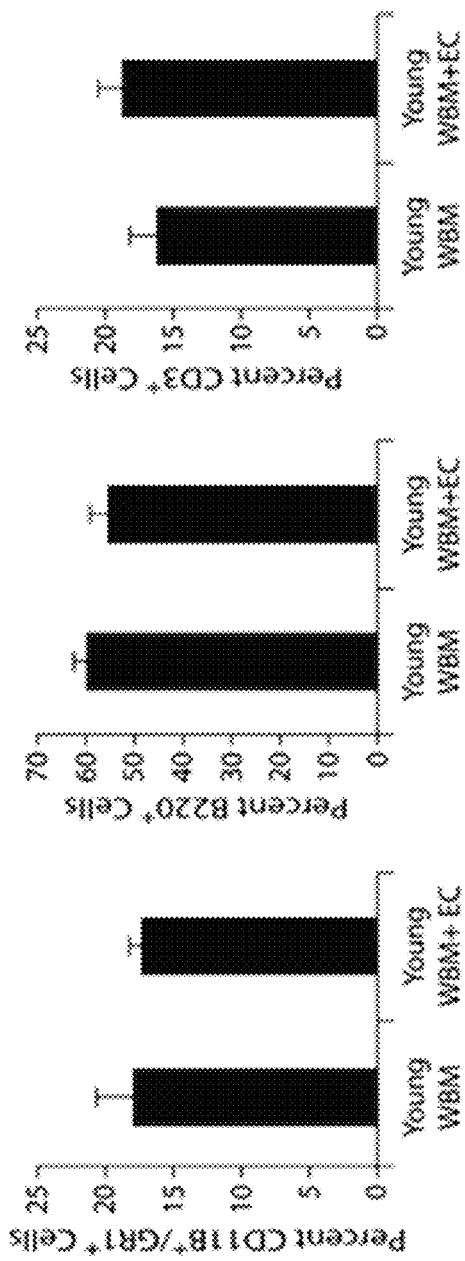
FIGS. 9A and 9B show multi-lineage reconstitution of WBM-EC co-infused animals.
Figure 9B:
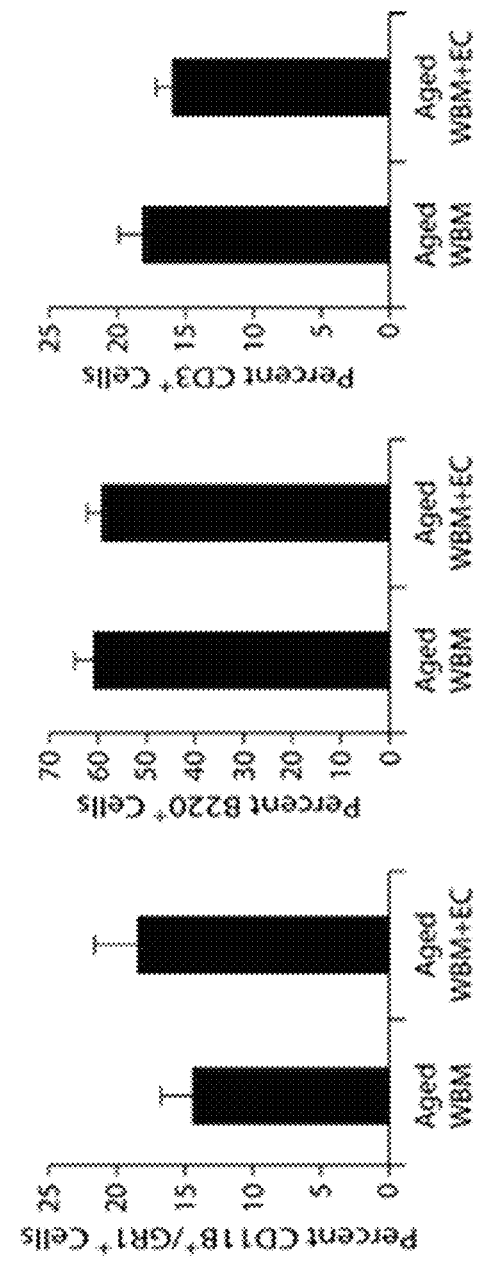
Figure 10D:
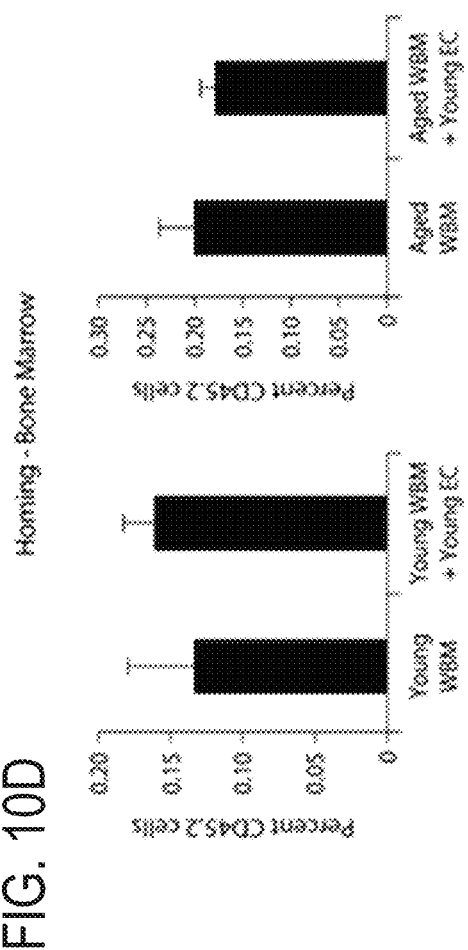
Figure 10E:
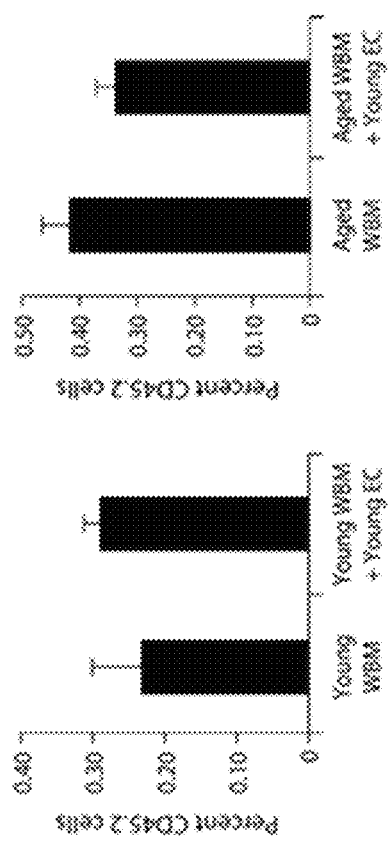

Allogeneic transplantation of adult BM can provide a cure for patients with life-threatening hematological disorders. However, there is a large group of patients who do not have access to HLA-matched BM. Strategies to expand the number of patients that can utilize a single BM harvest by minimizing the number of BM cells necessary for rapid hematopoietic recovery and long-term, multi-lineage engraftment would be useful. Additionally, there are hematopoietic disorders, such as sickle cell disease, that could benefit from autologous transplantation of the patient's own gene corrected BM. However, many cases result in a sub-optimal number of BM cells that are necessary to achieve robust engraftment. To this end, it was next examined if a single dose co-infusion of young ECs in the context of a limiting HSCT cell dose could enhance hematopoietic engraftment and promote survival. To this end, $10^5$ young or aged WBM cells were transplanted into young recipients with or without a single co-infusion of $5 \times 10^5$ young ECs following a lethal-dose of TBI (950 Rads). Of note, transplantation of $2 \times 10^5$ young WBM cells alone in recipient mice results in complete radioprotection following lethal-irradiation, while a $10^5$ WBM cell dose is suboptimal. Steady state (non-irradiated and without WBM or EC infusion), young ECs alone or PBS vehicle infusions were used to establish baselines. Survival curves revealed that a single dose of $5 \times 10^5$ young ECs alone were unable to radio-protect mice following myeloablative injury (FIG. 5A). Mice that received $10^5$ WBM from either young or aged donors resulted in 70% and 50% survival, respectively (FIG. 5A and FIG. 5B). However, mice that were co-infused with $10^5$ young WBM and $5 \times 10^5$ young ECs resulted in complete survival (FIG. 5A). Moreover, animals co-infused with $10^5$ aged WBM and $5 \times 10^5$ young ECs achieved 90% survival rates (FIG. 5B). These data demonstrate that co-infusion of young ECs with limiting numbers of WBM from both young and aged donors results in increased survival following myeloablation, with all mice achieving long-term, multi-lineage engraftment (FIGS. 9A and 9B). Furthermore, co-infusing young ECs with young WBM into lethally-irradiated mice also improved short-term and long-term hematopoietic recovery when compared to the young WBM alone cohort (FIG. 5C), while young ECs co-infused with aged WBM resulted in minimal increase in recovery of RBCs and platelets, as compared to aged WBM alone (FIG. 5D). It was next examined if young ECs conferred a radio-protective effect on co-infused HSPC activity by assessing Spleen Colony-Forming Units (CFU-S) (48). It was found that the co-infusion of young ECs with either young or aged whole BM resulted in an increase in the number of hematopoietic colonies that formed in the spleen following transplantation (FIG. 5E and FIG. 5F and FIG. 10A). This observation supports the previous data (FIG. 4E and FIG. 4F), that suggests that young EC infusions following myelosuppressive TBI protected endogenous HSC activity. Therefore, the possibility that young EC co-infusion with WBM could increase HSC repopulating activity was examined. Limiting dilution analysis (LDA) was performed by transplanting $2 \times 10^5$, $10^5$, and $5 \times 10^4$ WBM isolated from steady state young or aged mice with or without a co-infusion of $5 \times 10^5$ young ECs into lethally-irradiated recipients. Survival was monitored for 6 months and used to quantify the non-responding fraction. Young and aged WBM co-infused with young ECs demonstrated a significant ~2-fold (young WBM; P=0.0225) and ~3-fold (aged WBM; P=0.0035) increase in hematopoietic repopulating activity when compared to WBM alone (FIG. 5G and FIG. 5H and FIGS. 10B and 10C). The increase in hematopoietic reconstitution was independent of homing defects (FIGS. 10D and 10E). These data demonstrate that co-infusion of young ECs promotes overall survival of myeloablated recipients and enhances HSCT activity.

Example 8. Young EC Co-Infusion Radioprotects the BM Sinusoidal Vascular Niche

Figure 7A:
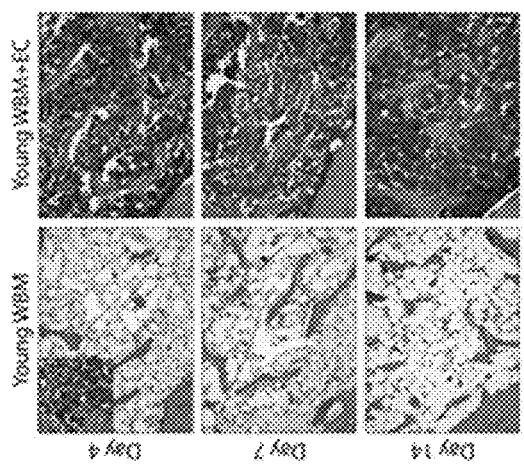
Figure 7B:
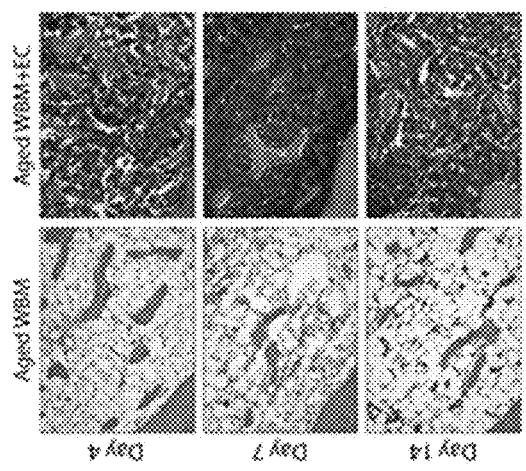
Figure 11B:
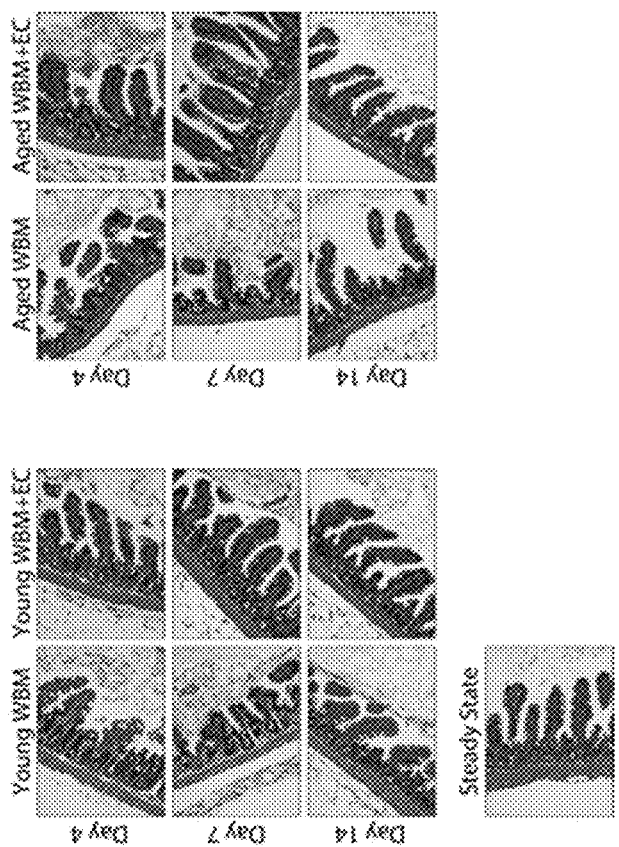
FIG. 11A and FIG. 11B shows Endothelial cell co-infusion safeguards radiosensitive tissues. Following a lethal dose of total body irradiation (950 Rads), C57BL/6 mice infused with a single dose of young (3 month) or aged (24 month) whole bone marrow with or without 5×10$^5$ young endothelial cells (ECs) and assessed for tissue damage. Representative Hematoxylin and Eosin (H&E) stained sections demonstrate distinct radioprotection of both (FIG. 11A) spleen and (FIG. 11B) intestine tissue morphology in EC co-infused groups (n=10 mice/cohort; 100× and 200× magnification, respectively).
Figure 11A:
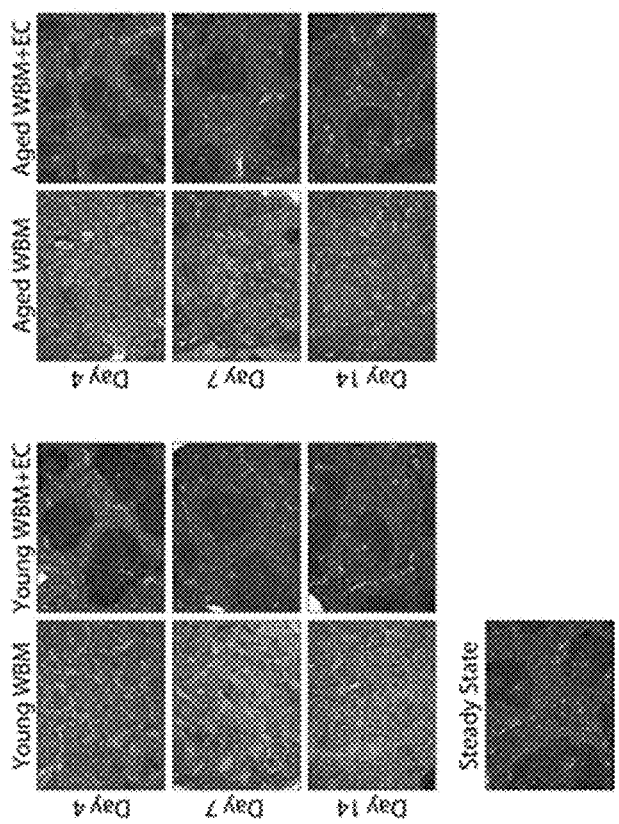

Sinusoidal endothelium within the BM microenvironment undergo significant damage in response to irradiation (49). Regeneration of BM sinusoidal ECs is also required for hematopoietic engraftment and regeneration following radiation-induced injury (50). The observed increase in HSC engraftment in co-infused cohorts suggests that infused ECs may protect the BM vascular microenvironment. Therefore, BM recovery in EC co-infused cohorts following myeloablative irradiation was examined. Young EC co-infusions in young and aged WBM groups displayed a significant increase in BM cellularity and CD45$^+$ hematopoietic cell frequency seven days post-irradiation (FIG. 6A, FIG. 6C and FIG. 6D). Using a VEGFR3 antibody to distinguish BM sinusoidal endothelium, the extent of vascular damage in co-infused mice was assessed. Young ECs mitigated BM sinusoidal endothelial damage, displaying a significant decrease in Type I and Type II endothelial damage (FIG. 6B, FIG. 6E, FIG. 6F). Radioprotection of BM cellularity extended to early (Day 4) and later (Day 14) time points (FIG. 7A and FIG. 7B). Moreover, WBM transplanted mice co-infused with young ECs demonstrated radioprotection of BM myeloid cells (FIG. 7C-FIG. 7F). Interestingly, a single dose of co-infused young ECs extended their regenerative effects to other radiosensitive tissues, including the spleen and intestine (FIG. 11), further expanding the therapeutic potential of young endothelial infusions to mitigate damage caused by radiation-mediated injury.

The Examples described herein demonstrate that physiological aging of ECs is sufficient to promote functional aging of young HSCs in ex vivo co-culture experiments (FIG. 3C-FIG. 3F). These ex vivo results were confirmed in an in vivo model system in which aged ECs infused into young mice following myelosuppressive irradiation imparted a myeloid bias at the expense of B and T cell output, while inhibiting HSC engraftment (FIG. 4E). These observations were independent of aging-related changes to other microenvironmental cellular constituents, suggesting that aged endothelium are sufficient to drive aging-related hematopoietic defects. While the decrease in expression of expression of verified pro-HSC factors. Kitl, Cxcl12, and NOTCH ligands in aged ECs likely contribute to their impaired HSC supportive function (FIG. 2K), there are likely a number of additional pathways and factors that contribute to the observed EC-mediated aging phenotype cells acquired in young HSCs. The Examples described herein demonstrate that aged endothelium can directly initiate age-related hematopoietic phenotype cells, allowing for potential therapeutic intervention in aged vascular niches.

Figure 7E:
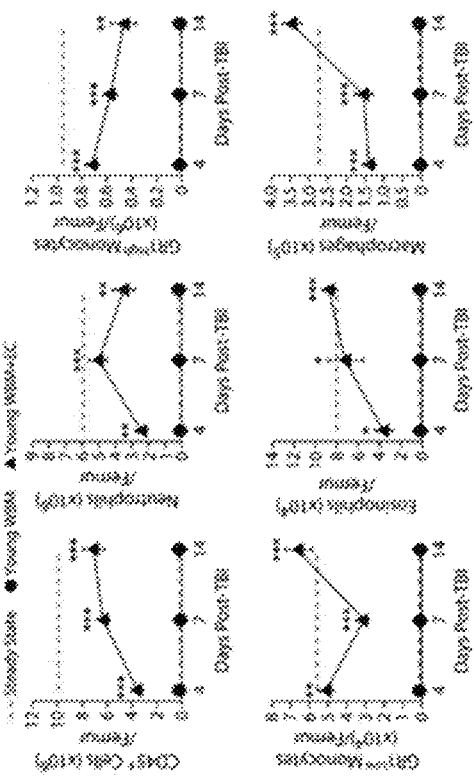
Figure 7F:
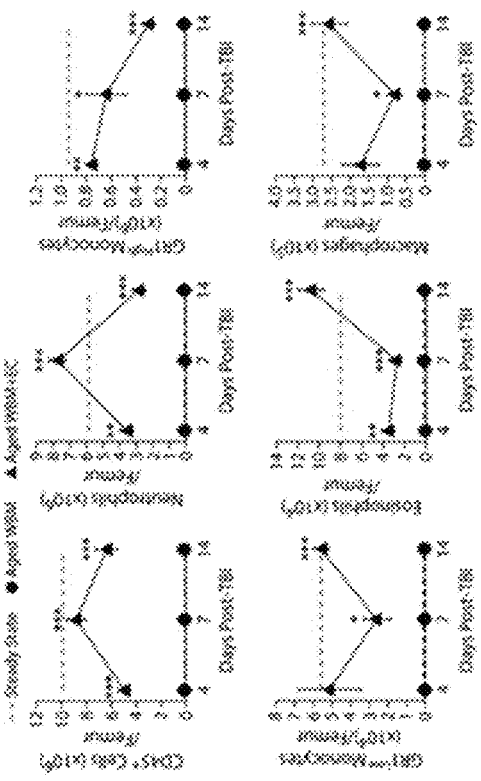

The utility of ECs in enhancing hematopoietic recovery and safeguarding HSPCs following irradiation was previously demonstrated (37, 43-46, 52). In these experiments, repeated intravenous EC doses or implanted donor vasculature provides a significant hematopoietic radioprotective effect in young mice. However, it is not clear if this protective effect extends to an aged hematopoietic system (11, 15). Co-culture of aged HSPCs on young ECs could partially rejuvenate HSC activity, but failed to reverse the aging-related intrinsic myeloid bias (FIG. 3C-FIG. 3F). While infusion of young ECs into aged mice following sublethal myelosuppressive irradiation was also able to significantly enhance peripheral hematopoietic recovery and endogenous aged HSC activity (FIG. 0.4C and FIG. 4FF), it was unable to revert the observed myeloid bias. Young EC infusions were able to enhance B cell and T cell output in aged mice (FIG. 4F), further demonstrating their therapeutic potential. Following a lethal dose of ionizing TBI, a single co-infusion of young ECs was able to significantly increase survival, hematopoietic progenitor activity and HSC engraftment in mice transplanted with aged WBM (FIG. 5B and FIG. 5E-FIG. 5H). Hematopoietic engraftment and reconstitution is dependent on the successful regeneration of BM sinusoidal endothelium following irradiation (50). EC co-infusion significantly diminished VEGFR3$^+$ sinusoidal EC damage by decreasing the prevalence of Type I and Type II regressed and hemorrhagic vessels within the BM (FIG. 6B and FIG. 6 E-FIG. 6F), preserved BM cellularity (FIG. 6A, and FIG. 6C-FIG. -D and FIG. 7A and FIG. 7B), and enhanced BM granulocyte-macrophages populations (FIG. 7E and FIG. 7F). These results demonstrate that young ECs can act as a supportive cellular therapy, protecting the aged BM microenvironment following radiation-mediated injury and promoting the rejuvenation of an aged hematopoietic system.

Altogether, the Examples herein demonstrate that a young BM vascular niche plays a critical role in supporting homeostatic hematopoiesis and HSC activity and that physiological aging disrupts endothelial instructive function. This suggests the by providing young endothelium via infusions, current therapies that rely on curative myeloablative strategies to enhance hematopoietic outcomes can be augmented, including overall HSC engraftment efficiency, restoration of B cell and T cell frequency, and overall survival. This study further provides ex vivo and in vivo tools to dissect the molecular changes in aged ECs that play a role in modulating HSC activity during physiological aging, allowing the elucidation of the mechanisms by which the dysregulation of the homeostatic BM vascular microenvironment leads to many common age-related hematopoietic disorders.

REFERENCES

1. Federal Interagency Forum On Aging Related Statistics. Older Americans 2016: Key Indicators of Well-Being. https://agingstats.gov/.
2. Schlitzkus L L, Melin A A, Johanning J M, and Schenarts P J. Perioperative management of elderly patients. Surg Clin North Am. 2015; 95(2):391-415.
3. North B J, and Sinclair D A. The intersection between aging and cardiovascular disease. Circ Res. 2012; 110(8): 1097-108.
4. Berger N A, Savvides P, Koroukian S M, Kahana E F, Deimling G T, Rose J H, Bowman K F, and Miller R H. Cancer in the elderly. Trans Am Clin Climatol Assoc. 2006; 117(147-55; discussion 55-6.
5. Dorshkind K, and Swain S. Age-associated declines in immune system development and function: causes, consequences, and reversal. Curr Opin Immunol. 2009; 21(4):404-7.
6. Eisenstaedt R, Penninx B W, and Woodman R C. Anemia in the elderly: current understanding and emerging concepts. Blood Rev. 2006; 20(4):213-26.
7. Lichtman M A, and Rowe J M. The relationship of patient age to the pathobiology of the clonal myeloid diseases. Semin Oncol. 2004; 31(2):185-97.
8. Pang W W, Schrier S L, and Weissman I L. Age-associated changes in human hematopoietic stem cells. Semin Hematol. 2017; 54(1):39-42.
9. Cho R H, Sieburg H B, and Muller-Sieburg C E. A new mechanism for the aging of hematopoietic stem cells: aging changes the clonal composition of the stem cell compartment but not individual stem cells. Blood. 2008; 111(12):5553-61.
10. Dykstra B, and de Haan G. Hematopoietic stem cell aging and self-renewal. Cell Tissue Res. 2008; 331(1): 91-101.
11. Rossi D J, Bryder D, Zahn J M, Ahlenius H, Sonu R, Wagers A J, and Weissman I L. Cell intrinsic alterations underlie hematopoietic stem cell aging. Proceedings of the National Academy of Sciences of the United States of America. 2005; 102(26):9194-9.
12. Van Zant G, and Liang Y. The role of stem cells in aging. Experimental hematology. 2003; 31(8):659-72.
13. Pang W W, Price E A, Sahoo D, Beerman I, Maloney W J, Rossi D J, Schrier S L, and Weissman I L. Human bone marrow hematopoietic stem cells are increased in frequency and myeloid-biased with age. Proceedings of the National Academy of Sciences of the United States of America. 2011; 108(50):20012-7.
14. Chambers S M, Shaw C A, Gatza C, Fisk C J, Donehower L A, and Goodell M A. Aging hematopoietic stem cells decline in function and exhibit epigenetic dysregulation. PLoS Biol. 2007; 5(8):e201.
15. Geiger H, de Haan G, and Florian M C. The ageing haematopoietic stem cell compartment. Nat Rev Immunol. 2013; 13(5):376-89.
16. Elias H K, Bryder D, and Park C Y. Molecular mechanisms underlying lineage bias in aging hematopoiesis. Semin Hematol. 2017; 54(1):4-11.
17. Akunuru S, and Geiger H. Aging, Clonality, and Rejuvenation of Hematopoietic Stem Cells. Trends Mol Med. 2016; 22(8):701-12.
18. Morrison S J, and Scadden D T. The bone marrow niche for haematopoietic stem cells. Nature. 2014; 505(7483): 327-34.
19. Ding L, Saunders T L, Enikolopov G, and Morrison S J. Endothelial and perivascular cells maintain haematopoietic stem cells. Nature. 2012; 481(7382):457-62.
20. Ding L, and Morrison S J. Haematopoietic stem cells and early lymphoid progenitors occupy distinct bone marrow niches. Nature. 2013; 495(7440):231-5.
21. Kobayashi H, Butler J M, O'Donnell R, Kobayashi M, Ding B S, Bonner B, Chiu V K, Nolan D J, Shido K, Benjamin L, et al. Angiocrine factors from Akt-activated endothelial cells balance self-renewal and differentiation of haematopoietic stem cells. Nature cell biology. 2010; 12(11): 1046-56.
22. Butler J M, Nolan D J, Vertes E L, Varnum-Finney B, Kobayashi H, Hooper A T, Seandel M, Shido K, White I A, Kobayashi M, et al. Endothelial cells are essential for the self-renewal and repopulation of Notch-dependent hematopoietic stem cells. Cell stem cell. 2010; 6(3):251-64.
23. Poulos M G, Guo P, Kofler N M, Pinho S, Gutkin M C, Tikhonova A, Aifantis I, Frenette P S, Kitajewski J, Rafii S, et al. Endothelial Jagged-1 is necessary for homeostatic and regenerative hematopoiesis. Cell reports. 2013; 4(5): 1022-34.
24. Greenbaum A, Hsu Y M, Day R B, Schuettpelz L G, Christopher M J, Borgerding J N, Nagasawa T, and Link D C. CXCL12 in early mesenchymal progenitors is required for haematopoietic stem-cell maintenance. Nature. 2013; 495(7440):227-30.
25. Himburg H A, Muramoto G G, Daher P, Meadows S K, Russell J L, Doan P, Chi J T, Salter A B, Lento W E, Reya T, et al. Pleiotrophin regulates the expansion and regeneration of hematopoietic stem cells. Nat Med. 2010; 16(4):475-82.
26. Donnini A, Re F, Orlando F, and Provinciali M. Intrinsic and microenvironmental defects are involved in the age-related changes of Lin−c-kit+ hematopoietic progenitor cells. Rejuvenation Res. 2007; 10(4):459-72.
27. Kusumbe A P, Ramasamy S K, Itkin T, Mae M A, Langen U H, Betsholtz C, Lapidot T, and Adams R H. Age-dependent modulation of vascular niches for haematopoietic stem cells. Nature. 2016; 532(7599):380-4.
28. Vas V, Senger K, Dorr K, Niebel A, and Geiger H. Aging of the microenvironment influences clonality in hematopoiesis. PLoS One. 2012; 7(8):e42080.
29. Vas V, Wandhoff C, Dorr K, Niebel A, and Geiger H. Contribution of an aged microenvironment to aging-associated myeloproliferative disease. PLoS One. 2012; 7(2):e31523.

30. Guidi N, Sacma M, Standker L, Soller K, Marka G, Eiwen K, Weiss J M, Kirchhoff F, Weil T, Cancelas J A, et al. Osteopontin attenuates aging-associated phenotypes of hematopoietic stem cells. EMBO J. 2017.

31. Claesson-Welsh L. Vascular permeability—the essentials. Ups J Med Sci. 2015; 120(3):135-43.

32. Pober J S, and Sessa W C. Evolving functions of endothelial cells in inflammation. Nat Rev Immunol. 2007; 7(10):803-15.

33. Csiszar A, Wang M, Lakatta E G, and Ungvari Z. Inflammation and endothelial dysfunction during aging: role of N F-kappaB. J Appl Physiol (1985). 2008; 105(4):1333-41.

34. El Assar M, Angulo J, and Rodriguez-Manas L. Oxidative stress and vascular inflammation in aging. Free Radic Biol Med. 2013; 65(380-401.

35. Mittal M, Siddiqui M R, Tran K, Reddy S P, and Malik A B. Reactive oxygen species in inflammation and tissue injury. Antioxid Redox Signal. 2014; 20(7):1126-67.

36. Zhang C. The role of inflammatory cytokines in endothelial dysfunction. Basic Res Cardiol. 2008; 103(5):398-406.

37. Poulos M G, Crowley M J, Gutkin M C, Ramalingam P, Schachterle W, Thomas J L, Elemento 0, and Butler J M. Vascular Platform to Define Hematopoietic Stem Cell Factors and Enhance Regenerative Hematopoiesis. Stem Cell Reports. 2015; 5(5):881-94.

38. Paneni F, Diaz Canestro C, Libby P, Luscher T F, and Camici G G. The Aging Cardiovascular System: Understanding It at the Cellular and Clinical Levels. J Am Coll Cardiol. 2017; 69(15): 1952-67.

39. Tian X L, and Li Y. Endothelial cell senescence and age-related vascular diseases. J Genet Genomics. 2014; 41(9):485-95.

40. Brandes R P, Fleming I, and Busse R. Endothelial aging. Cardiovasc Res. 2005; 66(2):286-94.

41. Tuljapurkar S R, McGuire T R, Brusnahan S K, Jackson J D, Garvin K L, Kessinger M A, Lane J T, BJ O K, and Sharp J G. Changes in human bone marrow fat content associated with changes in hematopoietic stem cell numbers and cytokine levels with aging. J Anat. 2011; 219(5): 574-81.

42. Latchney S E, and Calvi L M. The aging hematopoietic stem cell niche: Phenotypic and functional changes and mechanisms that contribute to hematopoietic aging. Semin Hematol. 2017; 54(1):25-32.

43. Poulos M G, Ramalingam P, Gutkin M C, Kleppe M, Ginsberg M, Crowley M J, Elemento O, Levine R L, Rafii S, Kitajewski J, et al. Endothelial-specific inhibition of N F-kappaB enhances functional haematopoiesis. Nat Commun. 2016; 7(13829).

44. Chute J P, Muramoto G G, Salter A B, Meadows S K, Rickman D W, Chen B, Himburg H A, and Chao N J. Transplantation of vascular endothelial cells mediates the hematopoietic recovery and survival of lethally irradiated mice. Blood. 2007; 109(6):2365-72.

45. Salter A B, Meadows S K, Muramoto G G, Himburg H, Doan P, Daher P, Russell L, Chen B, Chao N J, and Chute J P. Endothelial progenitor cell infusion induces hematopoietic stem cell reconstitution in vivo. Blood. 2009; 113(9):2104-7.

46. Montfort M J, Olivares C R, Mulcahy J M, and Fleming W H. Adult blood vessels restore host hematopoiesis following lethal irradiation. Experimental hematology. 2002; 30(8):950-6.

47. Balducci L. Myelosuppression and its consequences in elderly patients with cancer. Oncology (Williston Park). 2003; 17(11 Suppl 11):27-32.

48. Till J E, and Mc C E. A direct measurement of the radiation sensitivity of normal mouse bone marrow cells. Radiat Res. 1961; 14(213-22.

49. Li X M, Hu Z, Jorgenson M L, Wingard J R, and Slayton W B. Bone marrow sinusoidal endothelial cells undergo nonapoptotic cell death and are replaced by proliferating sinusoidal cells in situ to maintain the vascular niche following lethal irradiation. Experimental hematology. 2008; 36(9): 1143-56.

50. Hooper A T, Butler J M, Nolan D J, Kranz A, Lida K, Kobayashi M, Kopp H G, Shido K, Petit I, Yanger K, et al. Engraftment and reconstitution of hematopoiesis is dependent on VEGFR2-mediated regeneration of sinusoidal endothelial cells. Cell stem cell. 2009; 4(3):263-74.

51. Ergen A V, Boles N C, and Goodell M A. Rantes/Cc15 influences hematopoietic stem cell subtypes and causes myeloid skewing. Blood. 2012; 119(11):2500-9.

52. Li B, Bailey A S, Jiang S, Liu B, Goldman D C, and Fleming W H. Endothelial cells mediate the regeneration of hematopoietic stem cells. Stem Cell Res. 2010; 4(1): 17-24.

53. Wong A K, Llanos P, Boroda N, Rosenberg S R, and Rabbany S Y. A Parallel-Plate Flow Chamber for Mechanical Characterization of Endothelial Cells Exposed to Laminar Shear Stress. Cell Mol Bioeng. 2016; 9(1):127-38.

54. Spandidos A, Wang X, Wang H, Dragnev S, Thurber T, and Seed B. A comprehensive collection of experimentally validated primers for Polymerase Chain Reaction quantitation of murine transcript abundance. BMC genomics. 2008; 9(633.

55. Spandidos A, Wang X, Wang H, and Seed B. PrimerBank: a resource of human and mouse PCR primer pairs for gene expression detection and quantification. Nucleic acids research. 2010; 38(Database issue):D792-9.

56. Wang X, and Seed B. A PCR primer bank for quantitative gene expression analysis. Nucleic acids research. 2003; 31(24):e154.

57. Hu Y, and Smyth G K. ELDA: extreme limiting dilution analysis for comparing depleted and enriched populations in stem cell and other assays. J Immunol Methods. 2009; 347(1-2):70-8.

What is claimed is:

1. A method for enhancing the engraftment capabilities of hematopoietic cells in an aged hematopoietic system of a human subject comprising an aged HSC microenvironment or niche comprising aged bone marrow and an aged hematopoietic cell population comprising an aged myeloid lineage and an aged lymphoid lineage, wherein the subject has a disease or disorder selected from the group consisting of: a bone marrow disease, cancer and an autoimmune disorder, the method comprising:
   (a) providing a hematopoietic cell population, wherein
      (i) the hematopoietic cell population is derived from cord blood, bone marrow, mobilized peripheral blood, or placenta, and
      (ii) the hematopoietic cell population comprises at least one of hematopoietic stem cells (HSCs), hematopoietic progenitor cells (HPCs) and CD34+ cells;
   (b) contacting the hematopoietic cell population with bone marrow (BM) endothelial cells in vitro,
   wherein the BM endothelial cells (BMECs) are derived from a young individual,
   wherein the young individual is 35 years of age or less, and
   wherein the young BMECs are defined as VECAD+CD31+Lin−CD45−TER119−;
   (c) incubating the hematopoietic cell population of (a) and the BM endothelial cells of (b) in vitro for a period of time to produce a mixed hematopoietic cell/BM endothelial cell population; and
   (d) transplanting the mixed hematopoietic cell/BM endothelial cell population into the human subject,
   wherein the aged hematopoietic system of the subject, when compared to the hematopoietic system comprising the HSC niche, bone marrow, hematopoietic cell population comprising the myeloid lineage and the lymphoid lineage of the young individual, functionally comprises
      (1) a compromised adaptive immunity due to
         (i) reduced T and B lymphocyte function; and
         (ii) a decreased number and/or function of aged lymphoid progenitors;
      (2) a reduced ability to support repopulating activity of HSCs;
      (3) preferential differentiation towards the myeloid lineage at expense of B and T lymphoid cells of the lymphoid lineage; and
      (4) a reduced frequency of VECAD+CD31+CD45−TER119− BM endothelial cells and an increased frequency of VECAD−CD31−CD45−TER119− pan-BM stromal cells;
   (e) wherein the transplanting, when compared to a control hematopoietic cell population not contacted with young BMECs,
      (A) increases engraftment of the mixed hematopoietic cell population;
      (B) the young BMECs enhance output of B cell and T cell lineages in the hematopoietic system of the subject;
      (C) increases bone marrow reconstitution, homing and/or proliferation of the hematopoietic cell population of the subject in vivo, compared to the control;
      (D) increases recovery of WBC, RBC and platelet cell counts in peripheral blood of the subject; and
      (E) increases hematopoietic repopulating activity of the HSCs of the subject compared to whole bone marrow administration alone;
   wherein the increase in hematopoietic cell repopulating activity includes an increase in number of hematopoietic colonies that formed in the spleen following transplantation.

2. The method of claim 1, wherein
   (a) the BM endothelial cells are derived from an individual 30 years of age or less;
   (b) the BM endothelial cells are derived from an individual 25 years of age or less;
   (c) the BM endothelial cells are derived from donor bone marrow or cord blood;
   (d) the hematopoietic cell/BM endothelial cell population is treated with an additional therapeutic agent prior to, concurrently with, or after transplantation;
   (e) aging of the hematopoietic cell population in the subject is delayed; or
   (f) the control hematopoietic cell population is aged matched to the HSCs in claim 1(a);
   (g) the subject is an individual of at least 45 years of age; or
   (h) the subject is an individual of at least 65 years of age.

3. The method of claim 2, wherein the hematopoietic cell population of step (a) is a purified population of HSCs.

4. The method of claim 3, wherein the HSCs are derived from donor bone marrow or cord blood.

5. A method of promoting hematopoietic recovery in a human subject undergoing a myelosuppressive regimen,
   wherein the myelosuppressive regimen lowers the number of normal red blood cells, white blood cells, and platelets in blood and bone marrow;
   wherein the subject has a disease or disorder selected from the group consisting of: a bone marrow disease, cancer and an autoimmune disorder,
   wherein the human subject comprises an aged hematopoietic system comprising an aged HSC microenvironment or niche comprising aged bone marrow and an aged hematopoietic cell population comprising an aged myeloid lineage and an aged lymphoid lineage, which, when compared to a hematopoietic system comprising an HSC niche comprising bone marrow and a hematopoietic cell population comprising a myeloid lineage and a lymphoid lineage of a young individual, wherein the young individual is 35 years of age or less, functionally comprises:
      (1) a compromised adaptive immunity due to
         a. a reduced T and B lymphocyte function and
         b. a decreased number and/or function of aged lymphoid progenitors;
      (2) a reduced ability to support HSC repopulating activity;
      (3) preferential differentiation towards the myeloid lineage at the expense of the lymphoid lineage; and
      (4) a reduced frequency of VECAD+CD31+CD45−TER119− BM endothelial cells and an increased frequency of VECAD−CD31−CD45−TER119− pan-BM stromal cells;
   the method comprising
   (a) expanding a population of bone marrow endothelial cells (BMECs) in vitro, wherein the BM endothelial cells are derived from a young individual, and wherein young BMECs are defined as VECAD+CD31+Lin-CD45−TER119− cells;
   (b) contacting the BMECs with a population of hematopoietic cells in vitro to form a mixed hematopoietic cell/BM endothelial cell population; and
   (c) co-infusing the subject with the mixed hematopoietic cell/BM endothelial cell population;

wherein the method, when compared to a control human subject comprising the aged hematopoietic system that received a hematopoietic cell population not contacted with young BMECs:
- (A) increases engraftment of the mixed hematopoietic cell population in the subject,
- (B) enhances output of B cell and T cell lineages in the lymphoid lineage of the hematopoietic system of the subject;
- (C) increases bone marrow reconstitution, homing and/or proliferation of the hematopoietic cell population of the subject in vivo,
- (D) increases recovery of WBC, RBC and platelet cell counts in peripheral blood of the subject; and
- (E) increases hematopoietic repopulating activity of the HSCs compared to whole bone marrow administration alone;

wherein the increase in hematopoietic cell repopulating activity includes an increase in number of hematopoietic colonies that formed in the spleen following transplantation;

thereby promoting hematopoietic recovery in the subject.

6. The method of claim 1, wherein
- (a) the subject has previously been treated with a myelosuppressive regimen; the subject is currently being treated with a myelosuppressive regimen; or the subject will undergo treatment with a myelosuppressive regimen; and
- (b) the transplanting of the mixed hematopoietic cell/BM endothelial cell population rejuvenates hematopoietic stem cell and vascular function following the myelosuppression.

7. The method of claim 5, wherein
- (a) the BM endothelial cells are derived from donor bone marrow or cord blood;
- (b) the BM endothelial cells are derived from an individual 30 years of age or less;
- (c) the BM endothelial cells are derived from a donor 25 years of age or less;
- (d) the control hematopoietic cell population is aged matched to the HSCs in claim 5 (1);
- (e) the subject is an individual of at least 45 years of age; or
- (f) the subject is an individual of at least 65 years of age.

8. The method of claim 7, wherein the hematopoietic cell population of step (b) is a purified population of HSCs.

9. The method of claim 8, wherein the HSCs are derived from donor bone marrow or cord blood.

10. The method of claim 1 or claim 5, wherein the bone marrow disease is leukemia, a defect of the blood cell compartment, or a bone disease induced by chemotherapy or irradiation.

11. The method of claim 7, wherein the bone marrow disease is a leukemia, a defect of the blood cell compartment, or a bone disease induced by chemotherapy or irradiation.

12. The method of claim 6, wherein the myelosuppressive regimen comprises chemotherapy or radiation.

13. The method of claim 1, wherein the subject has received or will receive a hematopoietic stem cell transplant.

* * * * *

SEQUENCE LISTING

<160> NUMBER OF SEQ ID NOS: 24

<210> SEQ ID NO 1
<211> LENGTH: 19
<212> TYPE: DNA
<213> ORGANISM: Mus musculus

<400> SEQUENCE: 1

-continued

```
gttccagcga gggtctacc                                              19

<210> SEQ ID NO 2
<211> LENGTH: 23
<212> TYPE: DNA
<213> ORGANISM: Mus musculus

<400> SEQUENCE: 2
aactcttggc aaacattagg tgt                                         23

<210> SEQ ID NO 3
<211> LENGTH: 19
<212> TYPE: DNA
<213> ORGANISM: Mus musculus

<400> SEQUENCE: 3
atgcctcgcg ctttctctc                                              19

<210> SEQ ID NO 4
<211> LENGTH: 21
<212> TYPE: DNA
<213> ORGANISM: Mus musculus

<400> SEQUENCE: 4
gtagtcccgc tgacagtatg c                                           21

<210> SEQ ID NO 5
<211> LENGTH: 21
<212> TYPE: DNA
<213> ORGANISM: Mus musculus

<400> SEQUENCE: 5
gaatctccga agaggccaga a                                           21

<210> SEQ ID NO 6
<211> LENGTH: 20
<212> TYPE: DNA
<213> ORGANISM: Mus musculus

<400> SEQUENCE: 6
gctgcaacag ggggtaacat                                             20

<210> SEQ ID NO 7
<211> LENGTH: 21
<212> TYPE: DNA
<213> ORGANISM: Mus musculus

<400> SEQUENCE: 7
tgcatcagtg acggtaaacc a                                           21

<210> SEQ ID NO 8
<211> LENGTH: 21
<212> TYPE: DNA
<213> ORGANISM: Mus musculus

<400> SEQUENCE: 8
ttcttcagcc gtgcaacaat c                                           21

<210> SEQ ID NO 9
<211> LENGTH: 20
<212> TYPE: DNA
<213> ORGANISM: Mus musculus
```

<400> SEQUENCE: 9
cctcgggtca gtttgagctg                                        20

<210> SEQ ID NO 10
<211> LENGTH: 22
<212> TYPE: DNA
<213> ORGANISM: Mus musculus

<400> SEQUENCE: 10
ccttgaggca cactttgaag ta                                     22

<210> SEQ ID NO 11
<211> LENGTH: 22
<212> TYPE: DNA
<213> ORGANISM: Mus musculus

<400> SEQUENCE: 11
caatgacacc actccagatg ag                                     22

<210> SEQ ID NO 12
<211> LENGTH: 19
<212> TYPE: DNA
<213> ORGANISM: Mus musculus

<400> SEQUENCE: 12
ggccaaagac gtcgttgcg                                         19

<210> SEQ ID NO 13
<211> LENGTH: 19
<212> TYPE: DNA
<213> ORGANISM: Mus musculus

<400> SEQUENCE: 13
cccatccgat tccccttcg                                         19

<210> SEQ ID NO 14
<211> LENGTH: 22
<212> TYPE: DNA
<213> ORGANISM: Mus musculus

<400> SEQUENCE: 14
ggttttctgt tgcgaggtca tc                                     22

<210> SEQ ID NO 15
<211> LENGTH: 20
<212> TYPE: DNA
<213> ORGANISM: Mus musculus

<400> SEQUENCE: 15
ttccaggcaa ccttctccga                                        20

<210> SEQ ID NO 16
<211> LENGTH: 20
<212> TYPE: DNA
<213> ORGANISM: Mus musculus

<400> SEQUENCE: 16
actgccgcta ttcttgtccc                                        20

<210> SEQ ID NO 17
<211> LENGTH: 21
<212> TYPE: DNA
<213> ORGANISM: Mus musculus

```
<400> SEQUENCE: 17
ccaggaaaca tcagtgagtc c                                          21

<210> SEQ ID NO 18
<211> LENGTH: 22
<212> TYPE: DNA
<213> ORGANISM: Mus musculus

<400> SEQUENCE: 18
ggatggaact tggaatcggt ca                                         22

<210> SEQ ID NO 19
<211> LENGTH: 21
<212> TYPE: DNA
<213> ORGANISM: Mus musculus

<400> SEQUENCE: 19
gtgtcagaac actgtagcca c                                          21

<210> SEQ ID NO 20
<211> LENGTH: 22
<212> TYPE: DNA
<213> ORGANISM: Mus musculus

<400> SEQUENCE: 20
tcaaaggcaa tctggcatga ag                                         22

<210> SEQ ID NO 21
<211> LENGTH: 23
<212> TYPE: DNA
<213> ORGANISM: Mus musculus

<400> SEQUENCE: 21
tagtccttcc tacccccaatt tcc                                       23

<210> SEQ ID NO 22
<211> LENGTH: 21
<212> TYPE: DNA
<213> ORGANISM: Mus musculus

<400> SEQUENCE: 22
ttggtcctta gccactcctt c                                          21

<210> SEQ ID NO 23
<211> LENGTH: 21
<212> TYPE: DNA
<213> ORGANISM: Mus musculus

<400> SEQUENCE: 23
cgtgcgtgac atcaaagaga a                                          21

<210> SEQ ID NO 24
<211> LENGTH: 18
<212> TYPE: DNA
<213> ORGANISM: Mus musculus

<400> SEQUENCE: 24
ggccatctcc tgctcgaa                                              18
```